(12) United States Patent
Medin et al.

(10) Patent No.: US 10,022,405 B2
(45) Date of Patent: Jul. 17, 2018

(54) IL-12 IMMUNOTHERAPY FOR CANCER

(71) Applicant: University Health Network, Toronto (CA)

(72) Inventors: Jeffrey A. Medin, North York (CA); Christopher J. Paige, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 15/358,965

(22) Filed: Nov. 22, 2016

(65) Prior Publication Data

US 2017/0136072 A1 May 18, 2017

Related U.S. Application Data

(60) Division of application No. 14/283,966, filed on May 21, 2014, which is a continuation of application No. 12/598,899, filed as application No. PCT/CA2008/000849 on May 5, 2008, now Pat. No. 8,765,462.

(60) Provisional application No. 60/916,136, filed on May 4, 2007.

(51) Int. Cl.
A61K 35/545 (2015.01)
(52) U.S. Cl.
CPC .................. A61K 35/545 (2013.01)
(58) Field of Classification Search
CPC .................................................. A61K 35/545
See application file for complete search history.

(56) References Cited

U.S. PATENT DOCUMENTS

| | | |
|---|---|---|
| 5,240,846 A | 8/1993 | Collins et al. |
| 5,399,346 A | 3/1995 | Anderson et al. |
| 5,436,146 A | 7/1995 | Shenk et al. |
| 5,529,774 A | 6/1996 | Barba et al. |
| 5,547,932 A | 8/1996 | Curiel et al. |
| 5,639,642 A | 6/1997 | Kjeldsen et al. |
| 5,645,829 A | 7/1997 | Shockley et al. |
| 5,656,465 A | 8/1997 | Panicali et al. |
| 5,658,567 A | 8/1997 | Calhoun et al. |
| 5,670,488 A | 9/1997 | Gregory et al. |
| 5,672,344 A | 9/1997 | Kelley et al. |
| 5,741,486 A | 4/1998 | Pathak et al. |
| 5,817,492 A | 10/1998 | Saito et al. |
| 5,830,880 A | 11/1998 | Sedlacek et al. |
| 5,854,019 A | 12/1998 | Sedlacek et al. |
| 5,869,040 A | 2/1999 | Oin |
| 5,910,488 A | 6/1999 | Nabel et al. |
| 5,911,983 A | 6/1999 | Barranger et al. |
| 5,928,214 A | 7/1999 | Rubinstein et al. |
| 5,928,914 A | 7/1999 | Leboulch et al. |
| 5,962,318 A | 10/1999 | Rooney et al. |
| 6,312,682 B1 | 11/2001 | Kingsman et al. |
| 6,669,936 B2 | 12/2003 | Kingsman et al. |
| 6,682,907 B1 | 1/2004 | Charneau et al. |
| 7,198,950 B2 | 4/2007 | Trono et al. |
| 7,575,924 B2 | 8/2009 | Trono et al. |
| 7,790,419 B2 | 9/2010 | Kingsman et al. |
| 7,968,332 B2 | 6/2011 | Charneau et al. |
| 7,981,671 B2 | 7/2011 | Charneau et al. |
| 8,093,042 B2 | 1/2012 | Charneau et al. |
| 8,329,462 B2 | 12/2012 | Trono et al. |
| 8,349,606 B2 | 1/2013 | Charneau et al. |
| 8,367,068 B2 | 2/2013 | Charneau et al. |
| 8,450,087 B2 | 5/2013 | Charneau et al. |
| 8,460,678 B2 | 6/2013 | Charneau et al. |
| 8,512,993 B2 | 8/2013 | Charneau et al. |
| 8,512,994 B2 | 8/2013 | Charneau et al. |
| 8,551,773 B2 | 10/2013 | Trono et al. |
| 8,748,169 B2 | 6/2014 | Trono et al. |
| 9,023,646 B2 | 5/2015 | Trono et al. |
| 9,238,824 B2 | 1/2016 | Charneau et al. |
| 9,340,798 B2 | 5/2016 | Trono et al. |
| 9,476,062 B2 | 10/2016 | Trono et al. |
| 2003/0072938 A1 | 4/2003 | Kappes et al. |
| 2006/0040347 A1 | 2/2006 | Charneau et al. |
| 2009/0074733 A1 | 3/2009 | Medin et al. |
| 2013/0115692 A1 | 5/2013 | Trono et al. |
| 2015/0191745 A1 | 7/2015 | Charneau et al. |
| 2016/0068862 A1 | 3/2016 | Trono et al. |
| 2016/0375152 A1 | 12/2016 | Trono et al. |
| 2017/0067079 A1 | 3/2017 | Trono et al. |

FOREIGN PATENT DOCUMENTS

| | | |
|---|---|---|
| CA | 2246005 A1 | 4/2000 |
| CA | 2253790 A1 | 4/2000 |
| EP | 1792997 A1 | 6/2007 |
| WO | WO-97/31119 A1 | 8/1997 |

(Continued)

OTHER PUBLICATIONS

Pegram et al.; Tumor-targeted T cells modified to secrete IL-12 eradicated systemic tumors without need for prior conditioning; Blood; vol. 119; No. 18, pp. 4133-4141, published May 3, 2012 (Year: 2012).*
Zufferey et al., "Self-inactivating lentivirus vector for safe and efficient in vivo gene delivery," J. Virol. 72(12):9873-9880 (1998).
Miyoshi et al., "Development of self-inactivating lentivirus vector," J. Virol. 72(10): 8150-8157 (1998).
Charneau et al., "HIV-1 mutants with abnormal central initiation and termination of reverse transcription are defective in a late step of viral DNA nuclear import," Meeting on Retroviruses, May 1, Cold Spring Harbor, NY. p. 127 (1995) (2 pages).
Zufferey et al., "Woodchuck hepatitis virus posttranscriptional regulatory element enhances expression of transgenes delivered by retroviral vectors," J. Virol. 73(4):2886-2892 (1999).

(Continued)

Primary Examiner — Antonio Galisteo Gonzalez
(74) Attorney, Agent, or Firm — Clark & Elbing LLP

(57) ABSTRACT

Compositions and methods far delivering immune modulatory molecules to result in a therapeutic effect are disclosed. The compositions and methods use stably integrating lentiviral delivery systems. The methods are useful for therapeutically and prophylactically treating cancer such as leukemia.

20 Claims, 12 Drawing Sheets

(56) References Cited

FOREIGN PATENT DOCUMENTS

| WO | WO-9941404 A2 | 8/1999 |
|----|---------------|--------|
| WO | WO-99/55892 A1 | 11/1999 |
| WO | WO-00/00600 A2 | 1/2000 |
| WO | WO-01/27304 A2 | 4/2001 |
| WO | WO-02080851 A2 | 10/2002 |
| WO | WO-2003029412 A2 | 4/2003 |
| WO | WO-03055439 A2 | 7/2003 |
| WO | WO-2008116316 A1 | 10/2008 |
| WO | WO-2008134878 A1 | 11/2008 |
| WO | WO-2008134879 A1 | 11/2008 |

OTHER PUBLICATIONS

Dull et al., "A third-generation lentivirus vector with a conditional packaging system," J. Virol. 72(11):8463-8471 (1998).

Tripathy et al., "Stable delivery of physiologic levels of recombinant erythropoietin to the systemic circulation by intramuscular injection of replication-defective adenovirus," Proc. Natl. Acad. Sci. USA. 91(24): 11557-11561 (1994).

Office Action for Canadian Patent Application No. 2,723,320, dated Nov. 13, 2015 (4 pages).

Zennou et al., "HIV-1 genome nuclear import is mediated by a central DNA flap," Cell. 101(2):173-185 (2000).

Follenzi et al., "Gene transfer by lentiviral vectors is limited by nuclear translocation and rescued by HIV-1 pol sequences," Nat. Genet. 25(2): 217-222 (2000).

Pajtasz-Piasecka E. et al: "Loss of tumorigenicity of murine colon carcinoma MC38/0 cell line after transduction with a retroviral vector carrying murine IL-12 genes" Folia Biologica (Prague), vol. 50, No. 1, 2004. pp. 7-14. XP002628036, ISSN:0015-5500.

Pizzoferrato, PhD thesis entitled "A Murine Model of B-Cell Lymphoma: Manipulation of Costimulatory and Cytokine Expression to Generate Effective Immunotherapeutic Cancer Vaccines", National Library of Canada, 1999.

Moolten FL. Tumor chemosensitivity conferred by inserted herpes thymidine kinase genes: paradigm for a prospective cancer control strategy. Cancer Res. 1986; 46: 5276-5281.

Ramezani Ali et al. Lentiviral Vectors for Enhanced Gene Expression in Human Hematopoietic Cells. Molecular Therapy, vol. 2, No. 5, Nov. 2000, pp. 458-469.

Satthaporn S and Eremin O., Dendritic Cells(1): Biological Functions. Journal of the Royal College of Surgeons of Edinburgh, Feb. 2001, 46:9-20.

Weichold FF . et al. Regulation of a graft-versus-leukemia effect by major histocompatibility complex class II molecules on leukemia cells: HLA-DR1 expression renders K562 cell tumors resistant to adoptively transferred lymphocytes in severe combined immunodeficiency mice/nonobese diabetic mice. Blood. 1997; 90: 4553-4558.

Moolten FL, Wells JM. Curability of tumors bearing herpes thymidine kinase genes transferred by retroviral vectors. J Natl Cancer Inst. 1990; 82: 297-300.

Kanazawa T. et al. Suicide gene therapy using AAV-HSVtk/ ganciclovir in combination with irradiation results in regression of human head and neck cancer xenografts in nude mice. Gene Ther. Jan. 2003;10(1):51-8.

Lizee et al. Lentivirus Vector-Mediated Expression of Tumor-Associated Epitopes by Human Antigen Presenting Cells. Human Gene Therapy, 2004, 15:393-404.

Spencer DM. Developments in suicide genes for preclinical and clinical applications. Curr Opin Mol Ther. 2000; 2: 433-440.

Kokoris MS, Black ME. Characterization of herpes simplex virus type 1 thymidine kinase mutants engineered for improved ganciclovir or acyclovir activity. Protein Sci. 2002; 11: 2267-2272.

Osborn Mark J. et al. A Picornaviral 2A-Like Sequence-Based Tricistronic Vector Allowing for High-Level Therapeutic Gene Expression Coupled to a Dual-Reporter System. Molecular Therapy 2005; 12 (3), 569-574.

Szymczak AL. et al. Nat Biotechnol. 2004;22(5):589-94.

Chen X. et al. Synthesis and evaluation of novel thymidine analogs as antitumor and antiviral agents. J Med Chem. 1996 39(17):3412-7.

Riddell SR. et al. T-cell mediated rejection of gene-modified HIV-specific cytotoxic T lymphocytes in HIV-infected patients. Nat Med. 1996; 2: 216-223.

Yee, Cassian . Adoptive T cell therapy: Addressing challenges in cancer immunotherapy. J Translational Medicine, 2005 3(17): doi;0. 1186/1479-5876-3-17.

Breckpot K. et al: "Lentiviral vectors for cancer immunotherapy: transforming infectious particles into therapeutics", Gene Therapy, vol. 14, No. 11, Mar. 22, 2007, pp. 847-862.

Lal S. et al. Suicide genes: past, present and future perspectives. Immunol Today. 2000; 21: 48-54.

Gruh et al., Shuttle system allowing simplified cloning of expression cassettes into advanced generation lentiviral vectors. Biotechniques. Apr. 2005; 38(4):530, 532, 534.

Bondanza A. et al. Suicide gene therapy of graft-versus-host disease induced by central memory human T lymphocytes. Blood. 107(5):1828-36, 2006.

Thompson, JD et al., Clustal W: Improving the sensitivity of progressive multiple sequence alignment through sequence weighting position-specific gap penalties and weight matrix choice. Nucleic Acid Res. 22:4673-4680, 1994.

Wang, Jean C.Y. and Dick, John E. Cancer Stem Cells: Lessons from Leukemia. Trends in Cell Biology. 15 (9):494-501,2005.

Furman PA. et al. Phosphorylation of 3'-azido-3'-deoxythymidine and selective interaction of the 5'-triphosphate with human immunodeficiency virus reverse transcriptase. Proc Natl Acad Sci U S A. 1986; 83: 8333-8337.

Kang T.H. et al. Enhancement of dendritic cell-based vaccine potency by targeting antigen to endosomal/lysosomal compartments' Immunology Letters vol. 106, No. 2, 2006, pp. 126-134.

Tahara H. et al. Effective eradication of established murine tumors with IL-12 gene therapy using a polycistronic retroviral vector. Journal of Immunology, 1995, vol. 154, No. 12, pp. 6466-6474.

Kershaw MH et al. Supernatural T cells: genetic modification of T cells for cancer therapy. Nat Rev Immunol. 2005; 5;928-940.

Frick LW. et al. Effects of 3'-azido-3'-deoxythymidine on the deoxynucleotide triphosphate pools of cultured human cells. Biochem Biophys Res Commun. 1988; 154: 124-129.

Wu T.-C. et al. Engineering an intracellular pathway for major histocompatibility complex class II presentation of antigens' Proc. Natl. Acad. Sci. USA vol. 92, No. 25, Dec. 1995, pp. 11671-11675.

Su Z. et al. Enhanced induction of telomerase-specific CD4+ T Cells using dendritic cells transfected with RNA encoding a chimeric gene product' Cancer Research vol. 62, No. 17, Sep. 1, 2002, pp. 5041-5048.

Humrich J. et al. Viral vectors for dendritic cell-based immunotherapy' Current Topics in Microbiology and Immunology vol. 276, 2003, pp. 241-259.

Lavie A. et al. The bottleneck in AZT activation. Nat Med. 1997; 3: 922-924.

Kaplan J.M. et al. New cancer vaccine approaches. Drugs of Today vol. 40, No. 11, 2004, pp. 913-929.

Zitvogel et al. Construction and characterization of retroviral vectors expressing biologically active human Interleukin-12". Human Gene Therapy. Dec. 1994, vol. 5, pp. 1493-1506.

Chow HH. et al. In vivo tissue disposition of 3'-azido-3'-deoxythymidine and its anabolites in control and retrovirus-infected mice. Drug Metab Dispos. 1997; 25; 412-422.

Cazzalini O. et al. Early effects of AZT on mitochondrial functions in the absence of mitochondrial DNA depletion in rat myotubes. Biochem Pharmacol. 2001; 62: 893-902.

Lizee et al. Real-Time Quantitative Reverse Transcriptase-Polymerase Chain Reaction as a Method for Determining Lentiviral Vector Titers and Measuring Transgene Expression. Human Gene Therapy, 2003, 14:497-507.

Barros de Arruda et al. DNA vaccine encoding human immunodeficiency virus-1 Gag, targeted to the major histocompatibility complex II compartment by lysosomal-associated membrane protein, elicits enhanced long-term memory response. Immunology, 2004, 112(1):126-135.

(56) References Cited

OTHER PUBLICATIONS

Sato Takeya et al. Engineered human tmpk/AZT as a novel enzyme/prodrug axis for suicide gene therapy. Molecular Therapy: The Journal of the American Society of Gene Therapy, May 2007 LNKD-Pubmed: 17375075, vol. 15, No. 5, Mar. 20, 2007 (Mar. 20, 2007), pp. 962-970, XP002628039, ISSN: 1525-0016 (p. 962).
Masini A. et al. Zidovudine-induced experimental myopathy: dual mechanism of mitochondrial damage. J Neurol Sci. 1999; 166: 131-140.
Sato et al. A novel Suicide Gene Therapy Approach for Reduction of GvHD Using Lentiviral Delivery of a Modified Human Thymidylate Monophosphate Kinase. Blood, ASH Annual Meeting Abstracts, 2005, 106: Abstract 5252.
Lu et al. Safe two-plasmid production for the first clinical lentivirus vector that achieves >99% transduction in primary cells using a one-step protocol. Journal of Gene Medicine (2004) 6:963-973.
Klump H. et al. Retroviral vector-mediated expression of HoxB4 in hematopoietic cells using a novel coexpression strategy Gene Ther. 2001;8(10):811-7.
Park, et al., Therapeutic levels of human factor VIII and IX using HIV-1 based lentiviral vectors in mouse liver. Blood. vol. 96, No. 3 (Aug. 1, 2000): pp. 1173-1176.
Miller G. et al. Overexpression of interleukin-12 enables dendritic cells to activate NK cells and confer systemic antitumor immunity. The FASEB Journal. Apr. 2003, vol. 17, No. 6, pp. 728-730.
Suzuki T. et al. Vaccination of dendritic cells loaded with interleukin-12-secreting cancer cells augments in vivo antitumor immunity: characteristics of syngeneic and allogeneic antigen-presenting cell cancer hybrid cells. Clinical Cancer Research. Jan. 1, 2005, vol. 11, No. 1, pp. 58-66.
Socie G. Chronic graft-versus-host disease: clinical features and grading systems. Int J Hematol. Apr. 2004;79 (3):216-20.
Ostermann N. et al. Potentiating AZT activation: structures of wild-type and mutant human thymidylate kinase suggest reasons for the mutants' improved kinetics with the HIV prodrug metabolite AZTMP. J Mol Biol. 2000; 304: 43-53.
Robertson MJ et al. Interleukin 12: basic biology and potential applications in cancer treatment. The Oncologist, Feb. 1, 1996, vol. 1, No. 1 & 2, pp. 88-97.
Sterman DH. Adenovirus-mediated herpes simplex virus thymidine kinase/ganciclovir gene therapy in patients with localized malignancy: results of a phase I clinical trial in malignant mesothelioma (Adenoviral Gene Therapy for Mesothelioma). Hum Gene Ther. May 1, 1987;9(7): 1083-92.
Vroemen et al. Loss of gene expression in lentivirus- and retrovirus-transduced neutral progenitor cells is correlated to migration and differentiation in the adult spinal cord. Experimental Neorology, 2005, vol. 195, pp. 127-139.
Blomer U. et al. Highly efficient and sustained gene transfer in adult neurons with a lentivirus vector. J Virol. 1997; 71: 6641-6649.
Mullen et al. Ganciclovir chemoablation of herpes thymidine kinase suicide gene-modified tumors produces tumor necroses and induces systemic immune responses. Hum. Gene Ther. Sep. 20, 1998, vol. 9, No. 14, pp. 2019-2030.
Galimi F. and Verma I.M. Opportunities for the Use of Lentiviral Vectors in Human Gene Therapy. Lentiviral Vectors. vol. 261 of the series Current Topics in Microbiology and Immunology, pp. 245-254, 2002.
Lin K.-Y. et al. Treatment of established tumors with a novel vaccine that enhances major histocompatibility class II presentation of tumor antigen' Cancer Research vol. 56, No. 1, Jan. 1, 1996, pp. 21-26.
Hacein-Bey-Abina S. et al. LMO2-associated clonal T cell proliferation in two patients after gene therapy for SCID-X1. Science. 2003; 302: 415-419.
Colombo Mario P. et al: "Amount of interleukin 12 available at the tumor site is critical for tumor regression", Cancer Research, vol. 56, No. 11, 1996, pp. 2531-2534.

Song K. et al.: IL-12 plasmid-enhanced DNA vaccination against carcinoembryonic antigen (CEA) studied in immune-gene knockout mice' Gene Therapy vol. 7, No. 18, Sep. 2000, pp. 1527-1535.
Medin JA. et al. A bicistronic therapeutic retroviral vector enables sorting of transduced CD34+ cells and corrects the enzyme deficiency in cells from Gaucher patients. Blood. 1996; 87: 1754-1762.
Wildner O, Blaese RM, Morris JC. Therapy of colon cancer with oncolytic adenovirus is enhanced by the addition of herpes simplex virus-thymidine kinase. Cancer Res. 1999; 59: 410-413.
Qin G. et al. Preselective gene therapy for Fabry disease. Proc Natl Acad Sci U S A. 2001; 98: 3428-3433.
Vroemen et al. Purification of Schwann cells by selection of p75 low affinity nerve growth factor receptor expressing cells from adult peripheral nerve. J Neuroscience Methods, 2003, vol. 124, pp. 135-143.
Siatskas C. et al. Specific pharmacological dimerization of KDR in lentivirally transduced human hematopoietic cells activates anti-apoptotic and proliferative effects. FASEB J. 2005; 19: 1752-1754.
Qasim W. et al. T cell transduction and suicide with an enhanced mutant thymidine kinase. Gene Ther. 2002; 9: 824-827.
Medin JA. et al. Efficient transfer of PSA and PSMA cDNAs into DCs generates antibody and T cell antitumor responses in vivo. Cancer Gene Ther. 2005; 12: 540-551.
Strausberg et al., Generation and initial analysis of more than 15,000 full-length human and mouse cDNA sequences Proc. Natl Acad Sci., USA, Dec. 24, 2002; 99(26):16899-903. Epub Dec. 11, 2002.
Bonini C. et al. HSV-TK gene transfer into donor lymphocytes for control of allogeneic graft-versus-leukemia. Science. 1997;276: 1719-1724.
Van Rompay AR. et al. Phosphorylation of nucleosides and nucleoside analogs by mammalian nucleoside monophosphate kinases. Pharmacol Ther. 2000; 87: 189-198.
Li Z. et al. Murine leukemia induced by retroviral gene marking. Science. 2002; 296: 497.
Pizzoferrato, B7-2 Expression Above a Threshold Elicits Anti-Tumor Immunity as Effective as Interleukin-12 and Prolongs Survival in Murine B-Cell Lymphoma, Int. J. Cancer vol. 110, 2004, pp. 61-69.
Doody GM. et al. Activation of B lymphocytes: integrating signals from CD19, CD22 and Fc gamma RIIb1. Curr Opin Immunol. 1996; 8: 378-382.
Johnson AA. et al. Toxicity of antiviral nucleoside analogs and the human mitochondrial DNA polymerase. J Biol Chem. 2001; 276: 40847-40857.
Fujimoto M. et al. CD19 regulates intrinsic B lymphocyte signal transduction and activation through a novel mechanism of processive amplification. Immunol Res. 2000; 22: 281-298.
Kuwata T. et al. Construction of chimeric simian and human immunodeficiency viruses that produce interleukin 12", AIDS Research and Human Retroviruses. Mar. 1, 2000, vol. 16, No. 5, pp. 465-470.
Tedder TF. et al. The CD19/CD21 signal transduction complex of B lymphocytes. Immunol Today. 1994; 15: 437-442.
Sales SD. et al. Zidovudine phosphorylation and mitochondrial toxicity in vitro. Toxicol Appl Pharmacol. 2001; 177: 54-58.
Sato S. et al. Regulation of B lymphocyte development and activation by the CD19/CD21/CD81/Leu 13 complex requires the cytoplasmic domain of CD19. J Immunol. 1997; 159: 3278-3287.
Hamel W. et al. Herpes simplex virus thymidine kinase/ganciclovir-mediated apoptotic death of bystander cells. Cancer Res. 1996;56: 2697-2702.
Greco O, Dachs GU. Gene directed enzyme/prodrug therapy of cancer: historical appraisal and future prospectives. J Cell Physiol. 2001; 187: 22-36.
Brundiers R. et al. Modifying human thymidylate kinase to potentiate azidothymidine activation. J Biol Chem. 1999; 274: 35289-35292.
Smiley ST. et al. Intracellular heterogeneity in mitochondrial membrane potentials revealed by a J-aggregate-forming lipophilic cation JC-1. Proc Natl Acad Sci U S A. 1991; 88: 3671-3675.
Berger C. et al. Analysis of transgene-specific immune responses that limit the in vivo persistence of adoptively transferred HSV-

(56) References Cited

OTHER PUBLICATIONS

TK-modified donor T cells after allogeneic hematopoietic cell transplantation. Blood. 2006; 107:2294-2302.
Green DR, Reed JC. Mitochondria and apoptosis. Science. 1998; 281: 1309-1312.
Labbe Alain et al: "IL-12 immunotherapy of murine leukemia: comparison of systemic versus gene modified cell therapy.", Journal of Cellular and Molecular Medicine, vol. 13, No. 8B, Aug. 2009, pp. 1962-1976.
Qian Cheng et al: "Gene therapy of cancer: induction of anti-tumor immunity.", Cellular & Molecular Immunology Apr. 2004 LNKD-Pubmed:16212896, vol. 1, No. 2, Apr. 2004, pp. 105-111, XP002628040, ISSN:1672-7681 (p. 106).
St Clair MH. et al. 3'-Azido-3'-deoxythymidine triphosphate as an inhibitor and substrate of purified human immunodeficiency virus reverse transcriptase. Antimicrob Agents Chemother. 1987; 31: 1972-1977.
Caux et al. CD34+ Hematopoietic Progenitors from Human Cord Blood Differentiate Along Two Independent Dendritic Cell Pathways in Response to GM-CSF+TNFalpha. J. Exp.Med., 1996, 184:695-706.
Naldini et al., "In vivo gene delivery and stable transduction of nondividing cells by a lentiviral vector," Science. 272(5259):263-7 (1996).
Szymczak AL, Vignali DA. Developer of 2A Peptide-Based Strategies in the Design of Multistronic Vectors. Expert Opin Biol Ther. 2005; 5(5):627-38.
Coplan NL, Bruno MS. Acquired immunodeficiency syndrome and heart disease: the present and the future. Am Heart J. 1989; 117: 1175-1177.
Muller HC. et al. Novel Nucleotide Analogues as Potential Substrates for TMPK, a Key Enzyme in the Metabolism of AZT. Nucleosides Nucleotides Nucleic Acids. 2003:22(5-8);821-3.
Nishiyama Y. et al. Anticellular effects of 9-(2-hydroxyethoxymethyl) guanine against herpes simplex virus-transformed cells. J Gen Virol. 1979; 45: 227-230.
Ji H. et al. Targeting human papillomavirus type 16 E7 to the endosomal/lysomal compartment enhances the antitumor immunity of DNA vaccines against murine human papillomavirus type 16 E7-expressing tumors' Human Gene Therapy vol. 10, No. 17, Nov. 20, 1999, pp. 2727-2740.
McKee EE. et al. Phosphorylation of thymidine and AZT in heart mitochondria: elucidation of a novel mechanism of AZT cardiotoxicity. Cardiovasc Toxicol. 2004; 4: 155-167.
GenBank submission BT020055, submitted Oct. 28, 2014.
Gautam, Subhash C. et al: "Interleukin-12 (IL-12) gene therapy of leukemia: Immune and anti-leukemic effects of IL-12-transduced hematopoietic progenitor cells", Cancer Gene Therapy, vol. 7, No. 7, Jul. 2000 (Jul. 2000), pp. 1060-1068, XP002628037, ISSN: 0929-1903.
Meko JB et al. High cytokine production and effective antitumor activity of a recombinant vaccinia virus encoding murine interleukin 12". Cancer Research, Nov. 1, 1995, vol. 55, pp. 4765-4770.

Mahmoud MS. et al. Enforced CD19 expression leads to growth inhibition and reduced tumorigenicity. Blood. 1999; 94: 3551-3558.
Yoshimitsu M. et al. Bioluminescent imaging of a marking transgene and correction of Fabry mice by neonatal injection of recombinant lentiviral vectors. Proc Natl Acad Sci US A. 2004; 101: 16909-16914.
Sadelain M, Riviere I. Sturm and drang over suicidal lymphocytes. Mol Ther. 2002; 5: 655-657.
Fukui T. et al. Suicide gene therapy for human oral squamous cell carcinoma cell lines with adeno-associated virus vector. Oral Oncol. Apr. 2001;37(3):211-5.
Chang Alex H. et al: "The genetic engineering of hematopoietic stem cells: the rise of lentiviral vectors, the conundrum of the ltr, and the promise of lineage-restricted vectors." Molecular Therapy: The Journal of the American Society of Gene Therapy, vol. 15, No. 3, Mar. 2007, pp. 445-456.
Nair S.K. et al. Induction of primary carcinoembryonic antigen (CEA)-specific cytotoxic T lymphocytes in vitro using human dendritic cells transfected with RNA' Nature Biotechnology vol. 16, Apr. 1998, pp. 364-369.
Obana S. et al: "Induction of anti-tumor immunity by mouse tumor cells transfected with mouse interleukin-12 gene", Japanese Journal of Medical Science and Biology, Tokyo, JP, vol. 48, Jan. 1, 1995, pp. 221-236.
Chen X. et al. Alteration of T cell immunity by lentiviral transduction of human monocyte-derived dendritic cells. Retrovirology, Nov. 1, 2004, vol. 1, No. 1, pp. 37-49.
Mazzolini Guillermo et al: "Gene therapy of cancer with interleukin-12", Current Pharmaceutical Design, Bentham Science Publishers, NL, vol. 9, No. 24, Sep. 1, 2003, pp. 1981-1991.
Roy NS. et al. Functional engraftment of human ES cell-derived dopaminergic neurons enriched by coculture with telomerase-immortalized midbrain astrocytes. Nat. Med. 12(11):1259-68, 2006.
Migita M. et al. Selection of transduced CD34+ progenitors and enzymatic correction of cells from Gaucher patients, with bicistronic vectors. Proc Natl Acad Sci US A. 1995; 92: 12075-12079.
Kirk C.J. et al. Gene-modified dendritic cells for use in tumor vaccines' Human Gene Therapy vol. 11, No. 6, Apr. 10, 2000, pp. 797-806.
Labbe Alain et al: "Murine model of immune-mediated rejection of the acute lymphoblastic leukemia 70Z/3.", Journal of Immunology (Baltimore, MD. : 1950) , vol. 176, No. 9, May 1, 2006, pp. 5354-5361.
Chevez-Barrios P. Response of retinoblastoma with vitreous tumor seeding to adenovirus-mediated delivery of thymidine kinase followed by ganciclovir. J Clin Oncol. Nov. 1, 2005;23(31):7927-35.
Pizzoferrato et al., Enhanced Immunogenicity of B Cell Lymphoma Genetically Engineered to Express Both B7-1 and Interleukin-12, Human Gene Therapy vol. 8, Dec. 10, 1997, pp. 2217-2228.
Miltenyi Biotec product brochure (dated 2006; downloaded Dec. 17, 2012).
Cohen JL. et al. Prevention of graft-versus-host disease in mice using a suicide gene expressed in T lymphocytes. Blood. 1997; 89: 4636-4645.

* cited by examiner

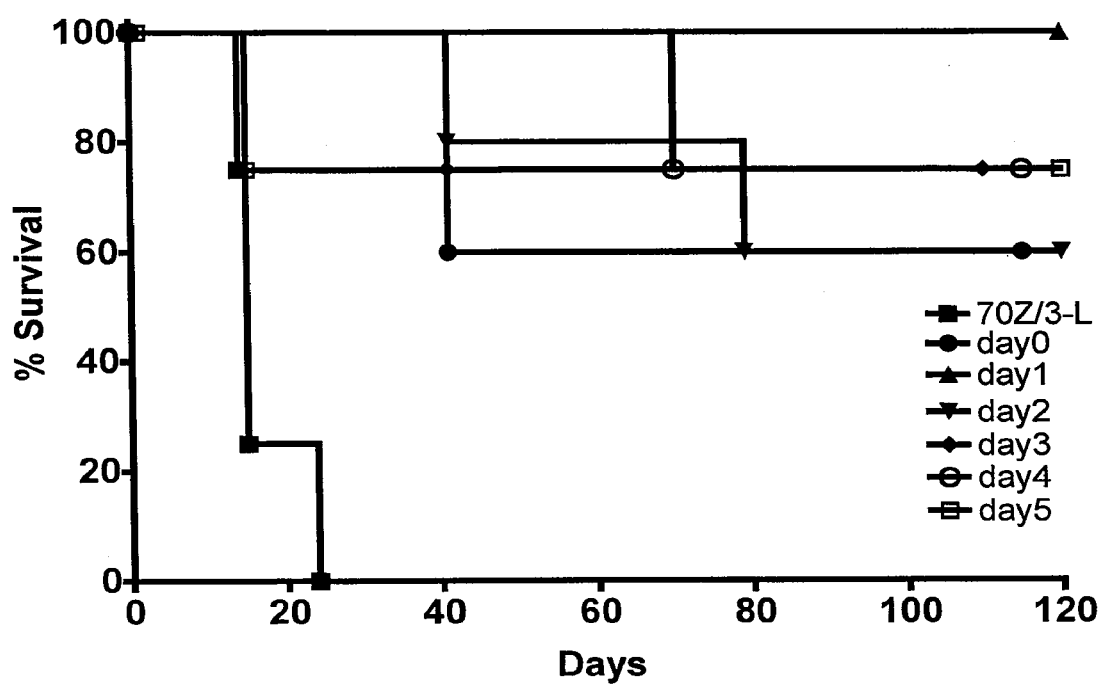

FIGURE 4
a.)
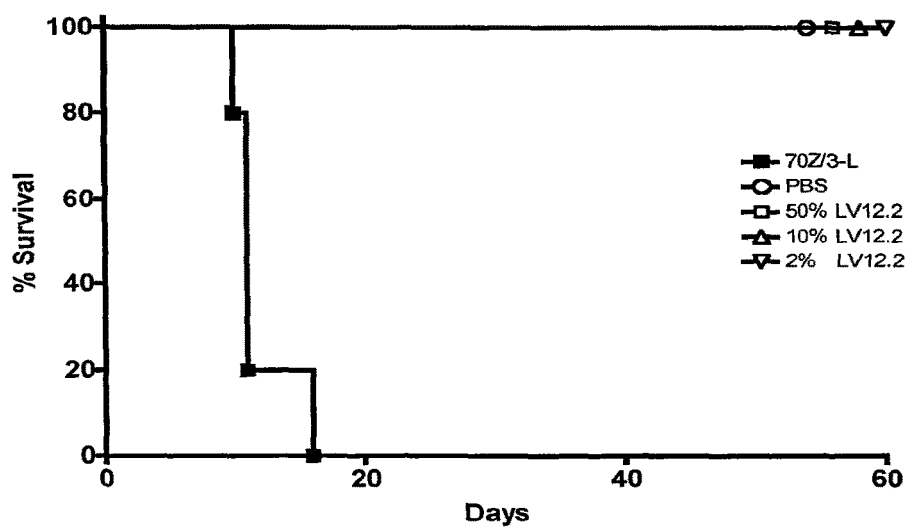
b.)
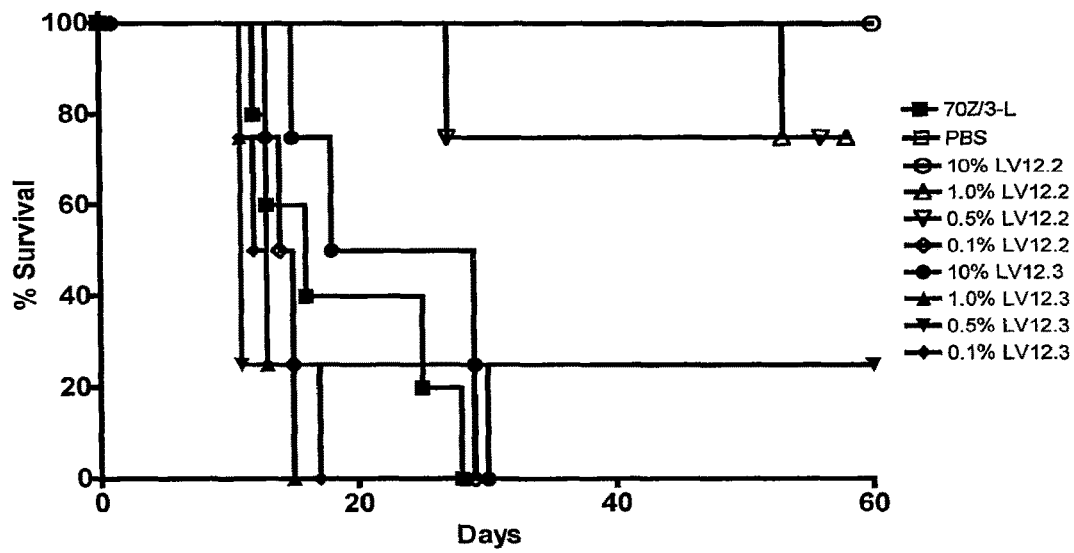

IL-12 IMMUNOTHERAPY FOR CANCER

RELATED APPLICATIONS

The present application is a continuation of copending U.S. patent application Ser. No. 14/283,966, filed May 21, 2014, which is a continuation of copending U.S. patent application Ser. No. 12/598,899, filed Nov. 4, 2009, which is a National stage entry of International Patent Application No. PCT/CA2008/000849, filed May 5, 2008, which claims priority to U.S. Provisional Patent Application No. 60/916,136 filed May 4, 2007, each of these applications being incorporated herein in their entirety by reference.

INCORPORATION OF SEQUENCE LISTING

A computer readable form of the Sequence Listing "51182_003005_Sequence_Listing.txt" (73,894 bytes), submitted via EFS-WEB and created on Nov. 22, 2016, is herein incorporated by reference.

FIELD OF INVENTION

The invention relates generally to compositions and methods for therapeutically and prophylactically treating cancer. In particular, the present invention pertains to IL-12, lentiviral vectors encoding IL-12 for transducing cells and use of the transduced cells for cancer immunotherapy.

BACKGROUND OF THE INVENTION

Cancer immunotherapy aims to overcome the inability of the immune system to efficiently protect against the establishment of tumors or reject established tumors.

Lentiviral Vectors (LVs)

Lentiviral vectors (LVs) are efficient gene transfer agents. They are stable and can be concentrated by ultracentrifugation to high titers. Compared to adenovirus, for example, they generate little immune consequences on their own reducing responses against transduced cells. Advances in LV design, safety, and long-term testing will increase their clinical adaptation. LVs have been used in cancer immuno-gene therapy (Metharom, P. et al., 2001; Firat, H. et al., 2002), the induction of DCs (Esslinger, C. et al., 2003) and antigen presentation for CTL responses (Breckpot, K. et al., 2003; Esslinger, C. et al., 2003), and the transduction of CD34+ cells differentiated into DCs towards HIV/AIDS immunotherapy DCs (Gruber, A. et al., 2003).

Interleukin-12

Cancer cells express antigens. Despite the presence of such antigens, tumors are generally not readily recognized and eliminated by the host, as evidenced by the development of disease. The inability of the immune system to protect against tumors may be due to mechanisms of evasion, active suppression, or sub-optimal activation of the response.

Cytokines are integral to both the innate and acquired immune systems. They can alter the balance of cellular and humoral responses, alter class switching of B lymphocytes and modify innate responses.

Interleukin-12 is a heterodimeric cytokine with multiple biological effects on the immune system. It is composed of two subunits, p35 and p40, both of which are required for the secretion of the active form of IL-12, p70. Interleukin-12 acts on dendritic cells (DC), leading to increased maturation and antigen presentation, which can allow for the initiation of a T cell response to tumor specific antigens. It also drives the secretion of IL-12 by DCs, creating a positive feedback mechanism to amplify the response. Once a response is initiated, IL-12 plays a fundamental role in directing the immune system towards a Th1 cytokine profile, inducing CD4+ T cells to secrete interferon-gamma (IFN-γ) and leading to a CD8+ cytotoxic T cell response.[4] However, IL-12 is also a strong pro-inflammatory cytokine that leads to the secretion of other cytokines including tumor necrosis factor-alpha (TNF-α) which, combined with IFN-γ, is a prerequisite for the development of CD4+ cytotoxic T lymphocytes (CTL).[5] Furthermore, IL-12 can promote the activation of innate immune cells such as macrophages and eosinophils through its induction of IFN-γ and other cytokines. This activation then leads to IL-12 secretion by these cells and further amplification of both the innate and acquired responses.[4] However, high levels of IL-12, and consequently IFN-γ, have also been associated with induction of antagonistic molecules such as IL-10 and the depletion of signaling molecules downstream of IL-12, such as STAT4.[6-8]

Direct injection of recombinant IL-12 has been shown in some mouse models of leukemia.[9-13] While initial human trials employing this approach were less promising (14-17 discussed in 4).

Innovative gene therapy strategies may accelerate the development of prophylactic immunotherapy against cancer.

SUMMARY

The inventors have demonstrated that intraperitoneal (IP) administration of low dose rIL-12 elicits a protective response against an established tumor burden and that this CD8+ T cell-dependent response leads to long-term immune memory. The inventors also delivered IL-12 by way of transduced tumor cells, mediated by a lentiviral delivery system to ensure that optimum concentrations of IL-12 were available at the tumor site. The method of delivering IL-12 is highly effective and is readily applied to a variety of cancers.

The application provides in one aspect, a composition comprising:
a lentiviral vector;
an IL-12 expression cassette.

In one embodiment, the IL-12 expression cassette comprises a polynucleotide optionally encoding a p35 polypeptide and a polynucleotide encoding a p40 polypeptide; or a polynucleotide encoding an IL-12 fusion polypeptide. In another embodiment the IL-12 fusion polypeptide has at least 70% sequence identity to SEQ ID NO: 4 and binds an IL-12 receptor. In a further embodiment, the lentiviral vector optionally comprises one or more of a: 5'-Long terminal repeat (LTR), HIV signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR (SIN-LTR). In yet a further embodiment, the lentiviral vector comprises a central polypurine tract optionally SEQ ID NO:2 and/or a woodchuck hepatitis virus post-transcriptional regulatory element, optionally SEQ ID NO:3; or a sequence having at least 70% sequence identity to SEQ ID NO:2 and/or SEQ ID NO:3. In another embodiment, the lentiviral vector comprises a pHR' backbone. In one embodiment, the lentiviral vector is a clinical grade vector. In one embodiment, the composition further comprises an activator polynucleotide encoding a polypeptide that converts a prodrug to a drug, optionally a modified tmpk polynucleotide. In yet a further embodiment, the activator polynucleotide comprises a tmpk polynucleotide with at least 80% sequence identity to a modified tmpk polynucleotide described herein.

In certain embodiments, the composition further comprises a detection cassette. In one embodiment, the detection cassette comprises a CD19, truncated CD19, CD20, human CD24, murine HSA, human CD25 (huCD25), a truncated form of low affinity nerve growth factor receptor (LNGFR), truncated CD34, eGFP, eYFP, or any other fluorescent protein or erythropoietin receptor (EpoR) polynucleotide; or a polynucleotide with at least 70% sequence identity to said polynucleotide.

In another embodiment, the composition further comprises an immune modulatory cassette. In one embodiment, the immune modulatory cassette comprises a polynucleotide that encodes a polypeptide that modulates an immune cell, optionally a dendritic cell or a T cell, optionally a CD4+ T cell, optionally CD40L, IL-7, or IL-15. In another embodiment the composition is a pharmaceutical composition and further comprises a pharmaceutically acceptable carrier.

In another aspect, the application provides a vector construct comprising: a lentiviral vector;
an IL-12 expression cassette.

In another aspect the application provides an isolated virus comprising the vector construct or composition described herein.

A further aspect provides an isolated cell secreting IL-12 at the or above the threshold level, wherein the cell is optionally transduced with the composition, the vector construct or the isolated virus described herein. In one embodiment, the cell is a cancer cell, optionally an established cell line, optionally a primary cancer cell, optionally a cancer cell derived from a subject. In another embodiment, the cancer cell is a leukemic cell, optionally an ALL cell, an AML cell, a CML cell or a CLL cell. In a further embodiment, the threshold level is at least 1500 pg/mL/$10^6$ cells/2 hrs of IL-12, optionally at least 1500 pg/mL/$10^6$ cells/2 hrs, 1500-2500 pg/mL/$10^6$ cells/2 hrs, 2500-5000 pg/mL/$10^6$ cells/2 hrs, 5000-7500 pg/mL/$10^6$ cells/2 hrs, 7500-10000 pg/mL/$10^6$ cells/2 hrs, 10000-12500 pg/mL/$10^6$ cells/2 hrs, 12500-15000 pg/mL/$10^6$ cells/2 hrs, 15000-17500 pg/mL/$10^6$ cells/2 hrs, 17500-20000 pg/mL/$10^6$ cells/2 hrs or at least 20000 pg/mL/$10^6$ cells/2 hrs of IL-12

Another aspect provides a population of cells comprising isolated cells and/or transduced cells described herein wherein the population of cells optionally comprises at least 0.1 to 1% IL-12 producing cells, optionally leukemic cells, optionally about 0.5%, about 1%, about 1-5%, 5-10%, 10-20% or more IL-12 producing cells, optionally leukemic cells, and wherein the population of cells secretes above the threshold level optionally the threshold level necessary to induce or enhance a CD4+ T cell dependent immune response, optionally at least 1500 pg/mL/$10^6$ cells/2 hrs, 1500-2500 pg/mL/$10^6$ cells/2 hrs, 2500-5000 pg/mL/$10^6$ cells/2 hrs, 5000-7500 pg/mL/$10^6$ cells/2 hrs, 7500-10000 pg/mL/$10^6$ cells/2 hrs, 10000-12500 pg/mL/$10^6$ cells/2 hrs, 12500-15000 pg/mL/$10^6$ cells/2 hrs, 15000-17500 pg/mL/$10^6$ cells/2 hrs, 17500-20000 pg/mL/$10^6$ cells/2 hrs or at least 20000 pg/mL/$10^6$ cells/2 hrs of IL-12. In one embodiment, the population of cells is derived from a clone that secretes IL-12 above the threshold level optionally at least 1500 pg/mL/$10^6$ cells/2 hrs of IL-12.

A further aspect provides a composition comprising the isolated virus, cell or population of cells described herein.

Another aspect of the disclosure provides a method of expressing IL-12 in a cell, optionally a cancer cell comprising contacting the cell with the composition, the vector construct or the isolated virus under conditions that permit transduction of the cell, thereby providing a transduced cell, optionally wherein the IL-12 is secreted. In one embodiment, the method further comprises a step of isolating the transduced cell or isolating a population of cells comprising the transduced cell. In another embodiment, the method further comprises:
growth arresting the transduced cell, the population of cells or composition; and
introducing the transduced cell, population of cells and/or composition in a subject.

Another aspect provides a method of reducing the number of tumor cells or cancer burden in a subject in need thereof comprising administering to the subject an isolated virus, transduced cell, population of cells or composition described herein. Another aspect provides a method of treating a subject with cancer or an increased risk of cancer comprising administering to the subject an isolated virus, transduced cell, population of cells or composition described herein. In certain embodiments, the method further comprises monitoring cancer progression.

In certain embodiments, the cancer is a solid tumor. In other embodiments, the cancer is leukemia, optionally ALL, AML, CML or CLL.

A further aspect provides a method of inducing or enhancing an immune response in a subject optionally with cancer or an increased risk of cancer comprising administering t administering to the subject an isolated virus, transduced cell, population of cells or composition described herein.

In one aspect the application provides a method of inducing or enhancing a memory immune response in a subject, optionally with cancer or an increased risk of cancer, comprising administering to the subject an isolated virus, transduced cell, population of cells or composition described herein. In certain embodiments, the immune response comprises a CD4+ T cell mediated immune response. In certain embodiments, the transduced cell is growth arrested prior to administering to the subject. In one embodiment, the transduced cell is irradiated prior to administering to the subject.

Also provided, is a method of delivering IL-12 to a subject, optionally with cancer or an increased risk or cancer, optionally, for enhancing cancer treatment comprising:
generating an IL-12 secreting cell wherein IL-12 secreted per cell is above a threshold level; and
introducing an effective number of the generated IL-12 secreting cells to the subject.

Another aspect provides a method of sustaining IFNgamma levels induced by IL-12 in a host comprising:
generating an IL-12 secreting cell wherein IL-12 secreted per cell is above a threshold level; and
introducing an effective number of the generated IL-12 secreting cells to the patient.

In certain embodiments, the threshold level of IL-12 secreted is at least 1.5 fg/ml/cell/2 hrs. In other embodiments, the threshold level of IL-12 secreted is at least 1.5 pg/ml cells/2 hrs. In certain embodiments, the IL-12 secreting cell is generated by contacting the cell with a composition comprising a lentiviral delivery vector and an IL-12 expression cassette.

In certain embodiments, the cell is optionally a cancer cell, optionally derived from the subject with cancer. In certain embodiments, the cells are introduced by IP injection, subcutaneously or intradermally.

In certain embodiments, the immune response is initiated against a leukemia. In certain embodiments, the immune response is initiated substantially free of inducing or enhancing of a $CD8^+$ T cell-dependent immune response. In certain other embodiments, the immune response leads to long-term immune memory. In certain embodiments, the immune response does not induce or enhance antagonistic cytokines.

In certain embodiments, the level of IL-12 produced is above a threshold level that enhances dendritic cell maturation and/or antigen presentation.

In another aspect, the application provides use of an isolated virus, transduced cell, population of cells or composition described herein for reducing the number of tumor cells or cancer burden in a subject in need thereof.

In another aspect the application provides use of an isolated virus, transduced cell, population of cells or composition described herein for treating a subject with cancer.

In another aspect the application provides use an isolated virus, transduced cell, population of cells or composition described herein for inducing or enhancing an immune response in a subject.

In another embodiment, the application provides use an isolated virus, transduced cell, population of cells or composition described herein for inducing or enhancing a memory immune response in a subject.

In another aspect the application provides use of an IL-12 secreting cell for delivering IL-12 to a subject, optionally with cancer or an increased risk of cancer optionally for enhancing cancer treatment: generating an IL-12 secreting cell wherein IL-12 secreted per cell is above a threshold level; and isolating an effective number of the generated IL-12 secreting cells for introduction to the subject.

In another aspect the application provides use of an isolated virus, transduced cell, population of cells or composition described herein, for treating a subject in need thereof, optionally a subject with cancer or an increased risk of developing cancer.

In certain embodiments, the number of cells administered ranges from $10^5$ cells to $10^9$ cells, optionally about $10^5$, about $10^6$ cells, about $10^7$ cells, about $10^8$ cells, or about $10^9$ cells. In other embodiments, the population of cells administered ranges from $10^5$ cells to $10^9$ cells, optionally about $10^5$ cells, about $10^6$ cells, about $10^7$, cells, about $10^8$ cells, or about $10^9$ cells.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The following non-limiting examples are illustrative of the present invention:

FIG. 1c Delayed IP administration of rIL-12 therapy leads to protection. Mice were injected with $10^4$ 70Z/3-L cells on day 0. A control group (70Z/3-L) did not receive treatment (n=4). From days 0 through 5, groups of 4 or 5 mice (5 mice for days 0, 1 and 2, 4 mice for days 3, 4 and 5) started receiving injections of 20 ng rIL-12/mouse/day for 14 days. Animals were monitored and euthanized at the appearance of symptoms. Curve comparison was performed using Logrank test. All treatment groups are significantly different from the control group (p=0.0029) but are not significantly different from each other.

FIG. 4 Leukemia cell mediated IL-12 therapy leads to protection of challenged mice when only a portion of the cells are vector-transduced. Mice were injected IP with $10^6$ cells of the parent line, 70Z/3-L, and varying proportions a.) 2%, 10% and 50% of the LV12.1 secreting clone or b.) 0.1%, 0.5%, 1% and 10% of LV12.2 and LV12.3, and monitored for the appearance of symptoms.

DETAILED DESCRIPTION

Figure 1A:
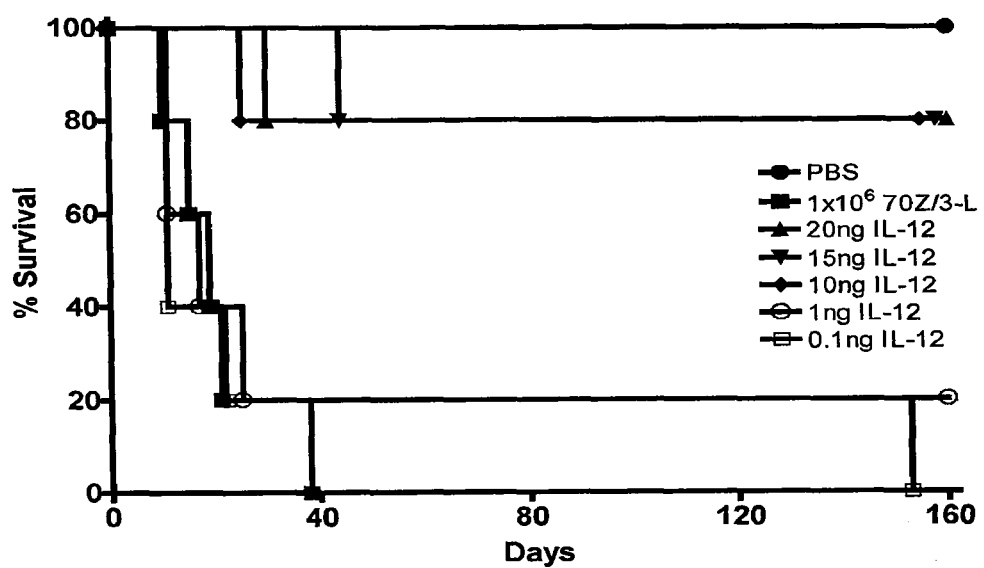
FIG. 1a IP administered rIL-12-mediated protection of mice challenged with 70Z/3-L cells. Mice were challenged with $10^6$ cells IP and received either no treatment-or injections of 0.1, 1, 10 or 20 ng/mouse/day rIL-12 for 14 days (n=5 mice for each group).

The inventors have shows that administration of low dose recombinant IL-12 (rIL-12) elicits a protective response against an established leukemia burden and that rejection is mediated by a $CD4^+$ and $CD8^+$ T cell-dependent immune response which leads to long-term immune memory without the induction of antagonistic cytokines. The inventors have compared this protocol to a cell therapy approach in which leukemic cells were transduced with a lentivirus vector (LV) engineering expression of murine IL-12 (both subunits) cDNA. Clones of the leukemic cells producing a wide range of IL-12 were established. Injection of IL-12 producing leukemic cells provoked long term and specific immunity without the induction of antagonistic mechanisms. Leukemia clearance in this instance, however, was mediated by a $CD4^+$ cellular subset alone, suggesting a qualitatively different route to immunity than that seen in systemic therapy. The inventors found that injection of as few as 1% IL-12 producing leukemic cells along with 99% untransduced leukemic cells, was sufficient to elicit protective immunity as long as each of these cells produced IL-12 above a necessary threshold. This finding may explain the failure of many human cell therapy based protocols because in these cases IL-12 production is measured on bulk populations making it impossible to know if sufficient IL-12 is being produced in the local environment influenced by the IL-12 producing cell. The average production reported in these studies is well below the threshold reported in the present disclosure.

The vector constructs, compositions, cells and methods described herein for delivering IL-12 are highly effective and are readily applied to a variety of cancers.

Definitions

The term "a cell" as used herein includes a plurality of cells.

The term "ALL" as used herein refers to acute lymphoblastic leukemia is a rapidly growing leukemia wherein the malignant hematopoietic cells are lymphoid precursor cells. Cytogenetic abnormalities occur in ~70% of cases of ALL in adults but are not associated with a single translocation event.

The term "allogenic" also referred to as "allogeneic" as used herein means cells, tissue, DNA, or factors taken or derived from a different subject of the same species. For example in the context where allogenic transduced cancer cells are administered to a subject with cancer, cancer cells removed from a patient that is not the subject, are transduced or transfected with a vector that directs the expression of IL-12 and the transduced cells are administered to the subject. The phrase "directs expression" refers to the polynucleotide comprising a sequence that encodes the molecule to be expressed. The polynucleotide may comprise additional sequence that enhances expression of the molecule in question.

The term "AML" as used herein refers to acute myeloid leukemia, a rapidly progressing disease in which too many immature non-lymphocyte white blood cells are present in the blood and bone marrow. Also called acute myelogenous leukemia, acute myeloblastic leukemia, acute nonlymphocytic leukemia, and ANLL.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. The term also includes antibodies or antibody fragments that bind to the detecting cassette polypeptides disclosed herein.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm −5° C. based on the above equation, followed by a wash of 0.2×SSC/0.1% SDS at 60° C. Moderately stringent hybridization conditions include a washing step in 3× SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "autologous" as used herein refers to cells, tissue, DNA or factors taken or derived from an individual's own tissues, cells or DNA. For example in the context where autologous transduced cancer cells are administered to a subject with cancer, cancer cells removed from the subject are transduced or transfected with a vector that directs the expression of IL-12 and the transduced cells are administered to the subject.

The phrase "cancer burden" refers to the quantum of cancer cells or cancer volume in a subject. Reducing cancer burden accordingly refers to reducing the number of cancer cells or the cancer volume in a subject.

The phrase "cancer that is characterized by periods of remission" refer to cancers that may respond to a treatment but wherein the cancer recurs at some later time suggesting that not all cancer cells were eradicated by the treatment. An example of such a cancer is CLL.

The term "cancer cell" as used herein refers to any cell that is a cancer cell or is derived from a cancer cell e.g. clone of a cancer cell.

The term "cassette" as used herein refers to a polynucleotide sequence that is to be expressed. The cassette can be inserted into a vector. The cassette optionally includes regulatory sequence to direct or modify its expression.

The phrase "cell surface protein" or "cell surface polypeptide" as used herein refers to a polypeptide that is expressed, in whole or in part on the surface of a cell. This optionally includes polypeptide fragments that are presented on cells as well as polypeptides or fragments thereof that are naturally found on the surface of a cell. In the context of a cell modified to express a vector construct comprising a detection cassette polypeptide, wherein the detection cassette polypeptide is a cell surface polypeptide, the cell surface marker need not be native to the cell it is being expressed on.

The term "CLL" refers to chronic lymphocytic leukemia, a slow growing type of leukemia. CLL is the most common leukemia of adults with an expectation of ~16500 cases in North America in 2008. Remissions can be achieved with purine analogues and monoclonal antibody therapy however the diseases invariable progresses. CLL is also referred to as chronic lymphoblastic leukemia. B-CLL is a subset of CLL.

The term "clinical grade vector" as used herein refers to a vector manufactured using near-GMP or GMP procedures and quality assurance tested.

The term "CML" refers to chronic myeloid leukemia, a slowly progressing leukemia wherein excessive white blood cells are made in the bone marrow. The hallmark of this disease is the reciprocal translocation between chromosomes 9 and 22 leading to the formation of the Bcr-Abl oncogene. This is manifested by a rapid expansion of bone marrow-derived hematopoietic cells of the myeloid lineage. CML is also referred to as chronic myelogenous leukemia, and chronic granulocytic leukemia.

A "conservative amino acid substitution" as used herein, is one in which one amino acid residue is replaced with another amino acid residue without abolishing the protein's desired properties. Conservative amino acid substitutions are known in the art. For example, conservative substitutions include substituting an amino acid in one of the following groups for another amino acid in the same group: alanine (A), serine (S), and threonine (T); aspartic acid (D) and glutamic acid (E); asparagine (N) and glutamine (Q); arginine (R) and lysine (L); isoleucine (I), leucine (L), methionine (M), valine (V); and phenylalanine (F), tyrosine (Y), and tryptophan (W).

The term "detection cassette" as used herein refers to a polynucleotide that directs expression of a molecule that is useful for enriching, sorting, tracking and/or killing cells in which it is expressed. The detection cassette encodes a polypeptide that is expressed in the transduced or transfected cell and can as a result be used to detect and/or isolate transduced or transfected cells. The detection cassette is optionally used to determine the efficiency of cell transduction or transfection.

As used herein, the phrase "effective amount" or "therapeutically effective amount" or a "sufficient amount" of composition, vector construct, virus or cell of the present application is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, it is an amount of the composition, vector construct, virus or cell sufficient to achieve a treatment response as compared to the response obtained without administration of the composition, vector construct, virus or cell The amount of a given compound of the present application that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, virus or cell of the present disclosure is an amount which results in a beneficial or desired result in a subject as compared to a control. As defined herein, a therapeutically effective amount of a composition, vector construct, virus or cell of the present disclosure may be readily determined by one of ordinary skill by routine methods known in the art. Dosage regime may be adjusted to provide the optimum therapeutic response.

The term "hybridize" refers to the sequence specific non-covalent binding interaction with a complementary nucleic acid.

An "immune modulatory cassette" as used herein, means a polynucleotide that directs expression of a molecule or polypeptide that enhances the anti-tumor effect of an IL-12 transduced cell. One class of immune regulatory molecules is cytokines. Also included are compounds that inhibit molecules that antagonize IL-12 response. For example, IL-10 can inhibit IL-12, compounds that inhibit the antagonistic effect of IL-10 would positively modulate the immune response.

The term "immune response" as used herein can refer to activation of either or both the adaptive and innate immune system cells such that they shift from a dormant resting state to a state in which they are able to elaborate molecules typical of an active immune response.

The phrase "inducing an immune response" as used herein refers to a method whereby an immune response is activated. The phrase "enhancing an immune response" refers to augmenting an existing but immune response.

The term "increased risk of cancer" as used herein means a subject that has a higher risk of developing a particular cancer than the average risk of the population. A subject may have a higher risk due to previously having had said particular cancer and or having a genetic risk factor for said particular cancer.

The term "kills" with respect to transfected or transduced cells refers to inducing cell death through any of a variety of mechanisms including apoptosis, necrosis and autophagy. For example an agent that is cytotoxic kills the cells.

The term "leukemia" as used herein refers to any cancer or precancerous syndrome that initiates in blood forming tissues such as the bone marrow. A number of leukemias have been characterized including ALL, AML, CLL, and CML. Delivery of a LV/IL-12 construct to engineer IL-12 expression in dendritic cells or other efficient antigen-presenting cells could also be effective in a pre-cancerous state if dominant tumor-associated antigens had been identified for the future cancer in that case and the host immune response re-directed against that antigen.

The term "polynucleotide" and/or "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "polypeptide" as used herein refers to a sequence of amino acids consisting of naturally occurring residues, and non-naturally occurring residues.

The term "promoter" as used herein refers to a recognition site on DNA that is bound by an RNA polymerase. The polymerase drives transcription of the transgene.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

The term "subject" as used herein includes all members of the animal kingdom including mammals, suitably humans including patients.

The term "subject in need thereof" refers to a subject that could benefit from the method, and optionally refers to a subject with cancer, such as leukemia, or optionally a subject with increased risk of cancer, such as a subject previously having cancer, a subject with a precancerous syndrome or a subject with a strong genetic disposition.

The term "transduction" as used herein refers to a method of introducing a vector construct or a part thereof into a cell. Wherein the vector construct is comprised in a virus such as for example a lentivirus, transduction refers to viral infection of the cell and subsequent transfer and integration of the vector construct or part thereof into the cell genome.

The term "treating" or "treatment" as used herein means administering to a subject a therapeutically effective amount of the compositions, cells or vector constructs of the present application and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies.

The term "vector construct" as used herein means a recombinant polynucleotide comprising a vector alternatively referred to as a vector backbone and at least one coding cassette. A vector construct is optionally comprised in a virus, such as a lentivirus. The term "vector" has used herein refers to a means by which polynucleotides can be introduced into a cell or host.

Vector Constructs and Virus

The application provides in one aspect a vector construct or virus such as a lentivirus comprising a delivery vector and and IL-12 expression cassette. In one embodiment the delivery vector is a lentivirus or lentiviral vector (LV) backbone.

Interleukin-12 (IL-12) Expression Cassette

Interleukin-12 is a heterodimeric cytokine with multiple biological effects on the immune system. It is composed of two subunits, p35 and p40, both of which are required for the secretion of the active form of IL-12, p70. Interleukin-12 acts on dendritic cells (DC), leading to increased maturation and antigen presentation, which can allow for the initiation of a T cell response to tumor specific antigens.

In one embodiment the IL-12 expression cassette comprises a polynucleotide that directs expression of IL-12 polypeptide. Any IL-12 polypeptide including variants and derivatives of known IL-12 molecules can be used. In a preferred embodiment, the IL-12 is human IL-12. In another embodiment, the IL-12 is murine IL-12.

In one embodiment the polynucleotide comprises the sequence of both IL-12 subunits, p35 and p40, separated by an RES sequence which permits expression of multiple transgenes from a single transcript. In other embodiments, the polynucleotide directs expression of an IL-12 fusion polypeptide that retains IL-12 activity. In one embodiment, the polynucleotide that directs the expression of IL-12 comprises a cDNA encoding a human IL-polypeptide fusion obtained from InVivoGen (pORF with IL-12elasti(p40::p35)). In one embodiment, the polynucleotide directs the expression of an IL-12 polypeptide comprising all or part of SEQ ID NO:4 or 5, and/or a variant of a fragment thereof that retains IL-12 activity. In another embodiment, the polynucleotide directs expression of an IL-12 fusion polypeptide that has at least 70%, 70-80%, 80-90%, 90-95%, 95-99.9% or more to the IL-12 portion of SEQ ID NO:4 or 5 and retains IL-12 activity. IL-12 activity is determined for example by assessing activation of the IL-12 receptor in a cell based assay.

A person skilled in the art will understand that non-critical residues can be deleted, and or mutated without effect on IL-12. Polynucleotides directing expression of IL-12 polypeptide analogs are also contemplated.

Delivery Vectors

It will be appreciated by one skilled in the art that a variety of delivery vectors and expression vehicles are usefully employed to introduce a modified DNA molecule into a cell. Vectors that are useful comprise lentiviruses, oncoretroviruses, expression plasmids, adenovirus, and adeno-associated virus. Other delivery vectors that are useful comprise herpes simplex viruses, transposons, vaccinia viruses, human papilloma virus, Simian immunodeficiency viruses, HTLV, human foamy virus and variants thereof. Further vectors that are useful comprise spumaviruses, mammalian type B retroviruses, mammalian type C retroviruses, avian type C retroviruses, mammalian type D retroviruses, HTLV/BLV type retroviruses, and lentiviruses.

Vectors such as those listed above have been employed to introduce DNA molecules into cells for use in gene therapy. Examples of vectors used to express DNA in cells include vectors described in: Kanazawa T, Mizukami H, Okada T, Hanazono Y, Kume A, Nishino H, Takeuchi K, Kitamura K, Ichimura K, Ozawa K. Suicide gene therapy using AAV-HSVtk/ganciclovir in combination with irradiation results in regression of human head and neck cancer xenografts in nude mice. Gene Ther. 2003 January; 10(1):51-8. Fukui T, Hayashi Y, Kagami H, Yamamoto N, Fukuhara H, Tohnai I, Ueda M, Mizuno M, Yoshida J Suicide gene therapy for human oral squamous cell carcinoma cell lines with adeno-associated virus vector. Oral Oncol. 2001 April; 37(3):211-5.

Retroviral Vectors

In one embodiment, the delivery vector is a retroviral vector. In a further embodiment, the delivery vector is a lentiviral vector. Lentiviral vectors (LVs), a subset of retroviruses, transduce a wide range of dividing and non-dividing cell types with high efficiency, conferring stable, long-term expression of the transgene[25-27].

The use of lentivirus-based gene transfer techniques relies on the in vitro production of recombinant lentiviral particles carrying a highly deleted viral genome in which the transgene of interest is accommodated. In particular, the recombinant lentivirus are recovered through the in trans coexpression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, incapsidation, and expression, in which the sequences to be expressed are inserted.

In one embodiment the lentiviral vector comprises one or more of a 5'-Long terminal repeat (LTR), HIV signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR (SIN-LTR). The lentiviral vector optionally comprises a central polypurine tract (cPPT; SEQ ID NO: 2) and a woodchuck hepatitis virus post-transcriptional regulatory element (WPRE; SEQ ID NO: 3). In a further embodiment, the lentiviral vector comprises a pHR' backbone. In certain embodiments, the pHR' back bone comprises for example as provided below.

In one embodiment the Lentigen lentiviral vector described in Lu, X. et al. Journal of gene medicine (2004) 6:963-973 is used to express the DNA molecules and/or transduce cells.

In one embodiment the lentiviral vector comprises a 5'-Long terminal repeat (LTR), HIV signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR (SIN-LTR). It will be readily apparent to one skilled in the art that optionally one or more of these regions is substituted with another region performing a similar function.

In certain embodiments the IL-12 is required to be expressed at sufficiently high levels. Transgene expression is driven by a promoter sequence. Optionally, the lentiviral vector comprise a CMV promoter. In another embodiment, the promoter is Elongation factor (EF) 1-alpha promoter. A person skilled in the art will be familiar with a number of promoters that will be suitable in the vector constructs described herein.

Enhancer elements can be used to increase expression of modified DNA molecules or increase the lentiviral integration efficiency. In one embodiment the lentiviral vector further comprises a nef sequence. In a preferred embodiment the lentiviral further comprises a cPPT sequence which enhances vector integration. The cPPT acts as a second origin of the (+)-strand DNA synthesis and introduces a partial strand overlap in the middle of its native HIV genome. The introduction of the cPPT sequence in the transfer vector backbone strongly increased the nuclear transport and the total amount of genome integrated into the DNA of target cells. In an alternate preferred embodiment, the lentiviral vector further comprises a Woodchuck Post-transcriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cells. The addition of the WPRE to lentiviral vector results in a substantial improvement in the level of transgene expression from several different promoters, both in vitro and in vivo. In a further preferred embodiment, the lentiviral vector comprises both a cPPT sequence and WPRE sequence. In yet a further embodiment, the lentiviral vector comprises a sequence having at least 70%, 70-80%, 80-90%, 90-95%, 95-99.9% or more sequence identity to SEQ ID NO:2 and/or SEQ ID NO:3. The vector also comprises in an alternate embodiment an internal ribosome entry site (IRES) sequence that permits the expression of multiple polypeptides from a single promoter.

In addition to IRES sequences, other elements which permit expression of multiple polypeptides are useful. In one embodiment the vector comprises multiple promoters that permit expression more than one polypeptide. In another embodiment the vector comprises a protein cleavage site that allows expression of more than one polypeptide. Examples of protein cleavage sites that allow expression of more than one polypeptide comprise those listed in the following articles which are incorporated by reference: Retroviral vector-mediated expression of HoxB4 in hematopoietic cells using a novel coexpression strategy. Klump H, Schiedlmeier B, Vogt B, Ryan M, Ostertag W, Baum C. Gene Ther. 200;8(10):811-7; A picornaviral 2A-like sequence-based tricistronic vector allowing for high-level therapeutic gene expression coupled to a dual-reporter system Mark J. Osborn, Angela Panoskaltsis-Mortari, Ron T. McElmurry, Scott K. Bell, Dario A. A. Vignali, Martin D. Ryan, Andrew C. Wilber, R. Scott McIvor, Jakub Tolar and Bruce R. Blazar. Molecular Therapy 2005; 12 (3), 569-574; Development of 2A peptide-based strategies in the design of multicistronic vectors. Szymczak A L, Vignali D A. Expert Opin Biol Ther. 2005; 5(5):627-38; Correction of multi-gene deficiency in vivo using a single 'self-cleaving' 2A peptide-based retroviral vector. Szymczak A L, Workman C J, Wang Y, Vignali K M, Dilioglou S, Vanin E F, Vignali D A. Nat Biotechnol. 2004; 22(5):589-94. It will be readily apparent to one skilled in the art that other elements that permit expression of multiple polypeptides which identified in the future are useful and may be utilized in the vectors of the invention.

In certain embodiments, the lentiviral vector is a clinical grade vector.

Viral Regulatory Elements

The viral regulatory elements are components of delivery vehicles used to introduce nucleic acid molecules into a host cell. The viral regulatory elements are optionally retroviral regulatory elements. For example, the viral regulatory elements may be the LTR and gag sequences from HSC1 or MSCV. The retroviral regulatory elements may be from lentiviruses or they may be heterologous sequences identified from other genomic regions.

One skilled in the art would also appreciate that as other viral regulatory elements are identified, these may be used with the nucleic acid molecules of the invention.

Detection Cassette

In certain embodiments, the vector construct comprises a detection cassette. The detection cassette comprises a polynucleotide that directs expression of a molecule that is useful for enriching, sorting, tracking and/or killing cells in which it is expressed. The detection cassette encodes a polypeptide that is expressed in the transduced or transfected cell and can as a result be used to detect and/or isolate transduced or transfected cells. The detection cassette is optionally used to determine the efficiency of cell transduction or transfection.

In one embodiment, the detection cassette encodes a polypeptide that protects from a selection drug such as neomycin phosphotransferase or G418. In another embodiment, the detection cassette encodes a fluorescent protein such as GFP. Other fluorescent proteins can also be used. In a further embodiment, the detection cassette is a cell surface marker such as CD19, truncated CD19, CD20, human CD24, murine HSA, human CD25 (huCD25), a truncated form of low affinity nerve growth factor receptor (LNGFR), truncated CD34 or erythropoietin receptor (EpoR). In certain embodiments the detection cassette polypeptide is substantially overexpressed in transduced cells such that these cells are preferentially targeted. In other embodiments, the detection cassette polypeptide is not appreciably expressed on the cell type to be transduced or transfected.

As described below, the detection cassette polypeptide can be used to isolate transduced cells by methods such as flow cytometry.

In one embodiment, the detection cassette comprises a CD19 molecule or fragment thereof. In another preferred embodiment the construct comprises a detection polynucleotide incorporated into pHR'-cppt-EF-IRES-W-SIN, pHR'-cppt-EF-huCEA-IRES-hCD19-W-SIN or pHR'-cppt-EF-HER/neuIRES-hCD19-W-SIN. Additionally it will be readily apparent to one skilled in the art that optionally one or more of these elements can be added or substituted with other regions performing similar functions.

Immune Modulatory Cassette

Enhanced antitumor effect is obtainable with the use of specific immune modulatory molecules. One class of immune regulatory molecules is cytokines. Cytokines are integral to both the innate and acquired immune systems. They can alter the balance of cellular and humoral responses, alter class switching of B lymphocytes and modify innate responses.

In one embodiment, the immune modulatory cassette comprises a polynucleotide that encodes a polypeptide that modulates an immune cell, optionally a dendritic cell or a T cell, optionally a CD4+ T cell.

In one embodiment, the immune modulatory molecule useful for promoting anti-tumor effect is RANKL. RANKL is a molecule that extends the lifespan of DCs in an autocrine fashion. CD40L which enhances the stimulatory capacity of DCs, is also useful for promoting the anti-tumor effect of DC and tumor cell vaccines. In addition a number of other cytokines are useful including IL-2, IL-7, IL-15, IL-18, and IL-23. A person skilled in the art would recognize that other immune modulatory molecules, including molecules that promote APC function are suitable for use in constructs of the present application.

In another embodiment, the immune modulatory cassette comprises a polynucleotide that encodes or directs expression of a molecule that inhibits IL-12 down modulation, for example inhibits IL-10. In one embodiment, the molecule is a dominant negative IL-10 polypeptide. In another embodiment the molecule is a small molecule inhibitor. In another embodiment, the molecule is a siRNA or shRNA molecule that knocks down IL-10 gene expression.

Safety Components

The Cell Surface Protein—Use of Immunotoxin to Kill Transduced Cells

In certain embodiments of the invention, a cell surface protein (marker) herein referred to as a detection cassette, such as CD19, CD20 HSA, truncated LNGFR, CD34, CD24 or CD25 is delivered into target cells which further selectively clears these cells in vitro and in vivo by administering an immunotoxin (antibody conjugated to a toxin) directed against the cell surface protein. The term "immunotoxin" as used herein means an antibody or fragment thereof that is cytotoxic and/or an antibody or fragment there of that is fused to a toxic agent. Immunotoxins are described in this application and known in the art, for example, in US patent application no. 20070059275.

Many immunotoxins are approved for use in humans. In one embodiment the immunotoxin is a murine anti-Tac (AT) monoclonal antibody19 fused to saporin (SAP)[100] a toxin that irreversibly damages ribosomes by cleaving adenine molecules from ribosomal RNA.21 The inventors have demonstrated both in vitro and in vivo that the AT-SAP (ATS) complex specifically target and kill retrovirally transduced cells that express huCD25. Use of immunotoxins to kill transduced cells are described in CA application Vector Encoding Therapeutic Polypeptide and Safety Elements to Clear Transduced Cells, filed Mar. 27, 2007 which is incorporated herein by reference.

Activator Polynucleotides

Other safety components that can be introduced into the vector constructs disclosed are described in U.S. application Ser. No. 11/559,757, THYMIDYLATE KINASE MUTANTS AND USES THEREOF and U.S. application Ser. No. 12/052,565 which are incorporated herein by reference. In one embodiment, the lentiviral construct further comprises an activator polynucleotide encoding a polypeptide that converts a prodrug to a drug, optionally a modified tmpk polynucleotide. In one embodiment, the activator polynucleotide comprises a tmpk polynucleotide with at least 80% sequence identity to a modified tmpk polynucleotide, optionally the sequences listed below.

The safety facet of suicide gene therapy relies on efficient delivery and stable, consistent expression of both the therapeutic and the safety component genes.

Expression Cassette Variants and Analogs

In the context of a polypeptide, the term "analog" as used herein includes any polypeptide having an amino acid residue sequence substantially identical to any of the wild type polypeptides expressed by the expression cassette for example, IL-12 or mutant IL-12, in which one or more residues have been conservatively substituted with a functionally similar residue and which displays the ability to activate in the context of IL-12, the IL-12 receptor similar to wild-type IL-12 or to IL-12 mutants. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

In the context of a polypeptide, the term "derivative" as used herein refers to a polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the wild type sequence, so long as the requisite activity is maintained.

The methods of making recombinant proteins are well known in the art and are also described herein.

The nucleic acids described herein can also comprise nucleotide analogs that may be better suited as therapeutic or experimental reagents. The nucleic acid can also contain groups such as reporter groups, a group for improving the pharmacokinetic properties of an nucleic acid.

The nucleic acid molecules may be constructed using chemical synthesis and enzymatic ligation reactions using procedures known in the art. The nucleic acid molecules of the invention or a fragment thereof, may be chemically synthesized using naturally occurring nucleotides or variously modified nucleotides designed to increase the biological stability of the molecules.

Isolated Virus

The retroviral and lentiviral constructs are in one embodiment, packaged into viral particles. Methods for preparing virus are known in the art and described herein. In one embodiment, the application provides an isolated virus, optionally a lentivirus comprising the vector construct.

Methods of isolating virus are also known in the art and further described herein.

Methods of Expressing IL-12 in Cells and Cell Isolation

In one aspect, methods for expressing IL-12 in cells at or above a threshold level are provided. Accordingly in one aspect, the application provides a method of expressing IL-12 in a cell above a threshold level.

The polynucleotides may be incorporated into an appropriate expression vector which ensures good expression of the IL-12 and/or other expression cassettes herein described. For example, vectors described herein are suitable.

Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule and regulatory sequences selected on the basis of the host cells to be used for expression, which is operatively linked to the nucleic acid molecule. Operatively linked or operably linked is intended to mean that the nucleic acid is linked to regulatory sequences in a manner which allows expression of the nucleic acid.

The application therefore includes a recombinant expression vector containing a nucleic acid molecule disclosed herein, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

Recombinant expression vectors can be introduced into host cells to produce a transformed host cell. The terms "transformed with", "transfected with", "transformation" "transduced" and "transfection" are intended to encompass introduction of nucleic acid (e.g. a vector or vector construct) into a cell by one of many possible techniques known in the art. The phrase "under suitable conditions that permit transduction or transfection of the cell" refers to for example for ex vivo culture conditions, such as selecting an appropriate medium, agent concentrations and contact time lengths which are suitable for transfecting or transducing the particular host. Suitable conditions are known in the art and/or described herein. The term "transformed host cell" or "transduced host cell" as used herein is intended to also include cells capable of glycosylation that have been transformed with a recombinant expression vector disclosed herein. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks. Suitable methods for transducing cells are known in the art and are also described herein.

Vector constructs are introduced into cells that are used for transplant or introduced directly in vivo in mammals, preferably a human. The vector constructs are typically introduced into cells ex vivo using methods known in the art. Methods for introducing vector constructs comprise transfection, infection, electroporation. These methods optionally employ liposomes or liposome like compounds. Introduction in vivo optionally includes intravenous injection and/or intratumoral injection. These methods are described more fully elsewhere In certain embodiments, the cell is contacted with a composition vector construct and/or isolated virus described herein, for example an isolated virus comprising a lentiviral vector and a IL-12 expression cassette, under conditions that permit transduction or transfection of the cell. Methods of transducing cells are well known in the art.

In one embodiment, the method of expressing IL-12 in a cell comprises contacting the cell with a composition and/or vector construct described herein, for example comprising a lentiviral vector and an IL-12 expression cassette, under conditions that permit transduction or transfection of the cell.

In other embodiments, the cells are optionally transduced with retroviral constructs that drive expression of IL-12 and/or additional expression cassettes described herein. Methods of transducing cells are well known in the art. Methods of transducing cells with lentiviral vectors are also described herein.

In another embodiment, the method further comprises isolating the transduced cell or a population of transduced cells.

After transduction or transfection with vector constructs comprising an IL-12 expression cassette, and/or detection cassette polynucleotide, cells expressing these molecules are optionally isolated by a variety of means known in the art. In certain embodiments, the cells are isolated by cell sorting or flow cytometry using an antibody to the detection cassette encoded selection marker. Additionally cell sorting is useful to isolate modified cells where the detection cassette is a fluorescent protein such as EGFP.

In one embodiment cells are isolated from the transduction or transfection medium and/or the viral preparation. For example the cells may be spun down and/or washed with a buffered saline solution. Accordingly, the cells can comprise a population of cells comprising transduced and untransduced cells. In certain embodiments, the population of cells comprises at least 1%, 2-5%, 5-10%, 10-15%, 15-20%, 20-25%, 25-30%, 30-40%, 40-50%, 50-60%, 60-70%, 70-80%, 80-90%, 90-95%, 95-99% or more than 99% IL-12 transduced or transfected cells.

Cells expressing polynucleotides of the invention are, in an alternate embodiment, isolated using magnetic sorting. Additionally, cells may be isolated by drug selection. In one embodiment, a vector comprising a drug resistance gene and a polynucleotides of the invention is introduced into cells. Examples of drug resistance genes include, but are not limited to, neomycin resistance gene, blasticidin resistance gene (Bsr), hygromycin resistance gene (Hph), puromycin resistance gene (Pac), Zeocin resistance gene (Sh ble), FHT, bleomycin resistance gene and ampicillin resistance gene. After transduction or transfection, modified cells including the drug resistance gene are selected by adding the drug that is inactivated by the drug resistance gene. Cells expressing the drug resistance gene survive while non-transfected or non-transduced cells are killed. A person skilled in the art would be familiar with the methods and reagents required to isolate cells expressing the desired polynucleotides.

In a further embodiment, the transduced cells are growth arrested. Several methods can be used to growth arrest cells. In one embodiment, the transfected or transduced cells are growth arrested by irradiation. The term "growth arrested" refers to being inhibited for cell division. A person skilled in the art would recognize that the suitable irradiation dose to growth arrest a cell or population of cells may vary upon the cell type and/or number of cells. In one embodiment, the dose is about 75-150 G. In another embodiment, for AML the dose of radiation is about 75 G.

Host Cells

The disclosure also provides in one aspect a cell (including for example an isolated cell in vitro, a cell in vivo, or a cell treated ex vivo and returned to an in vivo site) expressing and/or secreting IL-12 above a threshold limit. In one embodiment, the cell is transduced with a vector construct, virus or composition described herein.

Cells transfected with a nucleic acid molecule such as a DNA molecule, or transduced with the nucleic acid molecule such as a DNA or RNA virus vector, are optionally used, for example, in bone marrow or cord blood cell transplants according to techniques known in the art.

Any cell may be used for transduction with the vector constructs described herein to obtain a cell expressing IL-12 above the threshold level. In one embodiment, the cell is a cancer cell. In one embodiment, the cancer cell is a primary cancer cell. In a further embodiment, the primary cancer cell is derived from a subject. The cancer cell is optionally an allogenic or autologous cell. The cancer cell to be transduced is optionally derived from, propogated from or cloned from a cancer cell obtained from a subject. The cancer cell is in one embodiment obtained from the subject by biopsy. Alternatively, the cancer cell can be obtained from a blood sample, for example in the case of a leukemia, where the disease cell type is present in the peripheral blood. Methods for isolating cancer cells from a blood sample are known in the art and/or described herein.

Any cancer cell that can be transduced or transfected is a suitable host for transduction or transfection using a composition or vector construct of the application. In one embodiment the cancer cell is a leukemia cell. In one embodiment the leukemia cell is an acute lymphoblastic leukemia (ALL) cell, a chronic lymphoblastic leukemia (CLL) cell, chronic myeloid leukemia (CML) cell, or acute myeloid leukemia (AML) cell. In certain embodiments, the cancer cell is derived from a cancer that is characterized by or can exhibit periods of remission. In certain embodiments, the cancer cell is a metastatic cancer cell. In other embodiments, the cancer cell is a lymphoma, myeloma, tumor of the lung, ovary, prostate, breast, melanoma, colon, bladder, liver, pancreas, thyroid, head or neck cancer cell. The immune system is able to seek out cells residing in nearly all parts of the body and therefore all cancers could be susceptible to this approach including: leukemias, lymphoma, myelomas, tumors of the lung, ovary, prostate, breast, melanoma, colon, bladder, liver, pancreas, thyroid, head and neck.

Cell lines are optionally transduced or transfected. For example human T cell leukemia Jurkat T cells, human erythro-leukemic K562 cells, CES1, OCIAML1, OCIAML2, and Raji cells are optionally transduced or transfected with polynucleotides of the described herein. Raji is a burkitts lymphoma line, OCI AML 1 and 2 are acute meylogenous leukemia lines, CES1 is a chronic myelongenous leukemia A cancer cell expresses tumor associated antigens and introduction of IL-12 and optionally immune modulatory molecules that augment the immune response when the tumor cell is introduced into the subject as demonstrated by the inventors. In one embodiment, the tumor cell is transduced with a lentiviral construct comprising an IL-12 cassette and optionally an immune modulatory cassette, wherein the immune modulatory cassette comprises a polynucleotide that encodes a molecule that induces DC cells and/or T cells. Cancer cells are attractive vehicles for expressing IL-12 as the immune response is self limiting. Transduced cancer cells elicit an immune response that leads to the eradication of the initiating cell. IL-12 levels are thereby self-limited.

Compositions and vector constructs described herein are usefully introduced into any cell type ex vivo. The compositions and vector constructs described herein may also be introduced into any cell type in vivo.

Threshold Level

The inventors have demonstrated that a minimum number of cancer cells expressing at least a threshold amount of IL-12 can induce and/or enhance an immune response in a subject. The immune response in some embodiments, leads to loss of non-transduced cancer cells.

In one embodiment, the threshold level is at level is at least 1500 pg/mL/$10^6$ cells/2 hrs of IL-12. In another embodiment, the threshold level is at least 1500-2500 pg/mL/$10^6$ cells/2 hrs, 2500-5000 pg/mL/$10^6$ cells/2 hrs, 5000-7500 pg/mL/$10^6$ cells/2 hrs, 7500-10000 pg/mL/$10^6$ cells/2 hrs, 10000-12500 pg/mL/$10^6$ cells/2 hrs, 12500-15000 pg/mL/$10^6$ cells/2 hrs, 15000-17500 pg/mL/$10^6$ cells/2 hrs, 17500-20000 pg/mL/$10^6$ cells/2 hrs or at least 20000 pg/mL/$10^6$ cells/2 hrs of IL-12.

In another embodiment, a population of cells comprises transduced cells that secrete at least about 1500-2500 pg/mL/$10^6$ cells/2 hrs, 2500-5000 pg/mL/$10^6$ cells/2 hrs, 5000-7500 pg/mL/$10^6$ cells/2 hrs, 7500-10000 pg/mL/$10^6$ cells/2 hrs, 10000-12500 pg/mL/$10^6$ cells/2 hrs, 12500-15000 pg/mL/$10^6$ cells/2 hrs, 15000-17500 pg/mL/$10^6$ cells/2 hrs, 17500-20000 pg/mL/$10^6$ cells/2 hrs or at least 20000 pg/mL/$10^6$ cells/2 hrs of IL-12. In other embodiments, the population of cells comprise transduced cells that secrete at least about 20,000-40,000 pg/mL/$10^6$ cells/2 hrs of IL-12. A person skilled in the art would understand that each cell would secrete varying amounts of IL-12. The population may include cells secreting less or more than the numbers herein listed or a given threshold. The transduced cells as a whole comprise a sufficient number of IL-12 secreting cells, secreting IL-12 above the threshold level such that DC are activated.

The population of cells can comprise transduced and non-transduced and/or transfected and non-transfected cells. In one embodiment, at least 0.5%. 1%, 2-5%, 5-10%, 10-15%, 15-20%, 20-25%, 25-30%, 30-40%, 40-50%, 50-60%, 60-70%, 70-80%, 80-90%, 90-95%, 95-99% or more than 99% of cells in the population of cells are transduced or transfected and/or express IL-12.

In a preferred embodiment, the population of cells comprises 1% transduced cells secreting 20, 000 pg/$10^6$ cells/2 hrs.

The level of IL-12 expression can be determined by a number of methods including methods known in the art and methods described herein. For example IL-12 levels can be determined by ELISA, cytokine bead assay, intracellular staining, HPLC and MS/MS, or ELISPOT.

Compositions

The application describes compositions comprising an IL-12 expression cassette and a lentiviral vector as described herein. The vector is for providing a coding nucleic acid molecule (eg. the expression cassette) to a subject such that expression of the molecule in the cells provides the biological activity of the polypeptide encoded by the coding nucleic acid molecule to those cells. A coding nucleic acid as used herein means a nucleic acid or polynucleotide that comprises nucleotides which specify the amino acid sequence, or a portion thereof, of the corresponding protein. A coding sequence may comprise a start codon and/or a termination sequence.

In other embodiments, the composition comprises cells modified with the vector constructs described herein. Such modified cells can be administered intravenously using methods known in the art i.p., i.v., intratumorally, stereotactic injections to a variety of sites, direct injections, intramuscularly, etc.

Pharmaceutical Compositions

The pharmaceutical compositions of this invention used to treat patients having diseases, disorders or abnormal physical states could include an acceptable carrier, auxiliary or excipient.

The pharmaceutical compositions are optionally administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors are also useful.

Dosages to be administered depend on patient needs, on the desired effect and on the chosen route of administration. The expression cassettes are optionally introduced into the cells or their precursors using ex vivo or in vivo delivery vehicles such as liposomes or DNA or RNA virus vectors. They are also optionally introduced into these cells using physical techniques such as microinjection or chemical methods such as coprecipitation.

The pharmaceutical compositions are typically prepared by known methods for the preparation of pharmaceutically acceptable compositions which are administered to patients, and such that an effective quantity of the nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents is well known to those skilled in the art. The composition could include a targeting agent for the transport of the active compound to specified sites within cells.

Methods of Inducing/Enhancing Immune Responses and Methods of Treatments

The methods disclosed herein are useful for inducing and enhancing an immune response in a subject. In one embodiment, the subject has cancer. In another embodiment, the subject is in remission. In a further embodiment, the subject has an increased risk of cancer.

In one embodiment, the application provides a method of inducing or enhancing an immune response in a subject comprising administering a transduced cell or population of cells described herein or a composition comprising said cells.

In another embodiment, the application provides a method of inducing or enhancing a memory immune response in a subject.

In one embodiment, the immune response induced or enhanced is a CD4+ T cell mediated immune response.

The application also provides a method of delivering IL-12 to a subject for enhancing cancer treatment comprising:
  generating an IL-12 secreting cell wherein IL-12 secreted per cell is above a threshold level; and
  introducing an effective number of the generated IL-12 secreting cells to the subject.

In another embodiment, the application provides a method of of sustaining IFNgamma levels induced by IL-12 in a host comprising:
  generating an IL-12 secreting cell wherein IL-12 secreted per cell is above a threshold level; and
  introducing an effective number of the generated IL-12 secreting cells to the subject.

In one embodiment, transduced cells, a population of cells and/or a composition comprising said cells are administered to a subject In another embodiment, the cells, population of cells and/or composition are administered with an adjuvant. For example, in one embodiment incomplete Freund's adjuvant is used. In addition, the cells, population of cells and/or composition is administered once, or repeated. For example, the cells and or population of cells are administered a second time to boost the immune response and/or increase the amount of IL-12 delivered or IFNgamma sustained.

In one embodiment, cancer cells are obtained from a subject, and genetically modified to express and/or secrete IL-12 above a threshold level. The transduced cells or population of cells comprising transduced cells is irradiated and administered to the subject. Accordingly in certain embodiments, clinical use of the modified cells is restricted to the subject from whom the cancer cell was derived.

Wherein cells additionally express an activator polynucleotide encoding a polypeptide that concerts a prodrug to a drug, for example a modified tmpk polynucleotide, cells are optionally not irradiated. Any unwanted cells can be killed upon administration of the prodrug. For example, in some cases, irradiation may negatively effect the ability of the transduced cells to induce an immune response eg irradiation may cause cell death in certain cell populations. Use of an activator polynucleotide or other mechanism to remove unwanted cells transplanted into the subject is alternatively used in such situations.

The methods disclosed herein are useful for treating a variety of cancers. The inventors have shown that leukemias of a variety of types are amenable to IL-12 treatment.

Residual disease which can lay dormant during remissions may be targeted by the method disclosed herein. The delayed disease progression of many leukemias provides a critical window of opportunity for immune-based approaches. The present immunotherapy may also rid quiescent cells such as cancer initiating "stem" cells because it does not require biochemically or genetically active targets. Further the present immunotherapy may also lead to eradicating metastatic disease.

The methods described herein are also useful to treat solid cancers. For example the methods may be used to treat melanoma, renal cancer and prostate cancer.

The cells may be introduced by a variety of routes as disclosed elsewhere including intraperitoneal injection or intravenous infusion. Alternatively, a vector construct, isolated virus or composition comprising said construct or virus can be injected intratumorally such that transduction takes place in vivo The number of cells injected or administered is in one embodiment an effective number to induce an immune response. An immune response can be detected using a number of methods known in the art including detecting host T cell recognition of tumor cells in vitro. Alternatively, an immune response can be detected by assessing cytokine profile changes. For example increased expression of IFNgamma is indicative of an immune response.

In certain embodiments, the methods further comprise monitoring cancer progression. Cancer progression can be monitored using known methods.

In one embodiment, compositions and vectors of the invention are used to treat cancer by adoptive therapy. In one embodiment, cytotoxic lymphocyte cells are expanded using LV-IL-12 transduced cells in vitro. Adoptive therapy or adoptive (immuno)therapy refers to the passive transfer of immunologically competent tumor-reactive cells into the tumor-bearing host to, directly or indirectly, mediate tumor regression. The feasibility of adoptive (immuno)therapy of cancer is based on two fundamental observations. The first of these observations is that tumor cells express unique antigens that can elicit an immune response within the syngeneic (genetically identical or similar especially with respect to antigens or immunological reactions) host. The other is that the immune rejection of established tumors can be mediated by the adoptive transfer of appropriately sensitized lymphoid cells. Clinical applications include transfer of peripheral blood stem cells following non-myeloablative chemotherapy with or without radiation in patients with lymphomas, leukemias, and solid tumors.

In one aspect of the present invention, donor T cells or stem cells (either embryonic or of later ontogeny) are transduced with vectors of the invention. Cells expressing these vectors are isolated and adoptively transferred to a host in need of treatment. In one embodiment the bone marrow of the recipient is T-cell depleted. Methods of adoptive T-cell transfer are known in the art (J Translational Medicine, 2005 3(17): doi;0.1186/1479-5876-3-17, Adoptive T cell therapy: Addressing challenges in cancer immunotherapy. Cassian Yee). This method is used to treat solid tumors and does not require targeting the vector-transduced expressing T-cells to the tumor since the modified T-cells will recognize the different MHC class molecules present in the recipient host resulting in cytotoxic killing of tumor cells.

In one embodiment, autologus DC and T cells are contacted ex vivo with IL-12 transduced cancer cells and/or expanded ex vivo and administered to a subject in need thereof with or without LV-IL-12 secreting cells.

The compositions and vectors are also useful for the reduction of cell proliferation, for example for treatment of cancer. The present disclosure also provides methods of using compositions and vectors of the disclosure for expressing IL-12 for the reduction of cell proliferation, for example for treatment of cancer.

The application also provides a method of reducing the number of tumor cells or cancer burden in a subject with cancer, or having an increased likelihood of developing cancer comprising administering a transduced cell, population of cells, or a composition comprising said cells to the subject.

In another embodiment, the application provides a method of treating a subject with cancer or an increased risk of developing cancer comprising administering a transduced cell, population of cells, or a composition comprising said cells to the subject.

Vector constructs containing the nucleic acid molecules of the disclosure and isolated viruses are typically administered to mammals, preferably humans, using techniques described below. The polypeptides produced from the nucleic acid molecules are also optionally administered to mammals, preferably humans. The invention relates to a method of medical treatment of a mammal in need thereof, preferably a human, by administering to the mammal a vector construct described herein or a cell containing the vector construct.

One aspect relates to methods for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present invention. The method may be performed ex vivo or in vivo. Gene therapy methods and compositions are demonstrated, for example, in U.S. Pat. Nos. 5,869,040, 5,639,642, 5,928,214, 5,911,983, 5,830, 880,5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector may be readily determined using empirical techniques, for example by escalating doses (see U.S. Pat. No. 5,910,488 for an example of escalating doses).

The method also relates to a method for producing a stock of recombinant virus by producing virus suitable for gene therapy comprising modified DNA encoding a gene of interest. This method preferably involves transfecting cells permissive for virus replication (the virus containing therapeutic gene) and collecting the virus produced.

Cotransfection (DNA and marker on separate molecules) may be employed (see eg U.S. Pat. No. 5,928,914 and U.S. Pat. No. 5,817,492). As well, a detection cassette or marker (such as Green Fluorescent Protein marker or a derivative) may be used within the vector itself (preferably a viral vector).

Combination Treatments

In certain embodiments, the vector constructs, transduced cells, population of cells and or compositions comprising these, are administered in combination with other therapies. For example, the the vector constructs, transduced cells, population of cells and or compositions comprising these may be administered before or after chemotherapy suitable for the cancer being treated. In other embodiments wherein the cancer is a solid cancer, the vector constructs, transduced cells, population of cells and or compositions comprising these are administered before or after surgery.

In one embodiment, cancer cells are harvested from a subject's blood before the combination treatment, optionally chemotherapy, is started. The cancer cells are then transduced with a LV-IL-12. Transduced cells are frozen for later use and administered when the subject is in remission.

Dosing

The methods provide in certain embodiments, that a composition, transduced cell, population or cells, or vector construct described herein is administered to the subject. The compositions, cells or vector constructs of the present application may be administered at least once a week in one embodiment. However, in another embodiment, the composition, transduced cell, population or cells, or vector construct may be administered to the subject from about one time per week, one time per 14 days, or 28 days. The administration may be repeated 1, 2, 3, 4, 5, 6 or more times. In another embodiment, administration is about once daily for a given treatment, for example for rIL-12 therapy. The length of the treatment period depends on a variety of factors, such as the severity of the disease, the age of the patient, the concentration and the activity of the compounds of the present application, or a combination thereof. In one embodiment, the treatment is chronic treatment and the length of treatment is 1-2 weeks, 2-4 weeks or more than 4 weeks. The treatment regimen can include repeated treatment schedules. It will also be appreciated that the effective amount or dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

The number of cells administered varies with the expression level of the transduced cell or population of cells. For example, where the IL-12 expressing cells express over 20000 pg/mL/$10^6$ cells/2 hrs IL-12, as few as 5000 or 0.5% of a population of cells comprising IL-12 expressing cells may be sufficient for the methods described herein. However where the IL-12 expressing cells express only 2000 pg/mL/ $10^6$ cells/2 hrs IL-12, greater than 100000 or 10% of a population of cells comprising IL-12 expressing cells may be needed.

In one embodiment, 1-5, 5-10, 10-20, 20-30, 30-40, 40-50, 50-60, 60-70, 70-80, 80-90, 90-100 or more than 100 ×106 cells are administered. In another embodiment, $10^6$-$10^9$ cells are administered. Where the cells produce greater than 2000 pg/ml/$10^6$ cells/2 hrs greater than 10% of the population of cells express IL-12. Wherein the cells express 20,000 pg/ml/$10^6$ cells/2 hrs, at least 0.5% of the population of cells express IL-12.

Polypeptide Production and Research Tools

A cell line (either an immortalized cell culture or a stem cell culture) transfected or transduced with a polynucleotide of the invention (or variants) is useful as a research tool to measure levels of expression of the coding nucleic acid molecule and the activity of the polypeptide encoded by the coding nucleic acid molecule.

The invention includes a method for producing a recombinant host cell capable of expressing a nucleic acid molecule of the invention comprising introducing into the host cell a vector of the invention.

The invention also includes a method for expressing a polypeptide in a host cell of the invention including culturing the host cell under conditions suitable for coding nucleic acid molecule expression. The method typically provides the phenotype of the polypeptide to the cell.

Another aspect of the invention is an isolated polypeptide produced from a nucleic acid molecule or vector of the invention according to a method of the invention.

Another aspect relates to a system or model for testing the mechanism of IL-12 mediated rejection of cancer. In one embodiment the system is an in vitro system. Understanding the underlying mechanism that leads to an effective anti-leukemia immune response is greatly facilitated by establishing in vitro assays which mimic in vivo observations. This is useful for comparing and adapting murine models to human disease. In one embodiment, the in vitro system comprises murine bone marrow derived DCs (grown for 6-9 days in GM-CSF) induced to mature (increased expression of CD80) in the presence of both spleen cells+70Z/3-IL-12 producing cells (but not with either alone). Maturation does not occur if non-transduced 70Z/3 cells are substituted for the 70Z/3-IL-12 cells. Selected populations from the spleen are added and/or removed (immature T cells, CD4$^+$ T cells, CD8$^+$ T cells, NKT cells, NK cells, DC precursors) to define the critical cell types that are required for 70Z/3-IL-12 mediated DC maturation.

In one embodiment the system comprises human leukemia cells expressing IL-12 and/or a mouse model susceptible to developing cancer to determine the mechanism by which Interleukin-12 (IL-12) provokes an immune response which, in mice, results in complete rejection of leukemia. In one embodiment, the system permits analysis of the interactions of T cells, dendritic cells (DC), leukemia cells and the cytokines that they produce in established murine in vitro and in vivo systems. In another embodiment, the system permits optimization of the parameters essential for engineering primary samples of human leukemia cells to express quantities of IL-12 above necessary thresholds established in the murine system. In a further embodiment, the system is useful to establish in vitro conditions to determine how primary human leukemia cells expressing IL-12 interact with the autologous DCs and T cells.

EXAMPLES

Example 1

Direct injection of recombinant IL-12 has shown effectiveness in some mouse models of leukemia.[9-13] while initial human trials employing this approach were less promising ([14-17] and discussed in [4]). It is well recognized in the literature that IL-12-induced anti-leukemia activity is largely mediated by the secondary secretion of IFN-γ.[13] Gollob et al., in particular, have suggested that the induction and maintenance of IL-12-induced IFN-γ was a key component of effective therapy in patients with metastatic renal cell cancer.[18] However the concomitant induction of antagonistic effects with elevated IFN-γ levels continues to pose a challenge and is the impetus for a number of groups to continue testing the efficacy of recombinant IL-12 following different dose and time protocols[7, 8, 19-21] and to evaluate the therapeutic potential of cell-based IL-12 gene therapy ([22-27] and discussed in [4, 13]) in order to overcome this.

More recent clinical trials have included approaches such as intraleukemial injection of IL-12 secreting fibroblasts and dendritic cells, methods that have proven effective in mouse models. To date, these approaches have not had a significant impact on patient survival[15-17]. Finding the reason for this disconnect is of paramount importance.

The inventors recently published a model of ALL in which one variant of the 70Z/3 murine pre-B cell leukemia line, 70Z3-L, is lethal in syngeneic mice while another variant, 70Z/3-NL, elicits a protective immune response (27). The 70Z/3-L cells, although unable to initiate immunity, were readily rejected when an immune response was first initiated against 70Z/3-NL cells. Therefore, our model is amenable to testing whether IL-12 can initiate a specific immune response, recognition of 70Z/3-L and survival of challenged animals. 70Z/3 leukemia is reminiscent of human ALL with neoplastic lesions arising in the liver, spleen, lymph nodes, bone marrow and rarely the central nervous system. Among the most common physical manifestations of the disease are ascites and splenomegaly.

Materials and Methods

Animals.

Female (C57Bl/6xDBA/2)F1 mice (referred to as BDF1), 8-12 weeks, old were purchased from the Jackson Laboratories (Bar Harbor, Me.). Mice were kept under sterile conditions in the specific pathogen free (SPF) animal facility at the Ontario Cancer Institute, Princess Margaret Hospital, Toronto, Ontario, Canada. Mice are fed an irradiated diet and autoclaved tap water. Animals are terminated by $CO_2$ asphyxiation and cervical dislocation. The Animal Care Committee of the Ontario Cancer Institute approved all experimental protocols employed.

Tumor Cells.

Leukemia Cells. 70Z/3-L leukemia cells (described in[28]), derived from $BDF_1$ mice, were maintained in IMDM with 5% heat inactivated fetal bovine serum (HYCLONE, South Logan, Utah, USA), 100 μg/mL penicillin-streptomycin or 100 μg/mL kanamycin (GIBCO-Invitrogen), and 5.5×10$^{-5}$ M β-mercaptoethanol (referred to as complete IMDM) in a humidified atmosphere at 37° C. and 5% $CO_2$. Cell concentrations were kept at 5-10×10$^5$ cells/mL.

Lentiviral Vector Construction.

Lentiviral vectors expressing IL-12 cDNA were constructed by a method similar to that described by Yoshimitsu et al[29] with modification. Plasmid pORF-mIL12 (IL-12alasti(p35::p40) Mouse (p35::p40)) (InvivoGen, San Diego, Calif.) was modified by creating EcoRI and BamHI restriction enzymes sites, upstream and downstream of the IL-12 gene respectively using a QuickChange Site-Directed Mutagenesis Kit (Stratagene, La Jolla, Calif.). This resulting construct was then digested with EcoRI/BamHI (New England Biolabs). Murine IL-12 cDNA was purified after electrophoresis on a 1% agarose gel, and then subcloned into the pHR' LV backbone downstream of the elongation factor 1 alpha (EF1α) promoter. Positive plasmid clones for pHR-cPPT-EF1α-muIL-12-WPRE (i.e. LV-muIL-12) were identified by diagnostic restriction enzyme digestion analyses and subsequent DNA sequencing (Innobiotech, Toronto, ON, Canada).

Viral Production and Transduction of the Cells.

Concentrated LVs were produced by a transient triple-transfection method using pHR-cPPT-EF1α-muIL-12-WPRE and accessory plasmids onto 293T monolayers by calcium phosphate.[30, 31] An approximate vector titre was estimated based on LV/enGFP[29] production and testing on naïve 293T cells that occurred in parallel. The murine pre-B leukemic cell line, 70Z3-L, was then transduced with an approximate multiplicity of infection (MOI) of 20. Single cell clones, obtained by limiting dilution in 96 well plates at population densities of less than 0.3 cells/well, were then quantitated for IL-12 production/$10^6$ cells/mL/2 hrs using a commercially available IL-12 ELISA kit (BD Biosciences, San Jose, Calif.).

In Vivo Challenge Experiments.

In Vivo Challenge Experiments.

Leukemia cells and transduced cells were grown in complete IMDM and were washed 3 times with 30 mL of phosphate buffered saline (PBS) with $Ca^{2+}$ and $Mg^{2+}$. The cells were resuspended at 5-10×$10^6$ cells/mL in PBS and injected into the animals in a volume of 100-200 µL. Mice received IP injections that were performed on the right side of the abdomen using a 1 mL syringe with a 26-gauge needle.

Serum Collection.

Serum collection in live mice was achieved by puncturing the saphenous vein with a sterile needle and collecting the blood in a serum separator tube (BD, NJ, USA). These tubes were centrifuged at 10,000 RPM for 5 minutes, the serum was then transferred to a micro centrifuge tube and frozen at −20° C. until use.

Intraperitoneal Administration of rIL-12.

Recombinant mouse IL-12 was purchased from R&D Systems, Minneapolis, USA. Mice were injected IP with $10^6$ 70Z/3-L cells in 100-200 µL PBS on day 0 followed by daily injections of 0.1-20 ng/mouse/day rIL-12 in PBS for a period of 14 days. A secondary challenge consisted of IP injection of $10^6$ 70Z/3-L cells 70 days after primary challenge, carried out in the manner just described. For the delayed rIL-12 treatments mice received an IP injection of $10^4$ 70Z/3-L cells in 100-200 µL PBS on day 0. Thereafter groups of 4 or 5 mice received 14 successive rIL-12 IP injections of 20 ng/mouse/day but the initiation of these injections was delayed by between 0 and 5 days. The animals were monitored daily for the appearance of symptoms both during the injection period and following the end of the injections.

Intraperitoneal Administration of Leukemia Cell-Produced IL-12.

Interleukin-12 secreting cells were produced as described above. Mice were injected IP with $10^6$ transduced cells or a mixture of transduced and naïve cells in various proportions in 100-2004 PBS. A secondary challenge consisted of IP injection of $10^6$ 70Z/3-L cells or $10^6$ L1210 cells more than 110 days after primary challenge carried out in the manner just described. The animals were monitored daily for the appearance of symptoms following injection.

Challenge In-Depleted Animals.

Mice were depleted of CD4+, $CD8^+$ or both T cell subsets as well as NK cells and IFN-γ using specific antibodies. The hybridoma GK1.5 is directed against $CD4^+$ T cells, YTS169 against $CD8^+$ T cells, HB170 (R4-6A2) against IFN-γ and the hybridoma HB9419 was used to produce an isotype control antibody. All hybridomas were obtained from the American Type Culture Collection (ATCC) (Manassas, Va., USA). The lines were grown in 2.5 litres of complete IMDM or OptiMEM in Lifecell culture bags (Lifecell Tissue Culture, Baxter Corporation, Concord, Ontario, Canada) in a humidified atmosphere at 37° C. and 5% $CO_2$ until a live cell count (using trypan blue exclusion) revealed 30% dead cells in the culture. The media was then centrifuged and filtered to remove cells and cellular debris. The antibodies were purified from the media using an affinity column of packed sepharose beads (Gammabind G, Amersham Biosciences Corp, Piscataway, N.J., USA) and concentrated with Centriprep YM-30 columns (Millipore, Billerica, Mass., USA) before dialysis in PBS. NK cells were depleted using an anti-asialoGM1 antibody produced by Wako Bioproducts (Richmond, Va.). Rabbit IgG (Sigma-Aldrich) was used as a control for the anti-asialoGM1 antibody. The T cell subset and IFN-γ antibodies were injected on days −1, 3, 7, 10 and 14. The doses used were 1 mg of antibody on day −1 and 500 µg for the remaining injections. The NK cell depleting antibody was injected on days −1, 4, 9 and 14 using the recommended dilution.[32] Control isotype antibodies were injected following the same dose and schedule as their corresponding depleting antibodies. The depletion potential of the antibodies was demonstrated in vivo prior to their use in our experiments by injecting mice with a range of concentrations and subsequently examining tissues by flow cytometry to quantify cellular subsets, or examining serum for the presence of cytokines by ELISA. This experiment was conducted twice to test both model systems. In each case, cells were injected on day 0: either $10^6$ 70Z/3-L cells followed by 14 daily injections of rIL-12 (10 or 20 ng/mouse/day) or $10^6$ 70Z/3-L vector-transduced cells of the LV12.2 clonal line. Controls included mice injected with 70Z/3-L alone and mice injected with PBS alone according to the appropriate injection schedule.

Bead Assay for Cytokine Levels in the Serum.

Mice were injected IP on day 0 with $10^6$ 70Z/3-L cells in 100 µL PBS and treated daily with 100 µL preparations of PBS alone or containing low doses of rIL-12 (10 or 20 ng/mouse/day) for 14 days. Control groups included mice injected daily for 14 days with PBS in the absence of 70Z/3-L cells and rIL-12, and a group that was left entirely untreated. Alternatively, for the leukemia cell-mediated IL-12 therapy experiment, mice were injected on day 0 with $10^6$ 70Z/3-L cells in 100 µL PBS containing various proportions of the 70Z/3-L vector-transduced cell line LV12.2 (0.5%, 1% and 10%). Control groups included mice injected with 70Z/3-L cells alone or PBS alone. Serum was non-terminally collected from all groups on days 7, 10 and 20 before their daily injection by puncture of the saphenous vein as described above. All mice from the group receiving 70Z/3-L cells alone in the leukemia cell-produced IL-12 therapy model had perished by day 20 such that serum was not collected from this group. Serum samples were diluted 1/5 and stained according to the protocol provided with the Mouse Inflammation Cytometric Bead Array Kit (BD, San Diego, Calif., USA). Standards were prepared in triplicate from independent dilutions and flow cytometry was done using a FACScan (Becton Dickinson, Oakville, ON). Acquisition was performed using CellQuest software version 3.1.

Southern Blot to Determine Gene Copy Number.

The muIL-12 gene copy number of vector-transduced 70Z3-L clones was determined by Southern blot as described before.[24] Briefly, 5 pg of genomic DNA extracted from vector-transduced or naïve control 70Z3-L cells was treated with both EcoRI and HindIII (New England Biolabs) and electrophoresed onto a 0.8% agarose gel. Next the agarose gel was washed and transferred onto a positively charged nylon membrane (Bio-Rad).[25] A 746 bp fragment containing the WPRE sequence of LV-muIL-12 to be used as the hybridization probe was amplified by PCR (Forward primer; 5'-tgctccttttacgctatgtgg-3', Reverse primer; 5'-tcgt-tgggagtgaattagcc-3') employing the PCR DIG Probe Synthesis kit (Roche). Southern hybridization was performed using the DIG Luminescent Detection kit (Roche), according to the manufacturer's instructions. Serial dilutions of the LV-muIL-12 plasmid (see above) in mouse genomic DNA were used as WPRE standards. The results were analyzed using NIH image software and presented as copies/genome.

RESULTS

Intraperitoneal Administration of rIL-12 Protects Mice Challenged with 70Z/3-L.

Interleukin-12 is known to be a potent modulator of the immune response attributed with a number of anti-leukemia effects including, but not limited to, T cell-mediated antigen-specific leukemia clearance. This molecule has been approved for clinical use but optimum delivery programs have yet to be defined. In an attempt to alter the course of 70Z/3-L leukemia, we began by testing the effect of IP administration of rIL-12 on the appearance of morbidity after IP injection of $10^6$ 70Z/3-L cells. Doses of 0.1-20 ng/mouse/day for 14 days, which are at least 20-fold below the maximum tolerated dose in mice were tested. In FIG. 1a, the inventors show that doses above 10 ng were sufficient to significantly improve the survival of animals (p=0.002).

Intraperitoneal Administration of rIL-12 Leads to Long-Term Protective Immunity Against the 70Z/3-L Leukemia.

Figure 1B:
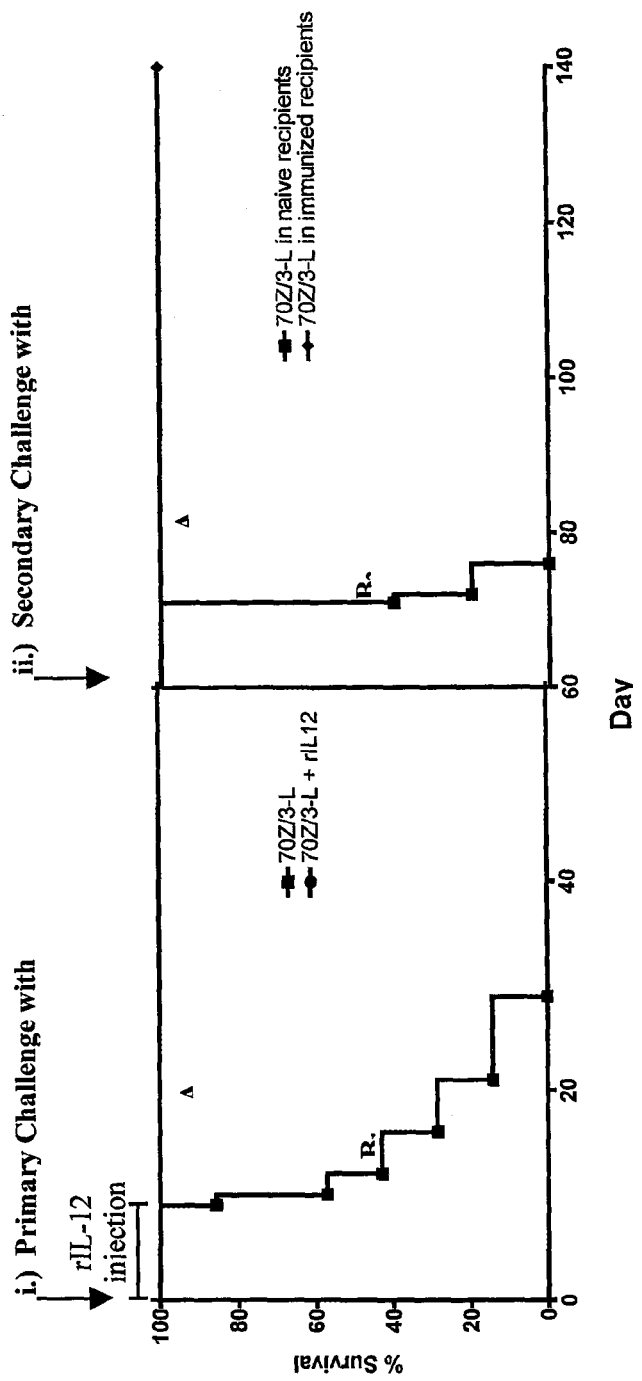
FIG. 1b IP administered rIL-12 therapy leads to long-term protection against challenge with 70Z/3-L. (i) Naïve mice (A, n=10) were challenged with 70Z/3-L cells on day 0 and treated for 14 days with injections of 20 ng rIL-12/mouse/ day. A group of mice (Bi, n=7) were included as controls for the 70Z/3-L cells (curve comparison by log rank test p=0.001). (ii) After a period of 70 days, five mice from group A, having undergone rIL-12 therapy, were secondarily challenged with $10^6$ 70Z/3-L cells without further rIL-12 treatment. The other five animals were kept to confirm that no toxicity appeared after 70 days. Five naïve mice (B2) were included to demonstrate the lethality of the 70Z/3-L cells (comparison of Kaplan-Meier survival curves was performed using Logrank test p=0.0015).

Next addressed is whether the results observed above were due solely to the acute effects of IP administered rIL-12 on innate responses or to the induction of a long-term adaptive immune response in the mice. To accomplish this, mice received IP injections of $10^6$ 70Z/3-L cells, were treated for 14 days with 20 ng/mouse/day rIL-12, subsequently challenged 70 days later by IP injection of $10^6$ 70Z/3-L cells and monitored for the appearance of symptoms. A group of naïve mice was included to control for the efficiency of the cells to cause disease. FIG. 1bii shows that all animals first treated with IP administration of rIL-12 (FIG. 1bi) survived a secondary challenge with 70Z/3-L cells in the absence of further IL-12 therapy. Thus, IP administration of rIL-12 not only protected against the primary 70Z/3-L challenge but also established long-term protective immune memory.

Intraperitoneal Administration of rIL-12 Protects Animals with Pre-Established 70Z/3-L Leukemia.

To determine if IP administration of rIL-12 can lead to leukemia clearance as well as protection from a developing neoplasm, treatment initiation was delayed to allow for dissemination of the disease. These experiments were conducted starting with $10^4$ 70Z/3-L cells injected IP because of their rapid growth. This dose is still lethal to 100% of mice in approximately 20 days. Initiation of rIL-12 administration was delayed by 0 to 5 days and continued for 14 days following the first injection. We found that the initiation of rIL-12 therapy could be delayed by 5 days and still achieve significant protection against the leukemia (FIG. 1c). The differences between the survival curves of the six treatment groups are not statistically significant and longer delays were not tested.

$CD4^+$ and $CD8^+$ T Cells are Required for the rIL-12-Mediated Rejection of 70Z/3-L Cells After IP Administration.

Figure 1D:
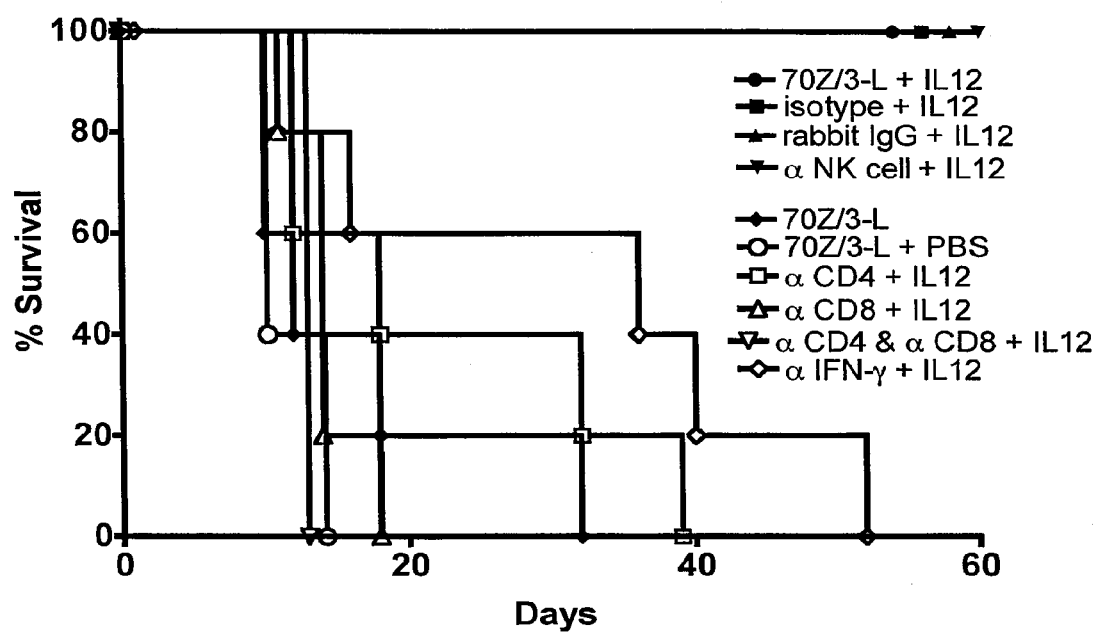
FIG. 1d Requirement of T cells and IFN-γ for rIL-12-mediated protection following IP administration. Mice (n=5 mice in each group) were depleted using antibodies as described in Materials and Methods. The mice were challenged with $10^6$ 70Z/3-L cells IP, injected with 20 ng/mouse/ day rIL-12 and monitored for the appearance of symptoms. Comparison of Kaplan-Meier survival curves was performed using Logrank test (p<0.0018).

Depleting antibodies were used to determine which cell types mediate the rIL-12-induced rejection of 70Z/3-L leukemia after IP administration. FIG. 1d shows that both $CD4^+$ and $CD8^+$ T cells are important as depletion of either population eliminates immune protection in all animals. The mean survival was 14 days for mice depleted of $CD8^+$ T cells, 23 days for mice depleted of $CD4^+$ T cells and 13 days for mice depleted of both T cell subsets. The three curves are not statistically different from each other. Neutralizing antibodies against IFN-γ were included to examine its role in the rejection response. This abrogated the protective effects of IP administered rIL-12 demonstrating that IFN-γ plays an essential role in leukemia rejection. Although the importance of NK cells has been shown in other models of IL-12 therapy[33, 34] changes in rejection of the 70Z/3-L leukemia were not observed when NK cells were depleted in this treatment modality (FIG. 1d).

Generation of IL-12 Secreting Leukemia Cells by Implementation of Lentiviral Transduction.

Figure 2A:
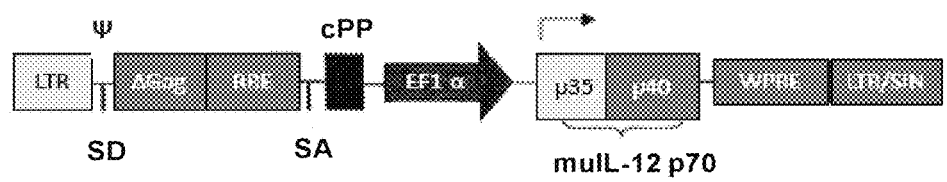
FIG. 2a Schematic representation of the LV-muIL-12 (LV-cPPT-EF1-mIL-12-WPRE) vector. LTR: long-terminal repeat; SD: splice donor; RRE: rev response element; SA: splice acceptor; cPPT: central polypurine tract; CMV: cytomegalovirus; WPRE: woodchuck hepatitis virus posttranscriptional regulatory element; muIL-12: murine interleukin-12; SIN: self-inactivating LTR.
Figure 2B:
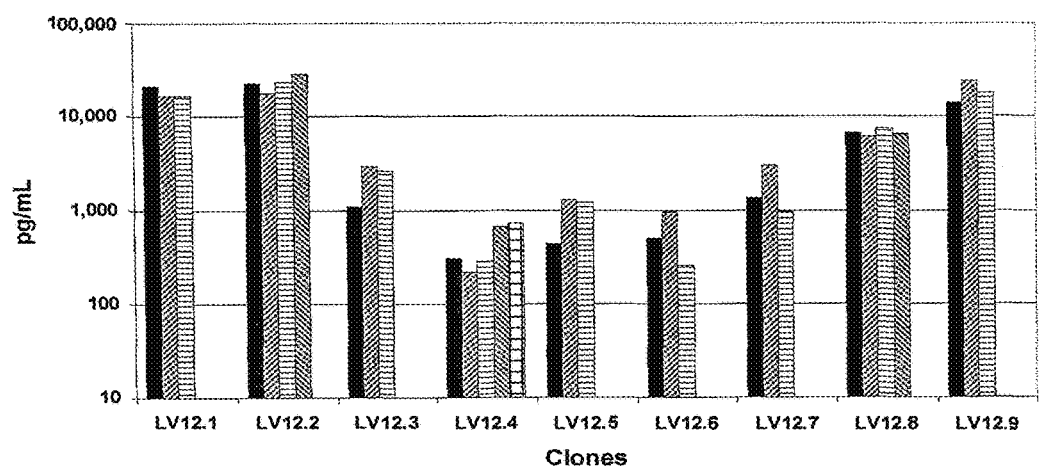
FIG. 2b Interleukin-12 secretion by vector-transduced clones is a stable trait. Levels of IL-12 secretion were measured by ELISA on 2-5 independent occasions and seen to remain fairly constant; differences are not statistically significant.

In light of these results, to the option of developing a leukemia cell-mediated approach for the delivery of IL-12 treatment was explored. FIG. 2a shows the lentiviral construct with an IL-12 fusion transgene under control of the EF-1a promoter that was generated. After transducing 70Z3-L cells with an approximate MOI of 20, single cell clones were derived as described in Materials and Methods. Supernatants from these clonal cell lines were tested for the production of IL-12. The range of secretion from selected clones varied from approximately 250 to 91,000 pg/mL/$10^6$ cells/2 hrs and these levels remained stable over time as shown in FIG. 2b. Furthermore, the different levels of IL-12 measured did not seem dependent on cell growth kinetics, nor on survival, as the in vitro growth properties of the vector-transduced clones were similar as measured by thymidine incorporation and visual inspection. Southern Blot analysis demonstrated that no clone had more than 7 proviral integration events.

Only a Small Proportion of Vector-Transduced 70Z/3-L Cells Producing IL-12 are Required to Confer Immunity.

Figure 3:
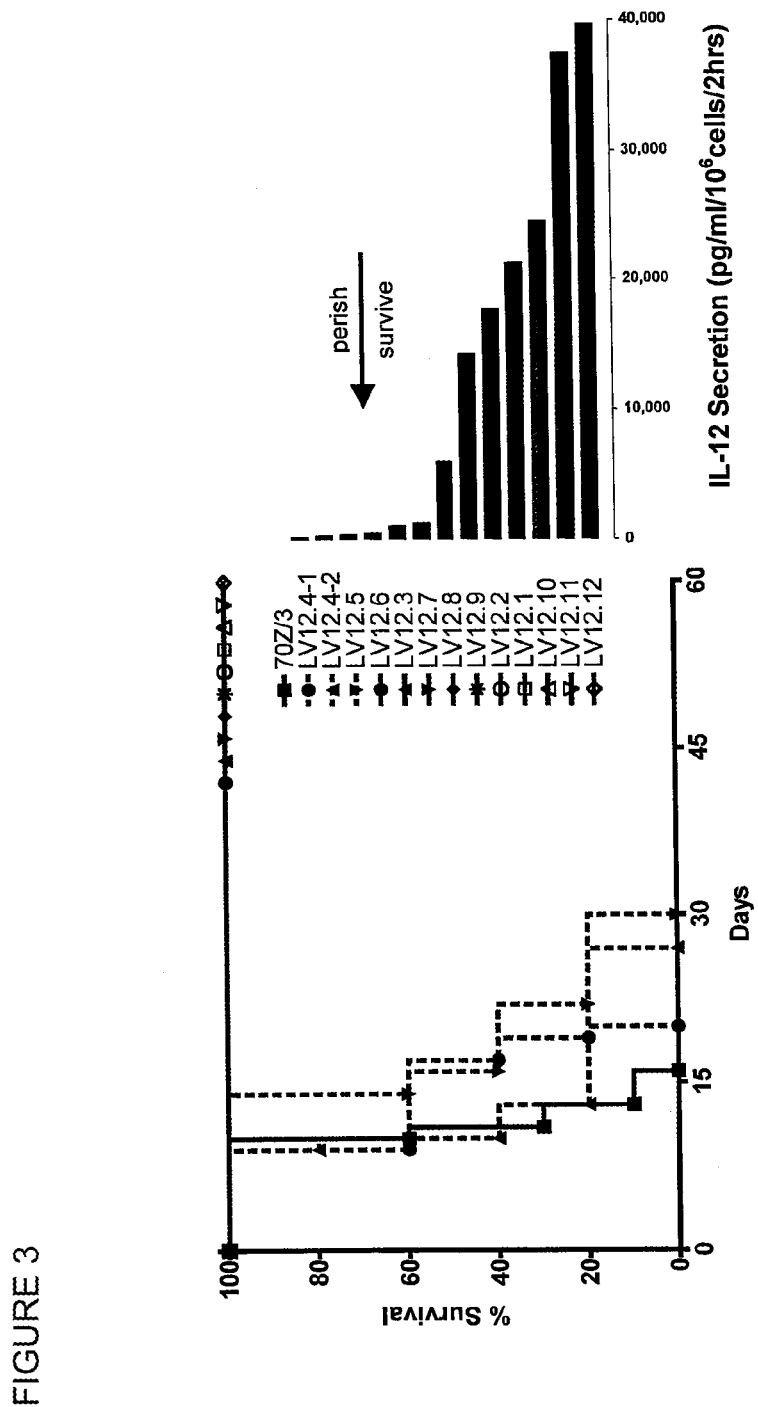
FIG. 3 Leukemia cell mediated IL-12 therapy leads to protection of challenged mice. Mice were injected IP with PBS or $10^6$ cells of either the parent line, 70Z/3-L, or one of the vector-transduced clones and monitored for the appearance of symptoms. Clones secrete varying levels of IL-12 and a theoretical threshold was established, below which protection is not conferred.

Whether the production of IL-12 by vector-transduced 70Z/3-L cells would elicit a protective immune response was determined by injecting $10^6$ cells of each of 12 clones, spanning a range of secretion levels, into the abdominal cavity of $BDF_1$ mice. The three lowest producing clones (range: 200-1,000 pg/mL/$10^6$ cells/2 hrs) failed to elicit an immune response and mice injected with these cells progressed towards death. In contrast, all mice injected with $10^6$ cells of the ten highest producing clones (range: from 1500-40000 pg/mL/$10^6$ cells/2 hrs) survived (FIG. 3). To date, the majority of the mice included in this study have survived past 2 years post-injection.

One 70Z/3-L transduced clone, LV12.1 which produces approximately 21,500 pg/mL/$10^6$ cells/2 hrs, was mixed with naïve 70Z/3-L cells to determine if the inclusion of IL-12 producing vector-transduced cells would result in the elimination of non-producing cells also. As little as 2% of the vector-transduced cells were sufficient to confer complete protection (FIG. 4a). To further examine the efficacy of producer/non-producer proportions, two other 70Z/3-L transduced clones were selected that differed in IL-12 production by 10-fold (clone LV12.3: 2,000 pg/mL/$10^6$ cells/2 hrs vs. clone LV12.2: 20,000 pg/mL/$10^6$ cells/2 hrs). In this case, as few as 0.5% (i.e. 5,000 LV12.2 cells in $10^6$ total cells) of the higher producing clone was sufficient to confer protection to 80% of the mice but 0.1% failed to protect any mice. However, even 10% (i.e. 100,000 LV12.3 cells in $10^6$ total cells) of the lower producing clone was insufficient to protect, indicating that a threshold of IL-12 production per vector-transduced cell is required to elicit an effective immune response (FIG. 4b).

Leukemia Cell-Mediated IL-12 Therapy Leads to Specific Long-Term Protective Immunity Against the 70Z/3-L Leukemia.

Figure 5:
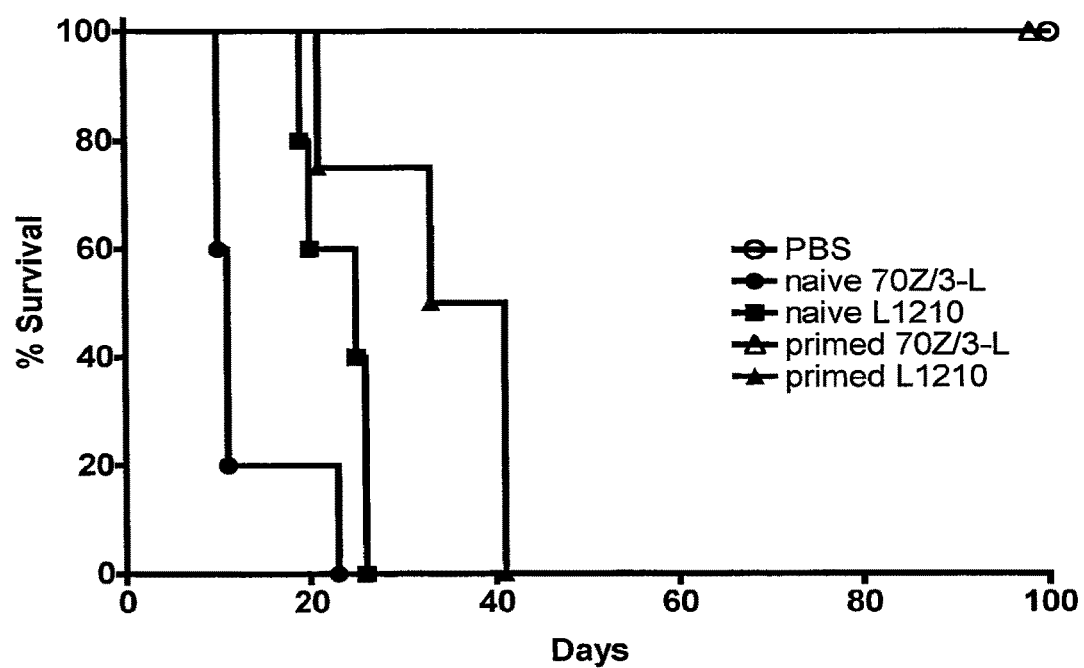
FIG. 5 Leukemia cell mediated IL-12 therapy leads to long-term and specific protection against challenge with 70Z/3-L. Mice were initially challenged with either $10^6$ LV12.2 cells or injected with PBS. More than 110 days following the primary challenge, primed mice (n=4 in each group) were secondarily challenged with either $10^6$ 70Z/3-L or $10^6$ L1210 cells. The PBS injected mice (n=5 in each group) also received either $10^6$ 70Z/3-L or $10^6$ L1210 cells to control for their efficiency to lead to morbidity, or another injection of PBS and monitored for appearance of symptoms. Kaplan-Meier survival curve comparison was performed using Logrank test, p<0.0001.

More than 110 days post IP injection with $10^6$ LV12.2 cells, mice were challenged with either $10^6$ cells of the parental leukemia line 70Z/3-L or another well-characterized B-cell leukemia, L1210, and monitored for the appearance of symptoms. Groups of naïve mice were included to control for the efficiency of both the 70Z/3 and L1210 cells to cause disease. FIG. 5 shows that all animals to survive the initial insult with LV12.2 were immune to subsequent challenge with 70Z/3-L but not L1210. Thus, cell-mediated IL-12 therapy leads to specific long-term protective immunity.

CD4+ T Cells are Primarily Required for Leukemia Cell-Mediated Rejection of 70Z/3-L Cells.

Figure 6:
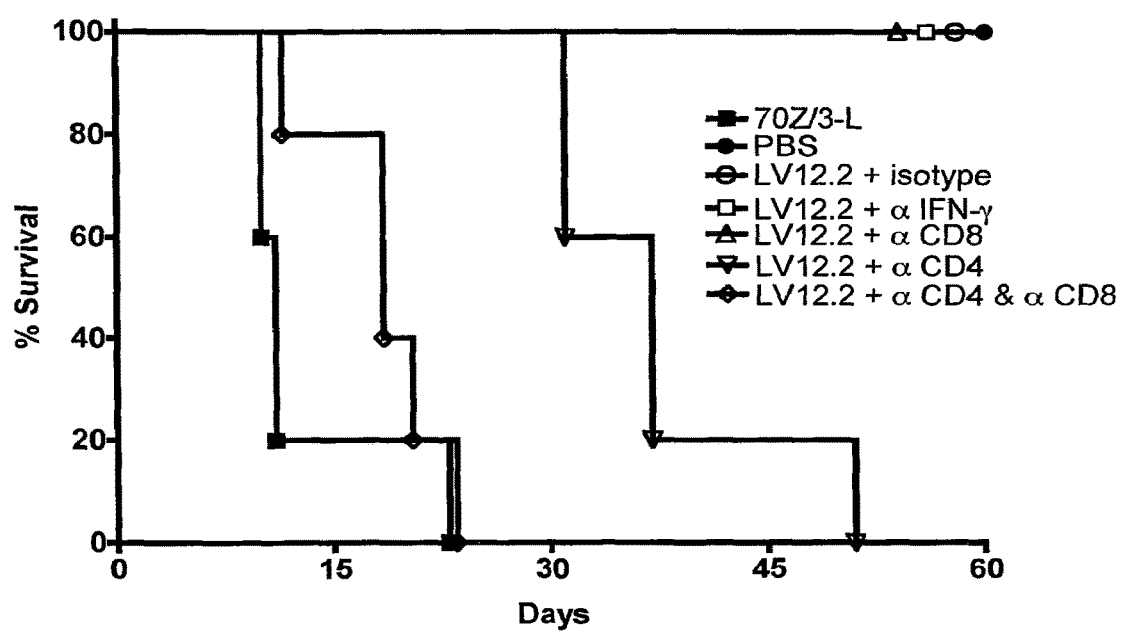
FIG. 6 Requirement of the CD4$^+$ T cell subset for leukemia cell-mediated protection of challenged mice. Mice (n=5 in each group) were depleted using antibodies as described in Materials and Methods. The mice were challenged with $10^6$ LV12.2 cells IP and monitored for the appearance of symptoms. Kaplan-Meier curve comparison was performed using Logrank test, p=0.0084.

Depleting antibodies were used to determine which cell types mediate the IL-12-induced rejection of 70Z/3 leukemia. FIG. 6 shows that the CD4+ T cell subset is of primary importance unlike in the IP administered rIL-12 therapy model above. The mean survival of leukemia challenged mice was 37 days for animals depleted of CD4+ T cells and 18 days for those depleted of both T cell subsets. The curves are statistically different (p=0.003), suggesting an important role for CD8+ T cells but only in the absence of CD4+ T cells. The CD8+ T cell subset alone is not sufficient to confer protection. Furthermore, the neutralization of IFN-γ did not diminish the protective effect as was seen with IP administered rIL-12 therapy (FIG. 6). This was a surprising result and prompted us to further interrogate the regulation of IFN-γ and various other inflammatory cytokines in each model.

In Vivo Cytokine Regulation.

Figure 7:
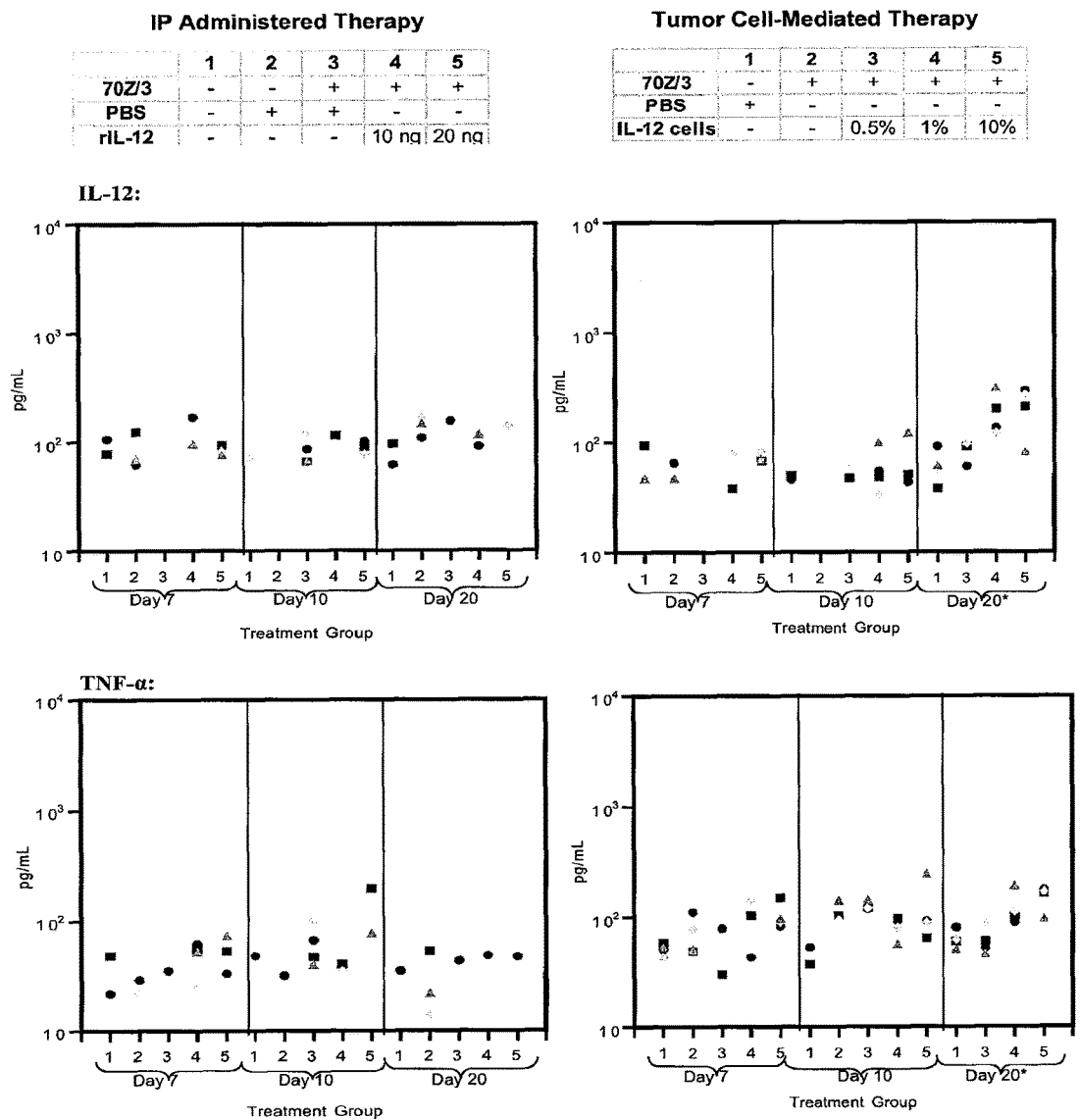
FIG. 7 Cytokine expression profiles of mice receiving IP administration and leukemia cell-mediated IL-12 therapies. The mice (n=4 in each group) receiving IP administered rIL-12 therapy were challenged with $10^6$ 70Z/3-L cells and received either no treatment or injections of 10 or 20 ng/mouse/day rIL-12 for 14 days. Mice (n=4 in each group) receiving leukemia cell-mediated IL-12 therapy were challenged with $10^6$ 70Z/3-L cells IP and received either no treatment or treatment with various proportions (0.5%, 1% or 10%) of the vector-transduced clone LV12.2. Serum samples were collected and analyzed on days 7, 10 and 20 as described in Materials and Methods. (*—all mice from group 2 in the leukemia cell-mediated model were dead by day 20 such that serum was not collected from this group).
Figure 7:
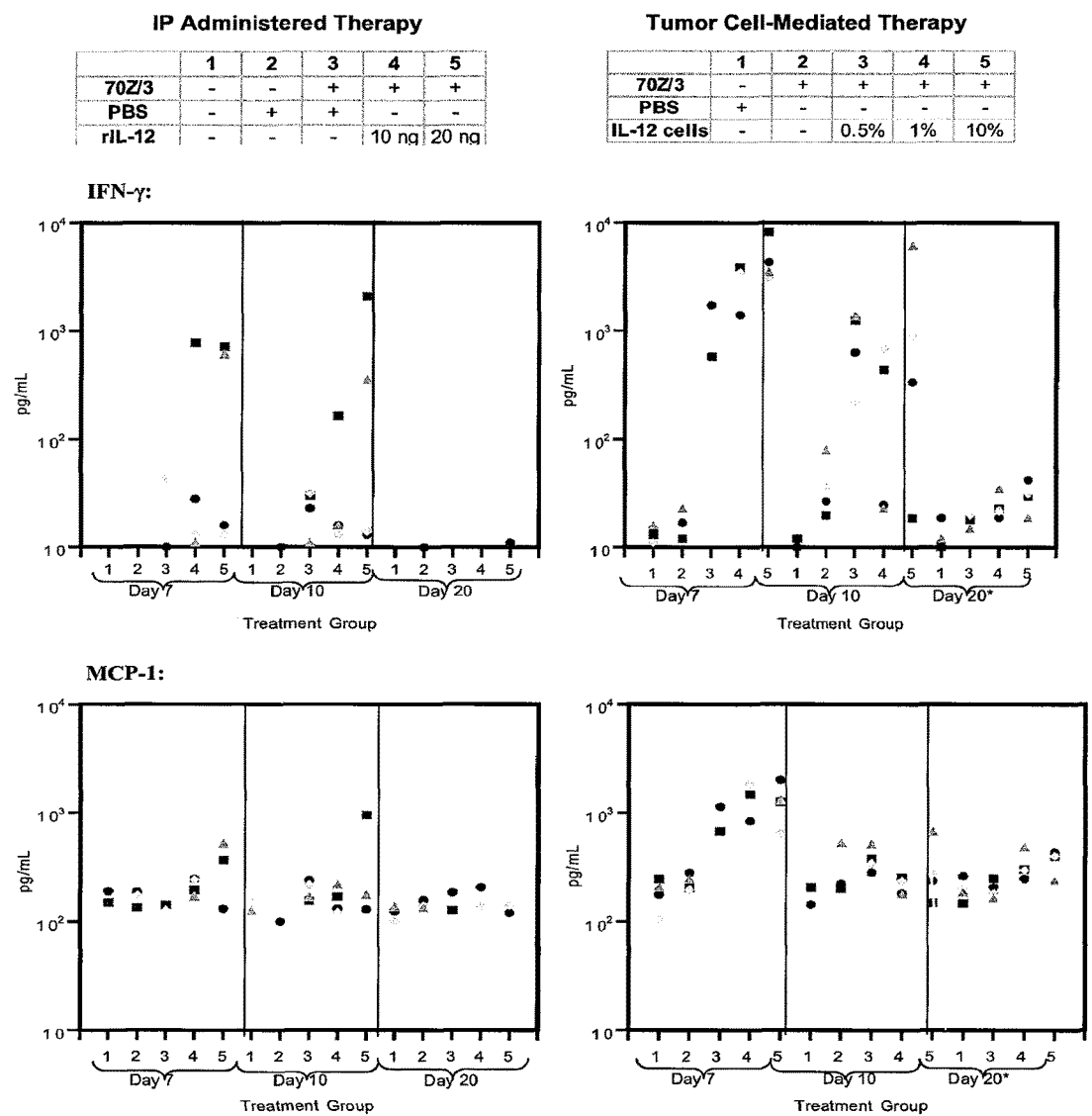
Figure 7:
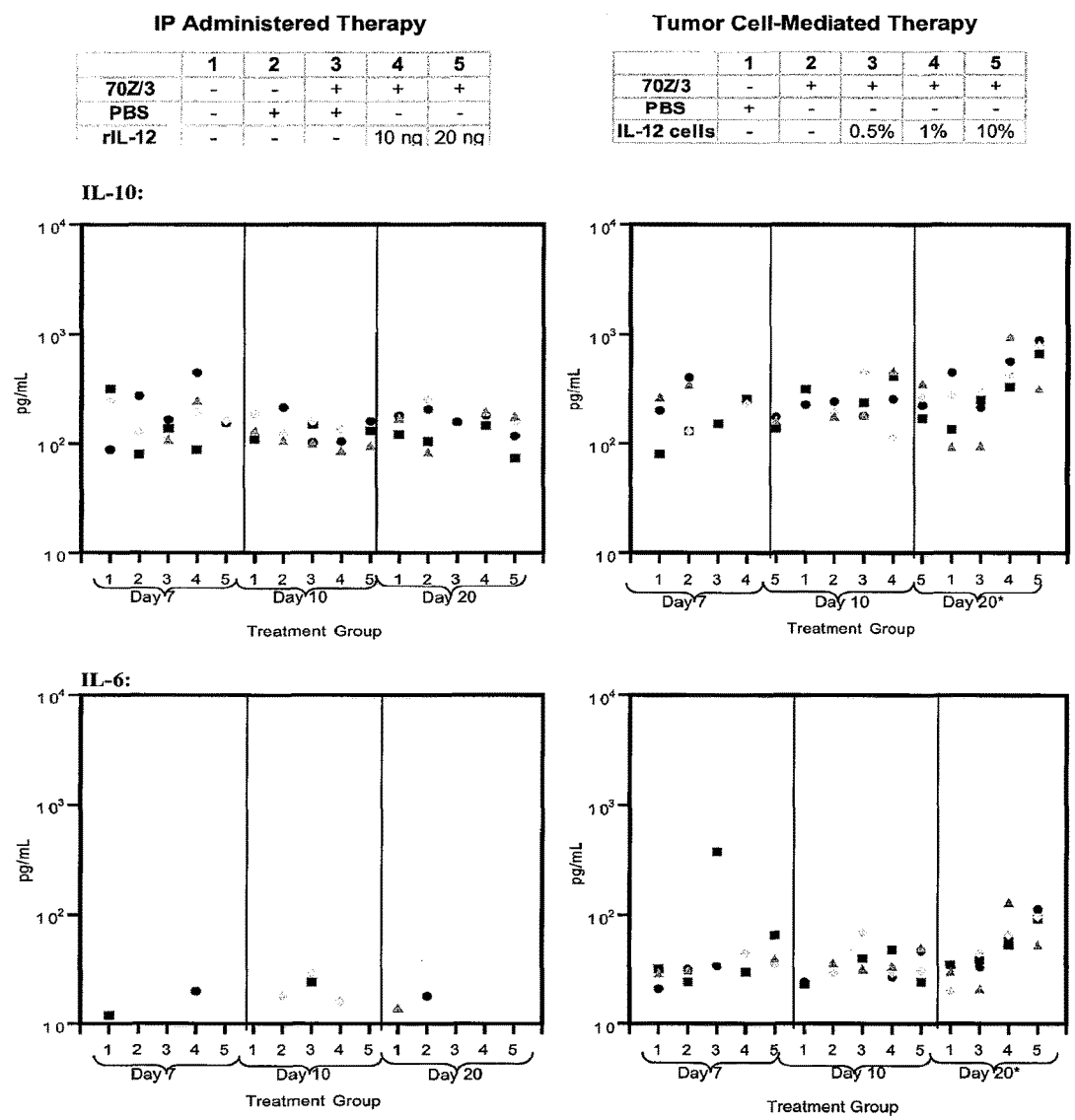

Interleukin-12 induces the secretion of other cytokines that can have agonistic, antagonistic or synergistic effects and can influence the specific immune response that is initiated.[6-8, 18, 35-38] It was therefore important to measure the regulation of some of these cytokines in vivo to better understand how leukemia rejection is accomplished and shed some light on the results of our neutralization experiments. For this purpose we employed a flow cytometry technique that detects a panel of inflammatory cytokines, including IL-12 p70, TNF-α, IFN-γ, MCP-1, IL-10 and IL-6 in serum. Mice received IP injection of $10^6$ 70Z3-L cells on day 0 and daily IP injections of either 10 or 20 ng rIL-12/mouse/day for 14 days. Serum samples were collected on days 7, 10 and 20. Alternatively, mice were challenged with an IP injection of $10^6$ 70Z3-L cells on day 0 spiked with various proportions (0.5%, 1% and 10%) of vector-transduced cells and serum samples were collected according to the same schedule as described above. The results of these two assays are shown in FIG. 7.

The levels of IL-10 induced on day 20 are significantly higher after leukemia cell-mediated therapy as compared to IP administered rIL-12 therapy (p<0.0017) but are not significantly different between IL-12 treated and control groups for either mode of delivery at any time point. Likewise, the levels of IFN-γ and TNF-α are significantly higher in response to IL-12 secreted from vector-transduced cells (p<0.0015 and 0.0110 respectively). Of note, however, is that leukemia cell-mediated treatment groups show significantly higher levels of IFN-γ than the control groups on day 7 (p=0.0007) but resolve to near basal level by day 20.

Discussion

The inventors demonstrate that IP administered low dose rIL-12 therapy can elicit a protective immune response in leukemia-bearing mice and that an effective approach to deliver IL-12 is via the leukemia cells themselves. Remarkably few transduced leukemia cells are needed to achieve protection provided a sufficient amount of IL-12 is produced per cell, and that protection is achieved in a manner distinct from that with IP administered rIL-12 therapy.

Given the key role that IL-12 plays in the initiation of effective immune responses in various leukemia models, the potential for cytokine therapy using a murine model of ALL was re-examined. It had previously been found that 70Z/3-L cells lead to the rapid death of mice injected with as few as $10^2$ cells. In contrast, variants of this line that are recognized by the immune system and subsequently rejected were established. Mixing as few as $10^5$ of these non-leukemic variants with $10^6$ 70Z/3-L cells resulted in complete rejection of all 70Z/3 cells.[39] While why these variants are recognized by the immune system has not yet been determined, these experiments revealed that 70Z/3-L cells can be rejected if the immune system can be modulated appropriately; making this experimental system amenable to the study of IL-12-induced anti-leukemia activity.

Interleukin-12-based therapies have not become front line cancer treatments in part because studies often report low response rates among patients.[6-8] The poor outcomes associated with IL-12 treatment in these clinical studies can be explained by the physiological response to IL-12-induced IFN-γ. For example high levels of IL-12, and consequently IFN-γ, have been shown to induce IL-10 and lead to downmodulation of IL-12 responsiveness in the host.[6] However, Gollob et al report chronic T helper type-1-like immune activation involving IFN-γ production is necessary for rhIL-12-induced antitumor effects.[18]

Previous groups have demonstrated that administration of IL-12 at doses significantly below the maximum tolerated dose can avoid the induction of antagonistic mechanisms. [20] The inventors demonstrated that IP administration of a dose as low as 10-20 ng of rIL-12 daily for 14 days, equivalent to 500-1,000 ng/kg, is sufficient to significantly increase the survival of mice injected with 70Z/3-L. This dose is effective against an established leukemia burden and rejection leads to long-term immune memory in a T cell-dependent manner.

Other strategies for delivery of IL-12 were investigated 70Z/3-L cells can be readily transduced with our novel lentiviral construct. Different vector-transduced clones produce varied amounts of IL-12. This appears to be a stable trait as we have measured similar levels of secreted IL-12 for each clone on 2-5 independent occasions. The vector copy number in these clones was determined but this alone does not explain the variable secretion levels, nor does their rate of proliferation. One possible explanation, however, is that the variable secretion is a result of different integration sites and the effect of different genes controlling transgene regulation.

The establishment of clones that produce different levels of IL-12 has allowed examination of the relationship between IL-12 production and the proportion of IL-12+ vector-transduced vs. IL-12− naïve 70Z/3-L cells necessary for immune activation. To date, this potentially critical aspect of cell-mediated cytokine therapy has not been thoroughly examined. A very small proportion of IL-12 producing vector-transduced 70Z/3-L cells are sufficient to trigger a protective immune response. For one clone, LV12.2, 5,000 such vector-transduced cells (but not 1,000) were sufficient to save 80% of the mice injected with $10^6$ 70Z/3-L cells.

This result could indicate either that a critical number of "hits" or a sufficient amount of IL-12 is required to trigger an immune response. A reasonable interpretation of "hit" might be an encounter between an IL-12 producing vector-transduced 70Z/3-L cell and an appropriate APC, such as a DC. The alternative explanation proposed is that these 5,000 vector-transduced cells simply deliver a sufficient quantity of IL-12 into the system to trigger an immune response in a more direct fashion. To determine which of these explanations is correct, a different clone, LV12.3, that produces 10-fold less IL-12 per cell was employed. Titrated numbers of vector-transduced cells were injected along with $10^6$ 70Z/3-L naïve cells. Even 100,000 of such vector-transduced cells failed to confer protection. This represents twenty-fold more cells and twice the potential IL-12 released into the system. Together, these results suggest that it is the number of "hits" that matter rather than the absolute amount of IL-12, but that to qualify as a "hit", the vector-transduced 70Z/3-L cell must produce IL-12 above a certain threshold.

These findings have important implications for clinical trial design and may explain at least part of the differences observed between murine studies, in which IL-12 can initiate a curative immune response, and human studies, in which the immune response is modest and patient survival is normally unaffected. The protocols used in mouse studies usually involve selection of clones that secrete relatively high levels of IL-12 and frequently the preparation administered consists of 100% IL-12 secreting cancer cells. In contrast, human studies generally rely on freshly obtained populations of cancer cells that are difficult to clone. Therefore bulk populations of cells are transduced and average amounts of IL-12 produced by these populations are measured. In cases reported to date, these average amounts are far below what is predicted to be necessary to elicit protective immunity and there is no information on the distribution of production levels within these populations.

The IL-12-induced anti-leukemia activity in our two models is T cell-dependent but the subsets that are critical differ depending on the mode of IL-12 delivery. The role of IFN-γ also appeared to differ, prompting us to look at its in vivo regulation along with a number of other inflammatory cytokines. This was done using a flow cytometry based cytokine bead assay. The regulation of IL-10, IFN-γ and TNF-α are of particular interest in our model systems because IL-10 is known to be the most biologically relevant antagonist of IL-12,[4] IFN-γ is may mediate the effects of IL-12[4, 13] and a combination of IFN-γ and TNF-α is required for the development of CD4$^+$ CTLs.[5]

The fact that IL-10 production was not elevated above background in any of our treatment groups suggests that the amount of IL-12 administered was sufficiently low as to avoid the induction of antagonistic molecules and dampening of the biologic effect. Measured levels of IFN-γ were significantly higher in the treated groups receiving leukemia cell-produced IL-12 as compared to controls on day 7 but were not significant by day 10 and returned to near baseline by day 20. Furthermore, IFN-γ production was significantly greater in the leukemia cell-mediated model in general. In light of these results, it is probable that the leukemia cell-mediated IL-12 therapy neutralization experiment did not demonstrate a critical role for IFN-γ simply because the neutralizing antibody was overwhelmed by the levels produced. There is ample literature describing how IL-12 leads to the increased maturation of DCs, the production of IFN-γ and more efficient antigen presentation by the IFN-γ-dependent up-regulation of MHC-II and co-stimulatory molecule expression. T-helper lymphocytes are driven by IFN-γ to differentiate with a type-1 functional profile and subsequently promote the strong CD8$^+$ CTL response that we saw with IP administered rIL-12 therapy. However, there is also a literature describing a role for CD4$^+$ CTLs in models of infection [5, 40, 41] and more recently in tumor immunology [42-46]. It is possible that the IFN-γ and TNF-α rich environment resulting from leukemia cell-mediated therapy led to the development of an effector CD4$^+$ population. This could account for the differential importance of T cell subsets in our two models and explain the distinct results of the neutralization experiments. The major thrust of tumour vaccination research has traditionally focused on targeting CD8$^+$ CTLs, which require stimulation by a CD4$^+$ helper T cell population, to affect tumour clearance but the clinical response has been limited. Directly targeting CD4$^+$ effector cells may be important to achieve a more robust anti-tumour response.

Despite the beneficial effects of IFN-γ that we have highlighted above, a dampening of the response with repeated administration is still of concern in models of IL-12 therapy. An important attribute of our leukemia cell-mediated model is that a sufficient immune response is initiated and the leukemia cleared but the signal is self-limiting because the source of IL-12 into the system is the cancer cells that are, themselves, the target of therapy. As the leukemia cells are rejected, the source is reduced and IFN-γ levels return to baseline without a significant increase in the antagonistic molecule IL-10.

IL-12, given at doses below the level leading to the induction of antagonistic mechanisms, is sufficient to launch a protective immune response against 70Z/3-L ALL cells and complete clearance of the leukemia. The mode of IL-12 delivery can have a profound impact on the nature of the immune response that is mounted and demonstrates a critical role for CD4$^+$ cells in our leukemia cell-mediated model that apparently does not exist in our IP administration model. Although previous studies have been concerned with the counter-productive side effects resulting from elevated levels of IL-12-induced IFN-γ, several critical and beneficial roles for this cytokine have been demonstrated. Moreover in our model, a potentially problematic dampening of the immune response was not observed, possibly due to the self-limiting nature of the leukemia cell-mediated therapy approach employed.

This work in a murine model of ALL using a LV constructed that engineers expression of murine IL-12 has demonstrated that animals can be completely protected from leukemia-induced death when certain levels of IL-12 are produced by the transplanted cells Example 2

Acute Myeloid Leukemia
The Following Myeloid Leukemia Lines were Transduced with the Murine LV IL-12 Construct.

A lentiviral vector, (pHR-cPPT-EF1α-muIL-12-WPRE) that engineers expression of murine interleukin-12 (mIL-12) was constructed and characterized. Plasmid pORF-mIL12 (IL-12elasti(p35::p40) Mouse (p35::p40)) was modified by creating EcoRI and BamHI restriction enzymes sites, upstream and downstream of the muIL-12 gene, respectively, using a QuickChange Site-Directed Mutagenesis Kit (Stratagene, La Jolla, Calif.). This resulting construct was then digested with EcoRI/BamHI (New England Biolabs). Murine IL-12 cDNA was purified after electrophoresis on a 1% agarose gel, and then subcloned into the pHR' LV backbone downstream of the elongation factor 1 a promoter (EF1a). Positive plasmid clones for pHR-cPPT-EF1α-muIL-12-WPRE (i.e. LV-muIL-12) were identified by diagnostic restriction enzyme digestion analyses and subsequent DNA sequencing (Innobiotech, Toronto, ON, Canada).

Lentivirus was produced by transfecting 293T cells with the plasmids pCMVΔR8.91, pMDG and either control enGFP lentivector (pHR-Cppt-'EF-GW-SIN). Viral supernatants were collected at 48 hours post-transfection, filtered and concentrated by ultracentrifugation. Concentrated virus was serially diluted and the efficiency of viral production was assessed by detection of p24 antigen by ELISA.

To determine the transduction efficiency of mIL-12 lentivirus murine myeloid leukemia lines MMB3.19 and C1498 (1 million cells/ml) were infected in vitro with mIL-12 or enGFP lentivirus at a multiplicity of infection (M.O.I) of 1. The infected cells were maintained at 37° C. and the media changed 24 hours after culture. The supernatant was collected 48 hours later and the levels of IL-12 measured by ELISA.

Cells transduced in vitro with lentivirus encoding mIL-12 produce efficiently high concentrations of IL-12 [~214 ng/ml and 7.5 ng/ml for MMB3.19 and C1498 cells, respectively). MMB3.19-IL-12 and C1498-IL-12 cells secreted 214 and 7.5 times more IL-12, respectively, than the enGFP transduced cells. The results are illustrated in the chart below.

|  | GFP | MIL-12 |
| --- | --- | --- |
| MMB3.19 | 0.9 | 214.7 |
| C1498 | 0.9 | 7.5 |

Example 3

Human IL-12

I. Lentiviral Vector Construction.

Lentiviral vectors expressing human IL-12 cDNA were constructed by a method similar to that described for mouse IL-12 construct. The cDNA of human IL-12 was obtained as a fusion form from InvivoGen (pORF-hIL12 (IL-12elasti (p35::p40)). The open reading frame of the gene was amplified by the following PCR primers: hIL-12 ORF Fwd, 5'-TTGGCGCGCCACCATGGGTCACCAGC-3'; and hIL-12 ORF Rev, 5'-TTGGCGCGCCTTAGGAAGCATTCA-GATAGCTCATCACTC-3'. The PCR product was then subcloned into our Lentiviral backbone (pHR'-cPPT-EF1α-WPRE). The construct was confirmed by diagnostic restriction enzyme digestion analyses and subsequent DNA sequencing.

II. Transfection Experiment

To assess the pHR'-cPPT-EF1α-hIL12-WPRE construct, 1×10⁶ 293T cells were transfected with the construct, the human IL-12 template pORF-hIL12 or empty lentivector pHR'-cPPT-EF1α-WPRE. Cell supernatant was collected 24 and 48 hours after transfection. The hIL-12 level was measured by ELISA (BD pharmingen, San Diego, Calif.) (Chart below).

III. Transduction to 293 T cells

Lentivirus carrying hIL-12 open reading frame (LV-hIL-12) were produced by a transient triple-transfection method using pHR-cPPT-EF1α-hIL-12-WPRE and accessory plasmids onto 293T monolayers by polyethylenimine. Virus supernatant was collected 24 and 48 hours after transfection. To test the transduction ability of the LV-hIL1, 1×106 293T cells were transduced with the virus supernatant. hIL-12 expression level in the cell supernatant was measured by the same ELISA assay as mentioned above (Chart below).

IV. Transduction to AML.1 Cells 200-fold concentration of LV-hIL12 virus was obtained by ultracentrifuge. To test the transduction ability of the virus to other tumor cell lines, 0.5 or 1 million of AML.1 cells (an acute leukemia cell line) were transduced with 1/100 diluted concentrated LV-hIL12 virus. hIL-12 expression level in the cell supernatant was measured by the same ELISA assay as mentioned above.

|  | 24 h Ave (pg/ml) | SD | 48 h Ave (pg/ml) | SD |
| --- | --- | --- | --- | --- |
| LV-hIL12 | 1010.052 | 33.145 | 840.397 | 24.184 |
| pHR-hIL12 | 774.131 | 340.254 | 933.513 | 50.522 |
| pORF-hIL12 | 1079.439 | 62.461 | 959.165 | 19.813 |
| pHR vector | 0 | 1.762 | 0 | 3.98 |

LV-hIL12 will be used to transduce other human leukemic cell lines and primary cancer cells derived from subjects with leukemia.

Example 4

Chronic Myeloid Leukemia in Humans

Immunotherapy offers a method to improve the treatment of leukemias, in particular in combination with other treatment modalities. Indeed, maybe only potent immune system-invoking therapy will be effective at fully eradicating leukemia since residual disease often exists in patients that are in remission, which can be re-activated later. This is especially true for chronic myeloid leukemia (CML), a clonal disorder involving the Philadelphia chromosome, which represents 15% of all adult leukemias. On the other hand, this delayed disease progression provides a key window of opportunity for immunotherapy. Since immunotherapy is not dependent on abrogating cell functions by interrupting signaling or on intercalation into DNA by small molecules, for example, it can also be effective on transformed cells that are quiescent or inhabit inaccessible locales. Of importance, immunotherapy may be an effective way to target true cancer stem cells. Lastly, due to the circulating and surveillance nature of the immune system, existing metastatic disease even in primary CML patients could be treated by this approach.

Approximately 4500 new patients are diagnosed with CML in North America every year. Onset of the most prevalent form of CML is associated with a reciprocal translocation between chromosomes 9 and 22 leading to the formation of Bcr-Abl oncogene. This is manifested by a rapid expansion of bone marrow-derived hematopoietic cells of the myeloid lineage. Current first-line therapy involves treatment of CML patients with imatinib mesylate (Gleevec®), a small-molecule tyrosine kinase inhibitor of the Bcr-Abl product. Unfortunately, this is not a curative treatment. In fact, 4% of early-stage and a full 50% of advanced-stage CML patients develop resistance to imatinib mainly due to ABL1 mutations (1). Imatinib another treatment, is also costly and requires life-long ingestion of the drug; effects of prolonged administration (or of others of this class) are not known. This strategy is also not likely to impact the cancer stem cell, which may be relatively quiescent and thereby resistant to metabolic modulation. Also the lack of inhibitor specificity for only the Bcr-Abl product means that other tyrosine kinases can also be affected. As such, imatinib has shown some serious side effects; a recent study has shown that mice and human patients receiving imatinib demonstrate severe cardiotoxicity (2).

A wide range of immunotherapy strategies have been envisioned. Indeed, it has been known for years that the immune system is capable of recognizing and clearing cancer cells in some instances and yet not in others. Cytokines have pleiotropic effects on the immune system. One cytokine that has received a lot of attention towards amelioration of cancer is interleukin-12 (IL-12). IL-12 is heterodimeric and acts to increase antigen presentation by dendritic cells (DCs) and to induce their maturation. The basic concept behind therapy using IL-12 is that it alerts the immune system to a higher degree of vigilance and if this attention can be directed against cancer cells, elimination by the immune system may be possible. IL-12 has been given as a systemic bolus for treatment of leukemias but clinical outcomes have been quite modest. This may be due to difficulties in establishing appropriate dosing per patient and the severe peripheral toxicities observed.

Interleukin-12 (IL-12). IL-12 is a heterodimeric cytokine with multiple biological effects on the immune system. It is composed of two subunits, p35 and p40, both of which are required for the secretion of the p70 active form. IL-12 acts on DCs, leading to increased maturation and antigen presentation, which can allow for the initiation of a T cell response against tumor specific antigens. It also drives the secretion of IL-12 by DCs, creating a positive feedback mechanism to amplify the response. Once a response is initiated, IL-12 directs the immune system towards a Th1 cytokine profile, inducing $CD4^+$ T cells to secrete IFN-$\gamma$ and leading to a $CD8^+$ cytotoxic T cell response (3). However, IL-12 is also a strong pro-inflammatory cytokine that leads to the secretion of other cytokines including TNF-$\alpha$ which, combined with IFN-$\gamma$, is a prerequisite for the development of $CD4^+$ cytotoxic T lymphocytes (CTL; ref. 4). Furthermore, IL-12 can promote the activation of macrophages and eosinophils through induction of IFN-$\gamma$ and other cytokines. This leads to IL-12 secretion and further amplification of both the innate and acquired responses (3). However, high levels of IL-12, and consequently IFN-$\gamma$, have also been associated with induction of antagonistic molecules such as IL-10 and the depletion of signaling molecules downstream of IL-12, such as STAT4 (3, 5-7).

Lentiviruses (LVs) and Gene Therapy. The first approved gene therapy clinical trial was published in 1989. Since then >2500 patients worldwide have received gene therapy to date.

Safety is a high priority. One major vector system that has been responsible for generating renewed enthusiasm is based on LVs. LV are most-commonly derived from HIV-1 (17). Substantial segments of the viral genome have been deleted and additional safety elements, such as self-inactivating LTRs, have been added (18). Moreover, these vectors are now produced in ways to reduce the possibility of recombination developing replication competent lentivirus (RCL). Indeed, substantial effort has gone into testing the safety and efficacy of this platform; for example, LVs offer stable integration but with less insertion into promoters that can disrupt cell functions than occurs with onco-retroviruses. LVs also allow the ability to engineer co-expression of more than one gene. A number of these bicistronic constructs have been generated by the inventors (see ref. 19, 20). The LV constructs comprise a novel suicide control system. This enzyme/prodrug combination employs a modified human enzyme engineered to respond to AZT (ref. 21; see Comment (ref. 22). This safety system offers the ability to control the fate of transduced cells and will be practical to use in any setting involving transplant of tumor cells, stem cells, and the like.

Safety improvements and the efficiency of LVs have recently led to clinical trials. The first LV trial was been completed in 2006 and involved anti-sense RNA sequences as transgenes that targeted HIV (23). This study was performed in AIDS patients with high viral loads; some reductions in these viral loads were observed. More importantly, no RCL was found between the recombinant vector and the endogenous wild-type virus. These results have now led to at least 6 other LV protocols being initiated for indications including cancer and inherited disease. Such outcomes have also led to a renaissance in corporate interest in gene therapy that still has a large but untapped potential to treat a variety of disorders.

As the inventors have found, localized concentration of IL-12 at the tumor/DC/T cell interface may be relevant for up-regulation of the immune response, and effective dosing at that site is not being generated in the clinical protocols.

State-of-the-art gene transfer techniques (lentiviruses; LVs) were used to quantitatively modulate the expressed IL-12 profile by the tumor cell itself. LVs are very efficient at stably transferring genes into cells.

The inventors have generated a novel clinically-oriented LV that engineers expression of human IL-12. Virus has been produced and virus and the vector have been validated in established human cancer cell lines by quantitating titer and human IL-12 production. Human primary CML cells will be transduced which will produce varying levels of human IL-12. The cells will be analysed to demonstrate that the human IL-12 produced by the tranduced cells is functional. A pre-clinical xenograft model will be adapted to examine maintenance of the transduced CML cells. The kinetics of human IL-12 produced in vivo will be measured.

Gleevec is the treatment of choice; however side effects, resistance, the need for long-term therapy, and high cost are associated with Gleevac use.

Murine models of CML. Two established CML lines were tested and show differential production of IL-12 in vitro in transduced populations derived from these lines.

CML and ALL are similar in that high remission rates in adults are followed by high relapse rates. This clinical course not only provides initial material suitable for infecting with the vector constructs described herein but a rationale for subsequent treatment. Importantly, CML shows this bi/tri-phasic progression and some initial response to imatinib that allows time to develop immune modulating tumor cells following vector transductions.

LVs offer some real advantages over other gene transfer methods that seek to generate stable cell lines secreting IL-12 for such applications: for example—plasmid transfection is very inefficient and adenovirus- or AAV-mediated gene delivery do not lead to appreciable vector integration, which will provide variable levels of IL-12 over time. The inventors have shown that transduced murine cells stably express transgenes ~2 years after initial infection (24).

Synthesis of human vector. A recombinant LV that engineers stable expression of human IL-12 was generated. The cDNA for human IL-12 was obtained as a fusion form from InVivoGen (pORF with IL-12elasti(p40::p35)). This cDNA was subcloned as above into the pHR' LV backbone. Diagnostic restriction digests and sequencing of both DNA strands was performed to confirm the fidelity of the new construct. This first construct will be monocistronic; other constructs may employ our suicide strategy involving mutated thymidylate kinase mentioned above (21) that would add another layer of safety.

Generation of high-titer vector stocks. High titer recombinant virion stocks were generated and titered in vitro. High titer vector stocks were established by ultracentrifugation of collected and pooled supernatants after triple plasmid transfections of 293T cells as done before (20). The vector was pseudotyped with the VSV-g glycoprotein which allows a wide range of cells to be infected. After sufficient titer of the pHR'human IL-12 delivery vector is obtained, pooled vector stocks will be tested by a 'Direct' assay to ensure that RCL has not been generated. In this assay, recipient 293T cells are infected a single time and then grown out for a number of passages. After 4-6 weeks, supernatants from these infected cells are collected and used to infect naïve cells. These cells are grown out and then assayed by functional assays and PCR on isolated genomic DNA to determine if vector has been functionally transmitted to these secondary recipient targets.

Testing in 293T cells. The level of human IL-12 produced in comparison to vector copy number in infected cells will be determined. Firstly, 293T cells will be infected at a range of modest MOIs from about 0.1 to 100. Supernatants from pools of infected cells, done in triplicate, will be examined for human IL-12 production by ELISAs. Next, individual cell clones will be established by limiting dilution. These cell lines will examined for human IL-12 production relative to copies of integrated provirus—as measured by Southern blots. Controls will be comprised of 293T cells infected with a LV/eGFP viruspreviously constructed (19). This information will provide information relating to the relative MOIs to be used and allows correlation of the secretion of this human form of IL-12 with relative vector copy number. Use of this stable cell line will provide a reference point for titering all future viral preparations that are made with the intent of infecting patient CML cells, which may have considerable variability in sample-to-sample infection frequencies.

Testing in Human CML. Firstly, established CML cell lines will be infected at various MOIs and clonal populations will be assessed for IL-12 expression in relation to vector copy number. It has been shown by the inventors that K562 (a CML line) is readily and productively infected with recombinant LVs (21). Numerous clones from each pool will be derived and examined for vector copy and relative human IL-12 production. Cell viability of clones producing various levels of human IL-12 over time will be measured by thymidine incorporation assays. Cells will be cultured for many weeks and compared with original clones frozen initially after limiting dilution to determine if human IL-12 production changes over time. Vector stability will also be measured in these cells by repeat Southern Blot analyses. Secondly, primary human CML cells will be obtained from a minimum of 3-5 CML donors initially to reduce reliance on a single sample. Here cells will be infected at 2 or 3 different MOIs. Cells from each donor will be handled separately to give information on the variability that can be expected. As above, human IL-12 production will be measured by ELISA in relation to vector copy number.

Additional pre-clinical data will be obtained. From a number of transduced K562 and Jurkat clonal lines, the sequence of the human IL-12 cDNA from the integrated provirus in genomic DNA will be determined after PCR amplification and subcloning to a stable plasmid. This will provide information on the stability of the vector itself and whether recombinations are occurring that could decrease protein expression levels from a given vector copy number. If consistent alterations are observed in a variety of clones such sequences could be mutated to reduce overlap or alter secondary mRNA structure to favor maintenance of fidelity. Further the vector integration site of cell populations by LM-PCR will be analysed to determine clonality. It will also be important to determine that the human IL-12 secreted by the transduced CML clones is functional. For this primary human DC cultures will be used to examine stimulation and the enhancement of T cell proliferation compared to controls.

It will be determined whether vector-transduced primary CML cells that have undergone growth arrest (by very high dose irradiation, for example) in preparation for safe clinical infusions into patients are still able to secrete similar levels of human IL-12 compared to control cells. No differences are expected as others have shown stable expression of GM-CSF and CD40L, for example, in patient leukemia cells after irradiation (25). One group even reported enhanced transgene expression in leukemia cells after γ-irradiation (26). Also, the suicide gene component mentioned above may be added, and killing efficiency of bicistronically transduced primary CML cells producing human IL-12 will be assessed after AZT addition at concentrations we have used before (21).

Test CML cell growth in vivo. The cell lines are assessed for growth in vivo. Cells will be introduced in immune deficient NOD/SCID mice and mice will be examined for the persistence of transduced CML cell lines and primary patient cells in vivo in this xenograft model. This model shows stable engraftment of human hematopoietic cells, especially when an antibody is given to reduce murine NK cell activity. anti-CD122 antibody (24) from a hybridoma cell line is purified in milligram quantities. Both growth-arrested cells and un-manipulated transduced cells will be given at various doses to recipient NOD/SCID mice. Persistence of transduced CML cells will be determined by conventional assays involving flow cytometry for human cell surface antigens (such as CD45/CD71) along with RT-PCR analyses for the LV as has been done for the Bcr-Abl oncogene fusion (27). These studies will be important to prove that the CML cells comprise the primary populations in the xenografted animals. As well, circulating levels of human-specific IL-12 will be determined by ELISA; production of secondary cytokines such as IFN-γ is also measured.

Where the bicistronic vector that engineers expression of the novel suicide gene is employed, the effectiveness of transduced cell killing in vivo can be measured after the addition of AZT to animals—dosing that is below the level of systemic toxicity is described in (21). A fully adaptive transplant system in this xenograft model is developed wherein matching genetically modified cells are returned to animals previously reconstituted with autologous patient hematopoietic components. The optimal dose of IL-12 relative to immune response is determined. The effect of the addition of other co-stimulatory molecules or alternative cytokines that perturb the immune response invoked either positively or negatively are assessed. Lentivectors that express shRNAs that downregulate expression of important genes that may effect stimulation such as IL-10 are also assessed. The contribution of various populations of hematopoietic cells themselves using depletion and sorting-mediated add-back studies are also assessed.

Anti-CD122 antibody increases human cell engraftment in NOD/SCID mice. NOD/SCID mice were either not pre-treated (n=3) or pre-treated with anti-CD122 (200 µg; i.p. injection; n=3). 24 hrs later, mice were irradiated (350 cGy; $^{133}$Cs source) and injected i.v. with 7×10$^5$ purified cord blood-derived human CD34$^+$ cells. At 7 weeks post-transplant, bone marrow was harvested, and human cell engraftment was determined by flow cytometry using anti-human CD45 PE. Two of three control recipients lacked long-term human cell engraftment, as defined by 1% CD45$^+$ events.

Example 5

Leukemia cells from 4 donors from each group (CML, AML, CLL, ALL) will be enriched following Ficoll centrifugation by established protocols. Initially, for AML and ALL we will carefully select patients with high leukocyte (>60 k) and high % blast counts in which case we expect enrichments to exceed 95% purity. For CML, patients in blast crisis will be selected to achieve the same result. For CLL mature CLL lymphocytes from patients with very high leukocyte counts (>100 k) will be achieved to achieve this enrichment. In each experiment, the leukemia cell population will be infected at 3 different MOIs using our LV/huIL-12 construct and a LV/enGFP control. An enzyme-linked immunospot (ELISPOT) assay for use as a readout in these experiments is being developed. The cloned, stable, murine lines produce a range of IL-12 from 200-40000 pg/$10^6$/ml/2 hrs and serve to calibrate the ELISPOT assay by correlating spot size to known secretion levels at the signal cell level. A similar calibration set will be created with human established cell lines by subcloning after the primary LV/huIL12 transduction. The ELISPOT assay will allow us to quantify not only the percentage of primary leukemia cells expressing IL-12 from the transduced IL-12 vector, but also will provide a distribution of IL-12 production levels. The assay will be developed to reliably yield at least 10% of the leukemia cells expressing at least 20000 pg/$10^6$/ml/2 hr. Primary cells will be frozen and thawed and retested to determine the stability of this distribution. Primary cells will also be irradiated and retested for the production and distribution of IL-12 levels. Clinical protocols using these populations would serve as autologous cell based vaccines to be used to prevent relapse in patients who achieve CR.

Example 6

Acute Lymphoblastic Leukemia (ALL)
Similarly as Described for CML, ALL Cells Transduced with a LV IL-12 Construct Will be Made and Tested.

Testing in Human ALL cells. Firstly, established ALL cell lines will be infected at various MOIs and clonal populations will be assessed for IL-12 expression in relation to vector copy number. It has been shown by the inventors that Jurkat cells (an ALL line) are readily and productively infected with recombinant LVs (21). Numerous clones from each pool will be derived and examined for vector copy and relative human IL-12 production. Cell viability of clones producing various levels of human IL-12 over time will be measured by thymidine incorporation assays. Cells will be cultured for many weeks and compared with original clones frozen initially after limiting dilution to determine if human IL-12 production changes over time. Vector stability will also be measured in these cells by repeat Southern Blot analyses. Secondly, primary human ALL cells are obtained from a minimum of 3-5 ALL donors initially to reduce reliance on a single sample. Here cells are infected at 2 or 3 different MOIs. Cells from each donor are handled separately to give information on the variability that can be expected. As above, human IL-12 production will be measured by ELISA in relation to vector copy number.

Additional pre-clinical data will be obtained. From a number of transduced K562 and Jurkat clonal lines, the sequence of the human IL-12 cDNA from the integrated provirus in genomic DNA will be determined after PCR amplification and subcloning to a stable plasmid. This will provide information on the stability of the vector itself and whether recombinations are occurring that could decrease protein expression levels from a given vector copy number. If consistent alterations are observed in a variety of clones such sequences could be mutated to reduce overlap or alter secondary mRNA structure to favor maintenance of fidelity. Further the vector integration site of cell populations by LM-PCR will be analysed to determine clonality. It will also be important to determine that the human IL-12 secreted by the transduced CML clones is functional. For this primary human DC cultures will be used to examine stimulation and the enhancement of T cell proliferation compared to controls.

It will be determined whether vector-transduced primary ALL cells that have undergone growth arrest (by very high dose irradiation, for example) in preparation for safe clinical infusions into patients are still able to secrete similar levels of human IL-12 compared to control cells. No differences are expected as others have shown stable expression of GM-CSF and CD40L, for example, in patient leukemia cells after irradiation (25). One group even reported enhanced transgene expression in leukemia cells after γ-irradiation (26). Also, the suicide gene component mentioned above is optionally added, and killing efficiency of bicistronically transduced primary ALL cells producing human IL-12 will be assessed after AZT addition at concentrations we have used before (21).

Administering IL-12 Expressing Cells to an ALL Subject

Acute Lymphoblastic Leukemia: It is estimated that 5,200 new patients will be diagnosed with ALL in the US in 2007, and 1,420 will die of the illness. ALL is the most is the most common type of leukemia in children with 61% of diagnoses made in individuals under age 20 (29). The overall 5-year relative survival rate for the period 1996-2003 was 64.0%. There was a slightly positive annual percentage change (0.3%) in ALL incidence for the period of 1985-2005 (29).

The malignant hematopoietic cells are lymphoid precursor cells. Cytogenetic abnormalities occur in ~70% of cases of ALL in adults but are not associated with a single translocation event as in CML. The standard treatment course has been given the terms induction, consolidation, maintenance, and CNS prophylaxis—but even with intensive therapy only 20-40% of adults with ALL are cured with current regimens. Therapy for ALL includes conventional chemotherapy (vincristine, anthracycline, cyclophosphamide, L-asparaginase etc.), radiation therapy and bone marrow transplant. Newer drugs have been developed including clofarabine, nelarabine, and dasatinib, but here responses have been relatively modest and toxicities remain an issue.

Imatinib has also been used in Philadelphia chromosome positive ALL. Imatinib has limited effectiveness in ALL treatment when used as a single agent, but several studies have shown improved outcomes when it is combined with standard chemotherapy (30). Clofarabine (Clolar®) was approved in December of 2004 for pediatric patients with relapsed or refractory ALL overall response rates average 25% (30). Nelarabine (Arranon®) was approved as an orphan drug by the FDA in October 2005 for treatment of T-cell ALL. Complete responses are reported in 54% of patients with T-cell ALL (30). Approximately 700 ALL patients per year in the US have T-cell ALL (30).

Drugs in development for ALL include Rituximab in Phase III, AMN107 and 852A both in Phase II, Nilotinib (Tasigna®) and AT9283 both in Phase I/II and KW-2449 in Phase I. Cell based therapies such as non myeloablative stem cell transplant and allogeneic umbilical cord blood transplantation are also in development. Drugs in trials for specific types of ALL include therapeutics directed to T-cell ALL (T-ALL) such as Alemtuzumab (Campath®), daclizumab and denileukin diftitox (Ontak®) all in Phase II and Similarly, a number of CML drugs in trials for Ph+ ALL such as MK0457 and Bortezomib (Velcade®) which are both in Phase II, SKI-606 in Phase I/II and INNO-406 in Phase I.

Clinical Use 50 ml of heparanized blood is collected from patients following REB approved informed consent. The blood is diluted with 110 ml of alpha medium and aliquoted in to 50 ml conical centrifuge tubes. Ficol hypaque is injected under the blood and the tubes are spun at 1600 rpm at 15 C for 20 minutes. The layer of mononuclear cells is removed and resuspended in 100 ml alpha medium with 5% FCS. The cells are spun at 1000 rpm for 10 minutes and then resuspended in 10 ml alpha medium with 5% FCS cells are then counted and then frozen for future use or distributed for fresh experiments. This would yield over 1×109 blasts from the peripheral blood of patients.

Blast cells are collected from the subject prior to chemotherapy when they are very high in numbers. The cells or a portion thereof are optionally frozen. The patient is treated with chemotherapy or other appropriate modality. Cells are then thawed if frozen, infectd with LV IL-12 and analyzed for the required level of expression (e.g the threshold level). Cells meeting this criteria are optionally irradiated, and reintroduced into the patient.

Where the vector construct comprises a safety gene component, cells are optionally not irradiated.

Further cells are optionally infected prior to freezing.

Adiministering IL-12 Expressing Cells to a Subject with CML

Chronic Myeloid Leukemia: It is estimated that 4,570 people in the US will be diagnosed with CML and 490 will die of this illness 2007 (30). There was a negative annual change in incidence (−2.6%) of CML for the period of 1997-2004 (30).

Current preferred first-line therapy involves treatment of CML patients with imatinib mesylate (Gleevec®). It has been reported that 4% of early-stage CML patients and a full 50% of advanced-stage CML patients develop resistance to imatinib (32). Imatinib mesylate treatment also requires life-long medication; the full effects of such prolonged administration of this agent (or others of this class) are not yet known. Gleevec can cause severe side effects such as cytopenias, particularly anemia, neutropenia, and thrombocytopenia; severe congestive heart failure and left ventricular dysfunction; severe hepatotoxicity; grade ¾ hemorrhage and gastrointestinal perforations including some that have been fatal. Along those lines, a recent study has shown that mice and human patients receiving imatinib mesylate demonstrate cardiotoxicity (2); although the overall prevalence of this severely adverse event has not yet been systematically verified and accurately quantitated.

Dasatinib (Sprycel®) has recently been introduced as a therapy for CML patients that have failed treatment with imatinib. Dasatinib can also produce severe and sometimes fatal side effects: thrombocytopenia, neutropenia, and anemia (NCI CTC Grade 3 or 4); severe hemorrhages including fatalities have occurred in a significant percentage of patients (1-7% depending on site of hemorrhage). Most bleeding events were associated with severe thrombocytopenia. Other side effects include severe fluid retention and cardiac effects (QT prolongation) (33).

Nilotinib (Tasigna®) has very recently been approved in the US as a new anti-cancer therapy for CML patients who are resistant or intolerant to treatment with imatinib. Similar to dasatinib, nilotinib can cause neutropenia and thrombocytopenia. Nilotinib also prolongs the QT interval and sudden deaths have been reported (34).

Other treatment options for patients with CML include conventional cytotoxic chemotherapy, interferon-alpha, bone marrow transplant and allogeneic stem cell transplant.

Drugs in development for CML include Lonafamib Phase III, LBH589 Phase II/III, AT9283 Phase I/II, MK0457 Phase II, Bortezomib (Velcade) Phase II. 852A Phase II, SKI-606 Phase I/II, allogeneic umbilical cord blood transplantation Phase II, XL228 Phase I, KW-2449 Phase I, INNO-406 Phase I and homoharringtonine (Ceflatonin®) which has recently completed Phase I/II (35).

Clinical Use 50 ml of heparanized blood is collected from patients following REB approved informed consent. The blood is diluted with 110 ml of alpha medium and aliquoted in to 50 ml conical centrifuge tubes. Ficol hypaque is injected under the blood and the tubes are spun at 1600 rpm at 15 C for 20 minutes. The layer of mononuclear cells is removed and resuspended in 100 ml alpha medium with 5% FCS. The cells are spun at 1000 rpm for 10 minutes and then resuspended in 10 ml alpha medium with 5% FCS cells are then counted and then frozen for future use or distributed for fresh experiments. This would yield over 1×109 blasts from the peripheral blood of patients.

Blast cells are collected from the subject prior to chemotherapy when they are very high in numbers. The cells or a portion thereof are optionally frozen. The patient is treated with chemotherapy or other appropriate modality. Cells are then thawed if frozen, infectd with LV IL-12 and analyzed for the required level of expression (e.g the threshold level). Cells meeting this criteria are optionally irradiated, and reintroduced into the patient.

Where the vector construct comprises a safety gene component, cells are optionally not irradiated.

Further cells are optionally infected prior to freezing.

Administering LV IL-12 to a CLL Patient

CLL B-CLL is the most common leukemia of adults with an expectation of ~16500 cases in NA this year (Estimates based on American Cancer Society and Canadian Cancer Society Reports). Remissions can be achieved with purine analogues and monoclonal antibody therapy however the diseases invariable progresses. Allogeneic stem cell transplants can be curative but many patients do not qualify for this treatment because of their age. The observation that GVL responses occur after stem cell transplantation confirms that an anti-leukemia immune response to CLL is possible. The slow progression of B-CLL also makes this disease attractive for immunotherapy approaches.

Clinical Use 50 ml of heparanized blood is collected from patients following REB approved informed consent. The blood is diluted with 110 ml of alpha medium and aliquoted in to 50 ml conical centrifuge tubes. Ficol hypaque is injected under the blood and the tubes are spun at 1600 rpm at 15 C for 20 minutes. The layer of mononuclear cells is removed and resuspended in 100 ml alpha medium with 5% FCS. The cells are spun at 1000 rpm for 10 minutes and then resuspended in 10 ml alpha medium with 5% FCS cells are then counted and then frozen for future use or distributed for fresh experiments.

This would yield over 1×109 blasts from the peripheral blood of patients.

Blast cells are collected from the subject prior to chemotherapy when they are very high in numbers. The cells or a portion thereof are optionally frozen. The patient is treated with chemotherapy or other appropriate modality. Cells are then thawed if frozen, infectd with LV IL-12 and analyzed for the required level of expression (e.g the threshold level). Cells meeting this criteria are optionally irradiated, and reintroduced into the patient.

Where the vector construct comprises a safety gene component, cells are optionally not irradiated.

Further cells are optionally infected prior to freezing.

References for Examples 4, 5 and 6

1. Piccaluga P P, Paolini S and Martinelli G. Tyrosine kinase inhibitors for the treatment of Philadelphia chromosome-positive adult acute lymphoblastic leukemia. *Cancer.* 110: 1178-1186 (2007).
2. Kerkela R, Grazette L, Yacobi R, Iliescu C, Patten R, Beahm C, Walters B, Shevtsov S, Pesant S, Clubb F J, Rosenzweig A, Salomon R N, Van Etten R A, Alroy J, Durand J B and Force T. Cardiotoxicity of the cancer therapeutic agent imatinib mesylate. *Nat. Med.* 12:908-916 (2006).
3. Portielje J E, Gratama J W, van Ojik H H, Stoter G and Kruit W H. IL-12: a promising adjuvant for cancer vaccination. *Cancer Immunol. Immunother.* 52:133-144 (2003).
4. Sasiain M C, de la Barrera S, Fink S, Finiasz M, Aleman M, Farina M H, Pizzariello G and Valdez R. Interferon-gamma (IFN-gamma) and tumour necrosis factor-alpha (TNF-alpha) are necessary in the early stages of induction of CD4 and CD8 cytotoxic T cells by Mycobacterium leprae heat shock protein (hsp) 65 kD. *Clin. Exp. Immunol.* 114:196-203 (1998).
5. Portielje J E, Lamers C H, Kruit W H, Sparreboom A, Bolhuis R L, Stoter G, Huber C and Gratama J W. Repeated administrations of interleukin (IL-)12 are associated with persistently elevated plasma levels of IL-10 and declining IFN-gamma, tumor necrosis factor-alpha, IL-6, and IL-8 responses. *Clin. Dancer Res.* 9:76-83 (2003).
6. Leonard J P, Sherman M L, Fisher G L, Buchanan L J, Larsen G, Atkins M B, Sosman J A, Dutcher J P, Vogelzang N J and Ryan J L. Effects of single-dose interleukin-12 exposure on interleukin-12-associated toxicity and interferon-gamma production. *Blood.* 90:2541-2548 (1997).
7. Sacco S, Heremans H, Echtenacher B, Buurman W A, Amraoui Z, Goldman M and Ghezzi P. Protective effect of a single interleukin-12 (IL-12) predose against the toxicity of subsequent chronic IL-12 in mice: role of cytokines and glucocorticoids. *Blood.* 90:4473-4479 (1997).
8. Masztalerz A, Van Rooijen N, Den Otter W and Everse L A. Mechanisms of macrophage cytotoxicity in IL-2 and IL-12 mediated tumour regression. *Cancer Immunol. Immunother.* 52:235-242 (2003).
9. Zagozdzon R, Golab J, Stoklosa T, Giermasz A, Nowicka D, Feleszko W, Lasek W and Jakobisiak M. Effective chemo-immunotherapy of L1210 leukemia in vivo using interleukin-12 combined with doxorubicin but not with cyclophosphamide, paclitaxel or cisplatin. *Int. J. Cancer.* 77:720-727 (1998).
10. Tatsumi T, Takehara T, Kanto T, Miyagi T, Kuzushita N, Sugimoto Y, Jinushi M, Kasahara A, Sasaki Y, Hori M and Hayashi N. Administration of interleukin-12 enhances the therapeutic efficacy of dendritic cell-based tumor vaccines in mouse hepatocellular carcinoma. *Cancer Res.* 61:7563-7567 (2001).
11. Nastala C L, Edington H D, McKinney T G, Tahara H, Nalesnik M A, Brunda M J, Gately M K, Wolf S F, Schreiber R D and Storkus W J. Recombinant IL-12 administration induces tumor regression in association with IFN-gamma production. *J. Immunol.* 153:1697-1706 (1994).
12. Dunussi-Joannopoulos K, Runyon K, Erickson J, Schaub R G, Hawley R G and Leonard J P. Vaccines with interleukin-12-transduced acute myeloid leukemia cells elicit very potent therapeutic and long-lasting protective immunity. *Blood.* 94:4263-4273 (1999).
13. Coughlin C M, Wysocka M, Trinchieri G and Lee W M. The effect of interleukin 12 desensitization on the antitumor efficacy of recombinant interleukin 12. *Cancer Res.* 57:2460-2467 (1997).
14. Asselin-Paturel C, Megherat S, Vergnon I, Echchakir H, Dorothee G, Blesson S, Gay F, Mami-Chouaib F and Chouaib S. Differential effect of high doses versus low doses of interleukin-12 on the adoptive transfer of human specific cytotoxic T lymphocyte in autologous lung tumors engrafted into severe combined immunodeficiency disease-nonobese diabetic mice: relation with interleukin-10 induction. *Cancer.* 91:113-122 (2001).
15. Gollob J A, Mier J W, Veenstra K, McDermott D F, Clancy D, Clancy M and Atkins M B. Phase I trial of twice-weekly intravenous interleukin 12 in patients with metastatic renal cell cancer or malignant melanoma: ability to maintain IFN-gamma induction is associated with clinical response. *Clin. Dancer Res.* 6:1678-1692 (2000).
16. Hoshino T, Jiang Y Z, Dunn D, Paul D, Qazilbash M, Cowan K, Wang J, Barrett J and Liu J. Transfection of interleukin-12 cDNAs into tumor cells induces cytotoxic immune responses against native tumor: implications for tumor vaccination. *Cancer Gene Ther.* 5:150-157 (1998).
17. Vigna E and Naldini L. Lentiviral vectors: excellent tools for experimental gene transfer and promising candidates for gene therapy. *J. Gene Med.* 2:308-316 (2000).
18. Logan A C, Lutzko C and Kohn D B. Advances in lentiviral vector design for gene-modification of hematopoietic stem cells. *Curr. Opin. Biotechnol.* 13:429-436 (2002).
19. Silvertown J D, Symes J C, Neschadim A, Nonaka T, Kao J C, Summerlee A J and Medin J A. Analog of H2 relaxin exhibits antagonistic properties and impairs prostate tumor growth. *FASEB J.* 21:754-765 (2007).
20. Yoshimitsu M, Sato T, Tao K, Walia J S, Rasaiah V I, Sleep G T, Murray G J, Poeppl A G, Underwood J, West L, Brady R O and Medin J A. Bioluminescent imaging of a marking transgene and correction of Fabry mice by neonatal injection of recombinant lentiviral vectors. *Proc. Natl. Acad. Sci. U.S.A.* 101:16909-16914 (2004).
21. Sato T, Neschadim A, Konrad M, Fowler D H, Lavie A and Medin J A. Engineered human tmpk/AZT as a novel enzyme/prodrug axis for suicide gene therapy. *Mol. Ther.* 15:962-970 (2007).
22. Baum C. I could die for you: new prospects for suicide in gene therapy. *Mol. Ther.* 15:848-849 (2007).

23. Levine B L, Humeau L M, Boyer J, MacGregor R R, Rebello T, Lu X, Binder G K, Slepushkin V, Lemiale F, Mascola J R, Bushman F D, Dropulic B and June C H. Gene transfer in humans using a conditionally replicating lentiviral vector. *Proc. Natl. Acad. Sci. U.S.A.* 103:17372-17377 (2006).
24. Yoshimitsu M, Higuchi K, Ramsubir S, Nonaka T, Rasaiah V I, Siatskas C, Liang S B, Murray G J, Brady R O and Medin J A. Efficient correction of Fabry mice and patient cells mediated by lentiviral transduction of hematopoietic stem/progenitor cells. *Gene Ther.* 14:256-265 (2007).
25. Dessureault S, Noyes D, Lee D, Dunn M, Janssen W, Cantor A, Sotomayor E, Messina J and Antonia S J. A phase-I trial using a universal GM-CSF-producing and CD40L-expressing bystander cell line (GM. DD40L) in the formulation of autologous tumor cell-based vaccines for cancer patients with stage IV disease. *Ann. Surq. Oncol.* 14:869-884 (2007).
26. Vereecque R, Saudemont A, Wickham T J, Gonzalez R, Hetuin D, Fenaux P and Quesnel B. Gamma-irradiation enhances transgene expression in leukemic cells. *Gene Ther.* 10:227-233 (2003).
27. Eisterer W, Jiang X, Christ O, Glimm H, Lee KH, Pang E, Lambie K, Shaw G, Holyoake T L, Petzer A L, Auewarakul C, Barnett M J, Eaves C J and Eaves A C. Different subsets of primary chronic myeloid leukemia stem cells engraft immunodeficient mice and produce a model of the human disease. *Leukemia.* 19:435-441 (2005).
28. Del Vecchio M, Bajetta E, Canova S, Lotze M T, Wesa A, Parmiani G and Anichini A. Interleukin-12: biological properties and clinical application. *Clin. Dancer Res.* 13:4677-4685 (2007).
29. National Cancer Institute. SEER Cancer Statistics Review. 2007: (2007).
30. Seiter K. Acute Lymphoblastic Leukemia. (2006).
31. Redaelli A, Stephens J M, Laskin B L, Pashos C L and Botteman M F. The burden and outcomes associated with four leukemias: AML, ALL, C LL and CML. *Expert Rev. Anticancer Ther.* 3:311-329 (2003).
32. Piccaluga P P, Martinelli G and Baccarani M. Advances in the treatment for haematological malignancies. *Expert Opin. Pharmacother.* 7:721-732 (2006).
33. Dasatinib (Sprycel®) Drug Product Label.
34. Nilotinib (Tasigna®) Drug Product Label.
35. ChemGenix Pharmaceuticals. ChemGenix Pharmaceuticals Press Release (2007).
36. Centers for Medicare & Medicaid Services, the US Department of Health and Human Services. 2004 Report. (2004).
37. Frost & Sullivan. U.S. Gene Therapy Markets. (2005).
38. Gene Therapy Clinical Trials Worldwide online database maintained by the Journal of Gene Medicine. Gene therapy clinical trials numbers query search. (2007).

Example 7

Treating Solid Tumors

Solid tumors are removed partially of fully from a subject. The solid tumor is optionally any respectable tumor. The tumor is optionally a renal cell cancer, melanoma or prostate cancer.

Single cell suspensions are obtained and cells are transduced or transfected with an IL-12 vector construct such as LV hIL-12. Transfected or transduced cells are optionally irradiated to induce growth arrest and prevent cell division. Transduced cells comprising vector constructs comprising an activator polynucleotide such as a modified tmpk molecule are not irradiated as cells expressing the activator polynucleotide can be killed by administration of the prodrug.

A population of cells including transduced cancer cells is administered to the subject from which the cancer was derived. The population of cells is administered, intradermally or subcutaneously about once a week, once every two weeks, or about once a month for a 3 month period. Approximately $1 \times 10^6$ to $1 \times 10^8$ cells are administered.

The subject is monitored for an anti-cancer immune response and cancer progression.

Example 8

Research Models and Systems

Determine the critical aspects of initiating anti-leukemia responses in the murine system. The in vivo induction of anti-leukemia immunity using in vitro models will be studied. DCs mature in culture when exposed to 70Z/3-IL-12 cells only in the presence of spleen cells. Untransduced 70Z/3 cells do not mirror this effect. Selected populations of spleen cells will be systematically removed to determine which spleen cells are responsible for the observed effects. Antibodies specific for subpopulations of T cells, NK cells, and macrophages, will be used in combination with either M ACS or FACS for depletion and/or enrichment. These experiments will be conducted in transwell plates which allow the physical separation of the various cell types to identify critical cell-cell interactions. DC maturation (increased expression of CD80) as our prime read out has been used. However, it is possible that DC maturation in the presence of 70Z/3 cells will be followed by activation of specific T cell populations. The in vitro system will be used to determine if T cell responses are initiated and, if so, the nature of those responses. Cytokine production typical of Th1 induction (such as IFNγ) as well as the appearance CD4$^+$ and or CD8$^+$ mature T cells specific for 70Z/3 cells will be monitored. 70Z/3 specific T cell clones will be expanded and their cell surface phenotype will be characterized. Their cytotoxic potential in Cr$^{51}$ release assays using 70Z/3 cells as targets will be tested.

The established in vivo model will also be used to explore the induction of protective immunity. In particular, adoptive transfer experiments will be undertaken to determine if CD4$^+$ cells can confer immunity and if so if these cells are CD4$^+$ CTL or NKT cells. These cells will be isolated and cloned in vitro after they arise in the mice to establish their growth properties and mechanism of cytotoxicity. By comparing the induction of immunity to AML to our current ALL model, we will study why some cancers are more immunogenic that others.

With this background knowledge we will initiate IL-12 transduction experiments using established human leukemia cell lines representing different classes of leukemia. These include K562, CES1, OCIAML1, OCIAML2, Jurkat, Raji. The Medin lab has already shown that both K562 and Jurkat are readily infected with LV vectors in past experiments. The cell lines will be transduced in bulk culture after which clones will be selected by limit dilution. The clones will be examined for cell proliferation by thymidine incorporation assays and for IL-12 production by ELISA. The stability of the IL-12 production will be determined after extended cell culture times as well as after several freeze/thaw cycles. Repeat Southern blot analysis will be used to determine vector copy number and stability as well.

Human in vitro assay. Established cell lines and primary samples will also be used to develop in vitro assays similar to those underway in the murine system. In vitro culture conditions that support human DCs and T cell subsets have been developed. Using these as a starting point the effects of IL-12 producing cell lines and primary samples in short term assays will be monitored. We will establish the ability of IL-12 producing cell lines and primary leukemia samples to influence the maturation of human DCs in the presence and absence of selected T cell subsets. We will monitor cell surface markers such as CD80 for DC maturation and IFNγγ secretion for induction of Th1 responses. If evidence of an IR is detected, CD4 and CD8 subsets will be isolated and tested for anti-leukemia cytotoxicity and specificity.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

References (Except Examples 4-6)

1. Guilhot, F., Roy, L., Guilhot, J., and Millot, F. (2004). Interferon therapy in chronic myelogenous leukemia. *Hematol Oncol Clin North Am* 18: 585-603, viii.
2. Pyrhonen, S. O. (2004). Systemic therapy in metastatic renal cell carcinoma. *Scand J Surg* 93: 156-161.
3. Nemunaitis, J. (2003). GVAX (GMCSF gene modified tumor vaccine) in advanced stage non small cell lung cancer. *J Control Release* 91: 225-231.
4. Portielje, J. E., Gratama, J. W., van Ojik, H. H., Stoter, G., and Kruit, W. H. (2003). IL-12: a promising adjuvant for cancer vaccination. *Cancer Immunol Immunother* 52: 133-144.
5. Sasiain, M. C., et al. (1998). Interferon-gamma (IFN-gamma) and tumour necrosis factor-alpha (TNF-alpha) are necessary in the early stages of induction of CD4 and CD8 cytotoxic T cells by Mycobacterium leprae heat shock protein (hsp) 65 kD. *Clinical and experimental immunology* 114: 196-203.
6. Portielje, J. E., et al. (2003). Repeated administrations of interleukin (IL)-12 are associated with persistently elevated plasma levels of IL-10 and declining IFN-gamma, tumor necrosis factor-alpha, IL-6, and IL-8 responses. *Clin Cancer Res* 9: 76-83.
7. Sacco, S., et al. (1997). Protective effect of a single interleukin-12 (IL-12) predose against the toxicity of subsequent chronic IL-12 in mice: role of cytokines and glucocorticoids. *Blood* 90: 4473-4479.
8. Leonard, J. P., et al. (1997). Effects of single-dose interleukin-12 exposure on interleukin-12-associated toxicity and interferon-gamma production. *Blood* 90: 2541-2548.
9. Masztalerz, A., Van Rooijen, N., Den Otter, W., and Everse, L. A. (2003). Mechanisms of macrophage cytotoxicity in IL-2 and IL-12 mediated tumour regression. *Cancer Immunol Immunother* 52: 235-242.
10. Zagozdzon, R., et al. (1998). Effective chemo-immunotherapy of L1210 leukemia in vivo using interleukin-12 combined with doxorubicin but not with cyclophosphamide, paclitaxel or cisplatin. *Int J Cancer* 77: 720-727.
11. Tatsumi, T., et al. (2001). Administration of interleukin-12 enhances the therapeutic efficacy of dendritic cell-based tumor vaccines in mouse hepatocellular carcinoma. *Cancer research* 61: 7563-7567.
12. Nastala, C. L., et al. (1994). Recombinant IL-12 administration induces tumor regression in association with IFN-gamma production. *J Immunol* 153: 1697-1706.
13. Dunussi-Joannopoulos, K., Runyon, K., Erickson, J., Schaub, R. G., Hawley, R. G., and Leonard, J. P. (1999). Vaccines with interleukin-12-transduced acute myeloid leukemia cells elicit very potent therapeutic and long-lasting protective immunity. *Blood* 94: 4263-4273.
14. Atkins, M. B., et al. (1997). Phase I evaluation of intravenous recombinant human interleukin 12 in patients with advanced malignancies. *Clin Cancer Res* 3: 409-417.
15. Kang, W. K., et al. (2001). Interleukin 12 gene therapy of cancer by peritumoral injection of transduced autologous fibroblasts: outcome of a phase I study. *Human gene therapy* 12: 671-684.
16. Mazzolini, G., et al. (2005). Intratumoral injection of dendritic cells engineered to secrete interleukin-12 by recombinant adenovirus in patients with metastatic gastrointestinal carcinomas. *J Clin Oncol* 23: 999-1010.
17. Dohnal, A. M., Witt, V., Hugel, H., Holter, W., Gadner, H., and Felzmann, T. (2007). Phase I study of tumor Ag-loaded IL-12 secreting semi-mature DC for the treatment of pediatric cancer. *Cytotherapy* 9: 755-770.
18. Gollob, J. A., et al. (2000). Phase I trial of twice-weekly intravenous interleukin 12 in patients with metastatic renal cell cancer or malignant melanoma: ability to maintain IFN-gamma induction is associated with clinical response. *Clin Cancer Res* 6: 1678-1692.
19. Coughlin, C. M., Wysocka, M., Trinchieri, G., and Lee, W. M. (1997). The effect of interleukin 12 desensitization on the antitumor efficacy of recombinant interleukin 12. *Cancer research* 57: 2460-2467.
20. Asselin-Paturel, C., et al. (2001). Differential effect of high doses versus low doses of interleukin-12 on the adoptive transfer of human specific cytotoxic T lymphocyte in autologous lung tumors engrafted into severe combined immunodeficiency disease-nonobese diabetic mice: relation with interleukin-10 induction. *Cancer* 91: 113-122.
21. Saudemont, A., et al. (2002). Gene transfer of CD154 and IL12 cDNA induces an anti-leukemic immunity in a murine model of acute leukemia. *Leukemia* 16: 1637-1644.
22. Tahara, H., et al. (1994). Fibroblasts genetically engineered to secrete interleukin 12 can suppress tumor growth and induce antitumor immunity to a murine melanoma in vivo. *Cancer research* 54: 182-189.
23. Tahara, H., et al. (1995). Effective eradication of established murine tumors with IL-12 gene therapy using a polycistronic retroviral vector. *J Immunol* 154: 6466-6474.
24. Zitvogel, L., et al. (1995). Cancer immunotherapy of established tumors with IL-12. Effective delivery by genetically engineered fibroblasts. *J Immunol* 155: 1393-1403.
25. Gambotto, A., et al. (1999). Induction of antitumor immunity by direct intratumoral injection of a recombinant adenovirus vector expressing interleukin-12. *Cancer gene therapy* 6: 45-53.

26. Tatsumi, T., et al. (2007). Injection of IL-12 gene-transduced dendritic cells into mouse liver tumor lesions activates both innate and acquired immunity. *Gene therapy* 14: 863-871.
27. Barker, S. E., et al. (2007). Immunotherapy for neuroblastoma using syngeneic fibroblasts transfected with IL-2 and IL-12. *British journal of cancer* 97: 210-217.
28. Paige, C. J., Kincade, P. W., and Ralph, P. (1978). Murine B cell leukemia line with inducible surface immunoglobulin expression. *J Immunol* 121: 641-647.
29. Yoshimitsu, M., et al. (2004). Bioluminescent imaging of a marking transgene and correction of Fabry mice by neonatal injection of recombinant lentiviral vectors. *Proc Natl Acad Sci USA* 101: 16909-16914.
30. Dull, T., et al. (1998). A third-generation lentivirus vector with a conditional packaging system. *J Virol* 72: 8463-8471.
31. Silvertown, J. D., Walia, J. S., Summerlee, A. J., and Medin, J. A. (2006). Functional expression of mouse relaxin and mouse relaxin-3 in the lung from an Ebola virus glycoprotein-pseudotyped lentivirus via tracheal delivery. *Endocrinology* 147: 3797-3808.
32. Wilson, S. D., McCay, J. A., Butterworth, L. F., Munson, A. E., and White, K. L., Jr. (2001). Correlation of suppressed natural killer cell activity with altered host resistance models in B6C3F1 mice. *Toxicol Appl Pharmacol* 177: 208-218.

33. Alli, R. S., and Khar, A. (2004). Interleukin-12 secreted by mature dendritic cells mediates activation of NK cell function. *FEBS Lett* 559: 71-76.

34. Redlinger, R. E., Jr., Shimizu, T., Remy, T., Alber, S., Watkins, S. C., and Barksdale, E. M., Jr. (2003). Cellular mechanisms of interleukin-12-mediated neuroblastoma regression. *J Pediatr Surg* 38: 199-204.

35. Alatrash, G., et al. (2004). Clinical and immunologic effects of subcutaneously administered interleukin-12 and interferon alfa-2b: phase I trial of patients with metastatic renal cell carcinoma or malignant melanoma. *J Clin Oncol* 22: 2891-2900.

36. Blachere, N. E., et al. (2006). IL-2 is required for the activation of memory CD8+ T cells via antigen cross-presentation. *J Immunol* 176: 7288-7300.

37. Coughlin, C. M., et al. (1998). Interleukin-12 and interleukin-18 synergistically induce murine tumor regression which involves inhibition of angiogenesis. *J Clin Invest* 101: 1441-1452.

38. Robertson, M. J., et al. (2006). Clinical and biological effects of recombinant human interleukin-18 administered by intravenous infusion to patients with advanced cancer. *Clin Cancer Res* 12: 4265-4273.

39. Labbe, A., Tran, A. H., and Paige, C. J. (2006). Murine model of immune-mediated rejection of the acute lymphoblastic leukemia 70Z/3. *J Immunol* 176: 5354-5361.

40. Zajac, A. J., Quinn, D. G., Cohen, P. L., and Frelinger, J. A. (1996). Fas-dependent CD4+ cytotoxic T-cell-mediated pathogenesis during virus infection. *Proc Natl Acad Sci USA* 93: 14730-14735.

41. Matsushita, M., et al. (2006). Possible involvement of allogeneic antigens recognised by donor-derived CD4 cytotoxic T cells in selective GVL effects after stem cell transplantation of patients with haematological malignancy. *Br J Haematol* 132: 56-65.

42. Corthay, A., et al. (2005). Primary antitumor immune response mediated by CD4+ T cells. *Immunity* 22: 371-383.

43. Hombach, A., Kohler, H., Rappl, G., and Abken, H. (2006). Human CD4+ T cells lyse target cells via granzyme/perforin upon circumvention of MHC class II restriction by an antibody-like immunoreceptor. *J Immunol* 177: 5668-5675.

44. Zhang, Y., et al. (2007). Th1 cell adjuvant therapy combined with tumor vaccination: a novel strategy for promoting CTL responses while avoiding the accumulation of Tregs. *International immunology* 19: 151-161.

45. Perez-Diez, A., et al. (2007). CD4 cells can be more efficient at tumor rejection than CD8 cells. *Blood.*

46. Chung, Y., Qin, H., Kang, C. Y., Kim, S., Kwak, L. W., and Dong, C. (2007). An NKT-mediated autologous vaccine generates CD4 T-cell dependent potent antilymphoma immunity. *Blood* 110: 2013-2019.

Sequences

SEQ ID NO: 1
pHR'.cPPT.EF.CD19ΔTmpkF105YR200A.WPRE.SIN.
AATTACCTGTGGTTTCATTTACTCTAAACCTGTGATTCCTCTGAATTATTTTCATTTTAAAGAAATTGT
ATTTGTTAAATATGTACTACAAACTTAGTAGTTGGAAGGGCTAATTCACTCCCAAAGAAGACAAGATAT
CCTTGATCTGTGGATCTACCACACACAAGGCTACTTCCCTGATTAGCAGAACTACACACCAGGGCCAGG
GGTCAGATATCCACTGACCTTTGGATGGTGCTACAAGCTAGTACCAGTTGAGCCAGATAAGGTAGAAGA
GGCCAATAAAGGAGAGAACACCAGCTTGTTACACCCTGTGAGCCTGCATGGGATGGATGACCCGGAGAG
AGAAGTGTTAGAGTGGAGGTTTGACAGCCGCCTAGCATTTCATCACGTGGCCCGAGAGCTGCATCCGGA
GTACTTCAAGAACTGCTGATATCGAGCTTGCTACAAGGGACTTTCCGCTGGGGACTTTCCAGGGAGGCG
TGGCCTGGGCGGGACTGGGGAGTGGCGAGCCCTCAGATCCTGCATATAAGCAGCTGCTTTTTGCCTGTA
CTGGGTCTCTCTGGTTAGACCAGATCTGAGCCTGGGAGCTCTCTGGCTAACTAGGGAACCCACTGCTTA
AGCCTCAATAAAGCTTGCCTTGAGTGCTTCAAGTAGTGTGTGCCCGTCTGTTGTGTGACTCTGGTAACT
AGAGATCCCTCAGACCCTTTTAGTCAGTGTGGAAAATCTCTAGCAGTGGCGCCCGAACAGGGACTTGAA
AGCGAAAGGGAAACCAGAGGAGCTCTCTCGACGCAGGACTCGGCTTGCTGAAGCGCGCACGGCAAGAGG
CGAGGGGCGGCGACTGGTGAGTACGCCAAAAATTTTGACTAGCGGAGGCTAGAAGGAGAGAGATGGGTG
CGAGAGCGTCAGTATTAAGCGGGGGAGAATTAGATCGCGATGGGAAAAAATTCGGTTAAGGCCAGGGGG
AAAGAAAAAATATAAATTAAAACATATAGTATGGGCAAGCAGGGAGCTAGAACGATTCGCAGTTAATCC
TGGCCTGTTAGAAACATCAGAAGGCTGTAGACAAATACTGGGACAGCTACAACCATCCCTTCAGACAGG
ATCAGAAGAACTTAGATCATTATATAATACAGTAGCAACCCTCTATTGTGTGCATCAAAGGATAGAGAT
AAAAGACACCAAGGAAGCTTTAGACAAGATAGAGGAAGAGCAAAACAAAAGTAAGACCACCGCACAGCA
AGCGGCCGCTGATCTTCAGACCTGGAGGAGGAGATATGAGGGACAATTGGAGAAGTGAATTATATAAAT
ATAAAGTAGTAAAAATTGAACCATTAGGAGTAGCACCCACCAAGGCAAAGAGAAGAGTGGTGCAGAGAG
AAAAAAGAGCAGTGGGAATAGGAGCTTTGTTCCTTGGGTTCTTGGGAGCAGCAGGAAGCACTATGGGCG
CAGCGTCAATGACGCTGACGGTACAGGCCAGACAATTATTGTCTGGTATAGTGCAGCAGCAGAACAATT
TGCTGAGGGCTATTGAGGCGCAACAGCATCTGTTGCAACTCACAGTCTGGGGCATCAAGCAGCTCCAGG
CAAGAATCCTGGCTGTGGAAAGATACCTAAAGGATCAACAGCTCCTGGGGATTTGGGGTTGCTCTGGAA
AACTCATTTGCACCACTGCTGTGCCTTGGAATGCTAGTTGGAGTAATAAATCTCTGGAACAGATTTGGA
ATCACACGACCTGGATGGAGTGGGACAGAGAAATTAACAATTACACAAGCTTAATACACTCCTTAATTG

| Sequences |
| --- |
| AAGAATCGCAAAACCAGCAAGAAAAGAATGAACAAGAATTATTGGAATTAGATAAATGGGCAAGTTTGT
GGAATTGGTTTAACATAACAAATTGGCTGTGGTATATAAAATTATTCATAATGATAGTAGGAGGCTTGG
TAGGTTTAAGAATAGTTTTTGCTGTACTTTCTATAGTGAATAGAGTTAGGCAGGGATATTCACCATTAT
CGTTTCAGACCCACCTCCCAACCCCGAGGGGACCCGACAGGCCCGAAGGAATAGAAGAAGAAGGTGGAG
AGAGAGACAGAGACAGATCCATTCGATTAGTGAACGGATCTCGACGGTATCGATTTTAAAAGAAAAGGG
GGGATTGGGGGGTACAGTGCAGGGGAAAGAATAGTAGACATAATAGCAACAGACATACAAACTAAAGAA
TTACAAAAACAAATTACAAAAATTCAAAATTTTATCGATAAGCTTTGCAAAGATGGATAAAGTTTTAAA
CAGAGAGGAATCTTTGCAGCTAATGGACCTTCTAGGTCTTGAAAGGAGTGGGAATTGGCTCCGGTGCCC
GTCAGTGGGCAGAGCGCACATCGCCCACAGTCCCCGAGAAGTTGGGGGGAGGGGTCGGCAATTGAACCG
GTGCCTAGAGAAGGTGGCGCGGGGTAAACTGGGAAAGTGATGTCGTGTACTGGCTCCGCCTTTTTCCCG
AGGGTGGGGGAGAACCGTATATAAGTGCAGTAGTCGCCGTGAACGTTCTTTTTCGCAACGGGTTTGCCG
CCAGAACACAGGTAAGTGCCGTGTGTGGTTCCCGCGGGCCTGGCCTCTTTACGGGTTATGGCCCTTGCG
TGCCTTGAATTACTTCCACCTGGCTGCAGTACGTGATTCTTGATCCCGAGCTTCGGGTTGGAAGTGGGT
GGGAGAGTTCGAGGCCTTGCGCTTAAGGAGCCCCTTCGCCTCGTGCTTGAGTTGAGGCCTGGCCTGGGC
GCTGGGGCCGCCGCGTGCGAATCTGGTGGCACCTTCGCGCCTGTCTCGCTGCTTTCGATAAGTCTCTAG
CCATTTAAAATTTTTGATGACCTGCTGCGACGCTTTTTTTCTGGCAGATAGTCTTGTAAATGCGGGCC
AAGATCTGCACACTGGTATTTCGGTTTTTGGGGCCGCGGGCGGCGACGGGGCCCGTGCGTCCCAGCGCA
CATGTTCGGCGAGGCGGGGCCTGCGAGCGCGGCCACCGAGAATCGGACGGGGGTAGTCTCAAGCTGGCC
GGCCTGCTCTGGTGCCTGGCCTCGCGCCGCCGTGTATCGCCCCGCCCTGGGCGGCAAGGCTGGCCCGGT
CGGCACCAGTTGCGTGAGCGGAAAGATGGCCGCTTCCCGGCCTGCTGCAGGGAGCTCAAAATGGAGGA
CGCGGCGCTCGGGAGAGCGGGCGGGTGAGTCACCCACACAAAGGAAAAGGGCCTTTCCGTCCTCAGCCG
TCGCTTCATGTGACTCCACGGAGTACCGGGCGCCGTCCAGGCACCTCGATTAGTTCTCGAGCTTTTGGA
GTACGTCGTCTTTAGGTTGGGGGAGGGGTTTTATGCGATGGAGTTTCCCCACACTGAGTGGGTGGAGA
CTGAAGTTAGGCCAGCTTGGCACTTGATGTAATTCTCCTTGGAAATTTGCCCTTTTTGAGTTTGGATCTT
GGTTCATTCTCAAGCCTCAGACAGTGGTTCAAAGTTTTTTTCTTCCATTTTCAGGTGTCGTGAGGAATTC
ATGCCACCTCCTCGCCTCCTCTTCTTCCTCCTCTTCCTCACCCCCATGGAAGTCAGGCCCGAGGAACCT
CTAGTGGTGAAGGTGGAAGAGGGAGATAACGCTGTGCTGCAGTGCCTCAAGGGGACCTCAGATGGCCCC
ACTCAGCAGCTGACCTGGTCTCGGGAGTCCCGCTTAAACCCTTCTTAAAACTCAGCCTGGGGCTGCCA
GGCCTGGGAATCCACATGAGGCCCCTGGCATCCTGGCTTTTCATCTTCAACGTCTCTCAACAGATGGGG
GGCTTCTACCTGTGCCAGCCGGGGCCCCCCTCTGAGAAGGCCTGGCAGCCTGGCTGGACAGTCAATGTG
GAGGGCAGCGGGGAGCTGTTCCGGTGGAATGTTTCGGACCTAGGTGGCCTGGGCTGTGGCCTGAAGAAC
AGGTCCTCAGAGGGCCCCAGCTCCCCTTCCGGGAAGCTCATGAGCCCCAAGCTGTATGTGTGGGCCAAA
GACCGCCCTGAGATCTGGGAGGGAGAGCCTCCGTGTGTCCCACCGAGGGACAGCCTGAACCAGAGCCTC
AGCCAGGACCTCACCATGGCCCTGCTCCACACTCTGGCTGTCCTGTGGGGTACCCCCTGACTCTGTG
TCCAGGGGCCCCTCTCCTGGACCCATGTGCACCCCAAGGGGCCTAAGTCATTGCTGAGCCTAGAGCTG
AAGGACGATCGCCCGGCCAGAGATATGTGGGTAATGGACGGGTCTGTTGTTGCCCGGGCCACAGCT
CAAGACGCTGGAAAGTATTATTGTCACCGTGGCAACCTGACCATGTCATTCCACCTGGAGATCACTGCT
CGGCCAGTACTATGGCACTGGCTGCTGAGGACTGGTGGCTGGAAGGTCTCAGCTGTGACTTTGGCTTAT
CTGATCTTCTGCCTGTGTTCCCTTGTGGGCATTCTTCATCTTGCCGGCGGGCTGCAGGGATGGCGGCC
CGGCGCGGGGCTCTCATAGTGCTGGAGGGCGTGGACCGCGCCGAACTGCTCCGGTTCCCGGAAAGATCAACTGAAATC
GGCAAACTTCTGAGTTCCTACTTGCAAAAGAAAAGTGACGTGGAGGATCACTCGGTGCACCTGCTTTTT
TCTGCAAATCGCTGGGAACAAGTGCCGTTAATTAAGGAAAAGTTGAGCCAGGGCGtGACCCTCGTCGTG
GACAGATACGCATTTTCTGGTGTGGCCTACACaGGTGCCAAGGAGAATTTTTCCCTAGACTGGTGTAAA
CAGCCAGACGTGGGCCTTCCCAAACCCGACCTGGTCCTGTTCCTCCAGTTACAGCTGGCGGATCTGCC
AAGCGGGGAGCGTTTGGCCATGAGCGCTATGAGAACGGGGCTTTCCAGGAGCGGGCGCTCCGGTGTTTC
CACCAGCTCATGAAAGACACGACTTTGAACTGGAAGATGGTGGATGCTTCCAAAAGCATCGAAGCTGTC
CATGAGGACATCCGCGTGCTCTCTGAGGACGCCATCGCCACTGCCACAGAGAAGCCGCTGGGGGAGCTA
TGGAAGTGAGGATCCAAGCTTCAATTGGTCACTCGACAATCAACCTCTGGATTACAAAATTTGTGAA
AGATTGACTGGTATTCTTAACTATGTTGCTCCTTTTACGCTATGTGGATACGCTGCTTTAATGCCTTTG
TATCATGCTATTGCTTCCCGTATGGCTTTCATTTTCTCCTCTTGTATAAATCCTGGTTGCTGTCTCTTT
TATGAGGAGTTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCGGGACTTTCGCTTTCCCCCTCCCTATTGCC
ACGGCGGAACTCATCGCCGCCTGCCTTGCCCGCTGCTGGACAGGGGCTCGGCTGTTGGGCACTGACAAT
TCCGTGGTGTTGTCGGGGAAGCTGACGTCCTTTCCATGGCTGCTCGCCTGTGTTGCCACCTGGATTCTG
CGCGGGACGTCCTTCTGCTACGTCCCTTCGGCCCTCAATCCAGCGGACCTTCCTTCCCGCGGCCTGCTG
CCGGCTCTGCGGCCTCTTCCGCGTCTTCGCCTTCGCCCTCAGACGAGTCGGATCTCCCTTTGGGCCGCC
TCCCCGCCTGCTCGAGACCTAGAAAAACATGGAGCAATCACAAGTAGCAATACAGCAGCTACCAATGCT
GATTGTGCCTGGCTAGAAGCACAAGAGGAGGAGGAGGTGGGTTTTCCAGTCACACCTCAGGTACCTTTA
AGACCAATGACTTACAAGGCAGCTGTAGATCTTAGCCACTTTTTAAAAGAAAAGGGGGGACTGGAAGGG
CTAATTCACTCCCAACGAAGACAAGATCTGCTTTTTGCTTGTACTGGGTCTCTCTGGTTAGACCAGATC
TGAGCCTGGGAGCTCTCTGGCTAACTAGGGAACCCACTGCTTAAGCCTCAATAAAGCTTGCCTTGAGTG
CTTCAAGTAGTGTGTGCCCGTCTGTTGTGTGACTCTGGTAACTAGAGATCCCTCAGACCCTTTTAGTCA
GTGTGGAAAATCTCTAGCAGTAGTAGTTCATGTCATCTTATTATTCAGTATTTATAACTTGCAAAGAAA
TGAATATCAGAGAGTGAGAGGCCTTGACATTATAATAGATTTAGCAGGAATTGAACTAGGAGTGGAGCA
CACAGGCAAAGCTGCAGAAGTACTTGGAAGAAGCCACCAGAGATACTCACGATTCTGCACATACCTGCC
TAATCCCAGATCCTAAGGATTACATTAAGTTTACTAACATTTATATAATGATTTATAGTTTAAAGTATA
AACTTATCTAATTTACTATTCTGACAGATATTAATTAATCCTCAAATATCATAAGAGATGATTACTATT
ATCCCCATTTAACACAAGAGGAAACTGAGAGGGAAAGATGTTGAAGTAATTTTCCCACAATTACAGCAT
CCGTTAGTTACGACTCTATGATCTTCTGACACAAATTCCATTTACTCCTCACCCTATGACTCAGTCGAA
TATATCAAAGTTATGGACATTTATGCTAAGTAACAAATTACCCTTTATATAGTAAATACTAGTAGATT
GAGAGAAGAAATTGTTTCAAACCTGAATAGCTTCAAGAAGAAGAGAAGTGAGGATAAGAATAACAGTT
GTCATTTAACAAGTTTTAACAAGTAACTTGGTTAGAAAGGGATTCAAATGCATAAAGCAAGGGATAAAT
TTTTCTGGCAACAAGACTATACAATATAACCTTAAATATGACTTCAAATAATTGTTGGAACTTGATAAA
ACTAATTAAATATTATTGAAGATTATCAATATTATAAATGTAATTTACTTTTAAAAGGGAACATAGAA
ATGTGTATCATTAGAGTAGAAAACAATCCTTATTATCACAATTTGTCAAAACAAGTTTGTTATTAACAC
AAGTAGAATACTGCATTCAATTAAGTTGACTGCAGATTTTGTGTTTTGTTAAAATTAGAAAGAGATAAC |

| Sequences |
| --- |
| AACAATTTGAATTATTGAAAGTAACATGTAAATAGTTCTACATACGTTCTTTTGACATCTTGTTCAATC |
| ATTGATCGAAGTTCTTTATCTTGGAAGAATTTGTTCCAAAGACTCTGAAATAAGGAAAACAATCTATTA |
| TATAGTCTCACACCTTTGTTTTACTTTTAGTGATTTCAATTTAATAATGTAAATGGTTAAAATTTATTC |
| TTCTCTGAGATCATTTCACATTGCAGATAGAAAACCTGAGACTGGGGTAATTTTTATTAAAATCTAATT |
| TAATCTCAGAAACACATCTTTATTCTAACATCAATTTTTCCAGTTTGATATTATCATATAAAGTCAGCC |
| TTCCTCATCTGCAGGTTCCACAACAAAAATCCAACCAACTGTGGATCAAAAATATTGGGAAAAAATTAA |
| AAATAGCAATACAACAATAAAAAAATACAAATCAGAAAAACAGCACAGTATAACAACTTTATTTAGCAT |
| TTACAATCTATTAGGTATTATAAGTAATCTAGAATTAATTCCGTGTATTCTATAGTGTCACCTAAATCG |
| TATGTGTATGATACATAAGGTTATGTATTAATTGTAGCCGCGTTCTAACGACAATATGTACAAGCCTAA |
| TTGTGTAGCATCTGGCTTACTGAAGCAGACCCTATCATCTCTCGTAAACTGCCGTCAGAGTCGGTTT |
| GGTTGGACGAACCTTCTGAGTTTCTGGTAACGCCGTCCCGCACCCGGAAATGGTCAGCGAACCAATCAG |
| CAGGGTCATCGCTAGCCAGATCCTCTACGCCGGACGCATCGTGGCCGGCATCACCGGCGCCACAGGTGC |
| GGTTGCTGGCGCCTATATCGCCGACATCACCGATGGGGAAGATCGGGCTCGCCACTTCGGGCTCATGAG |
| CGCTTGTTTCGGCGTGGGTATGGTGGCAGGCCCCGTGGCCGGGGGACTGTTGGGCGCCATCTCCTTGCA |
| TGCACCATTCCTTGCGGCGGCGGTGCTCAACGGCCTCAACCTACTACTGGGCTGCTTCCTAATGCAGGA |
| GTCGCATAAGGGAGAGCGTCGAATGGTGCACTCTCAGTACAATCTGCTCTGATGCCGCATAGTTAAGCC |
| AGCCCCGACACCCGCCAACACCCGCTGACGCGCCCTGACGGGCTTGTCTGCTCCCGGCATCCGCTTACA |
| GACAAGCTGTGACCGTCTCCGGGAGCTGCATGTGTCAGAGGTTTTCACCGTCATCACCGAAACGCGCGA |
| GACGAAAGGGCCTCGTGATACGCCTATTTTTATAGGTTAATGTCATGATAATAATGGTTTCTTAGACGT |
| CAGGTGGCACTTTTCGGGGAAATGTGCGCGGAACCCCTATTTGTTTATTTTTCTAAATACATTCAAATA |
| TGTATCCGCTCATGAGACAATAACCCTGATAAATGCTTCAATAATATTGAAAAAGGAAGAGTATGAGTA |
| TTCAACATTTCCGTGTCGCCCTTATTCCCTTTTTTGCGGCATTTTGCCTTCCTGTTTTTGCTCACCCAG |
| AAACGCTGGTGAAAGTAAAAGATGCTGAAGATCAGTTGGGTGCACGAGTGGGTTACATCGAACTGGATC |
| TCAACAGCGGTAAGATCCTTGAGAGTTTTCGCCCCGAAGAACGTTTTCCAATGATGAGCACTTTTAAAG |
| TTCTGCTATGTGGCGCGGTATTATCCCGTATTGACGCCGGGCAAGAGCAACTCGGTCGCCGCATACACT |
| ATTCTCAGAATGACTTGGTTGAGTACTCACCAGTCACAGAAAAGCATCTTACGGATGGCATGACAGTAA |
| GAGAATTATGCAGTGCTGCCATAACCATGAGTGATAACACTGCGGCCAACTTACTTCTGACAACGATCG |
| GAGGACCGAAGGAGCTAACCGCTTTTTTGCACAACATGGGGGATCATGTAACTCGCCTTGATCGTTGGG |
| AACCGGAGCTGAATGAAGCCATACCAAACGACGAGCGTGACACCACGATGCCTGTAGCAATGGCAACAA |
| CGTTGCGCAAACTATTAACTGGCGAACTACTTACTCTAGCTTCCCGGCAACAATTAATAGACTGGATGG |
| AGGCGGATAAAGTTGCAGGACCACTTCTGCGCTCGGCCCTTCCGGCTGGCTGGTTTATTGCTGATAAAT |
| CTGGAGCCGGTGAGCGTGGGTCTCGCGGTATCATTGCAGCACTGGGGCCAGATGGTAAGCCCTCCCGTA |
| TCGTAGTTATCTACACGACGGGGAGTCAGGCAACTATGGATGAACGAAATAGACAGATCGCTGAGATAG |
| GTGCCTCACTGATTAAGCATTGGTAACTGTCAGACCAAGTTTACTCATATATACTTTAGATTGATTTAA |
| AACTTCATTTTTAATTTAAAAGGATCTAGGTGAAGATCCTTTTTGATAATCTCATGACCAAAATCCCTT |
| AACGTGAGTTTTCGTTCCACTGAGCGTCAGACCCCGTAGAAAAGATCAAAGGATCTTCTTGAGATCCTT |
| TTTTTCTGCGCGTAATCTGCTGCTTGCAAACAAAAAAACCACCGCTACCAGCGGTGGTTTGTTTGCCGG |
| ATCAAGAGCTACCAACTCTTTTTCCGAAGGTAACTGGCTTCAGCAGAGCGCAGATACCAAATACTGTTC |
| TTCTAGTGTAGCCGTAGTTAGGCCACCACTTCAAGAACTCTGTAGCACCGCCTACATACCTCGCTCTGC |
| TAATCCTGTTACCAGTGGCTGCTGCCAGTGGCGATAAGTCGTGTCTTACCGGGTTGGACTCAAGACGAT |
| AGTTACCGGATAAGGCGCAGCGGTCGGGCTGAACGGGGGGTTCGTGCACACAGCCCAGCTTGGAGCGAA |
| CGACCTACACCGAACTGAGATACCTACAGCGTGAGCTATGAGAAAGCGCCACGCTTCCCGAAGGGAGAA |
| AGGCGGACAGGTATCCGGTAAGCGGCAGGGTCGGAACAGGAGAGCGCACGAGGGAGCTTCCAGGGGGAA |
| ACGCCTGGTATCTTTATAGTCCTGTCGGGTTTCGCCACCTCTGACTTGAGCGTCGATTTTTGTGATGCT |
| CGTCAGGGGGGCGGAGCCTATGGAAAAACGCCAGCAACGCGGCCTTTTTACGGTTCCTGGCCTTTTGCT |
| GGCCTTTTGCTCACATGTTCTTTCCTGCGTTATCCCCTGATTCTGTGGATAACCGTATTACCGCCTTTG |
| AGTGAGCTGATACCGCTCGCCGCAGCCGAACGACCGAGCGCAGCGAGTCAGTGAGCGAGGAAGCGGAAG |
| AGCGCCCAATACGCAAACCGCCTCTCCCCGCGCGTTGGCCGATTCATTAATGCAGCTGTGGAATGTGTG |
| TCAGTTAGGGTGTGGAAAGTCCCCAGGCTCCCCAGCAGGCAGAAGTATGCAAAGCATGCATCTCAATTA |
| GTCAGCAACCAGGTGTGGAAAGTCCCCAGGCTCCCCAGCAGGCAGAAGTATGCAAAGCATGCATCTCAA |
| TTAGTCAGCAACCATAGTCCCGCCCTAACTCCGCCCATCCCGCCCCTAACTCCGCCCAGTTCCGCCCA |
| TTCTCCGCCCCATGGCTGACTAATTTTTTTTATTTATGCAGAGGCCGAGGCCGCCTCGGCCTCTGAGCT |
| ATTCCAGAAGTAGTGAGGAGGCTTTTTTGGAGGCCTAGGCTTTTGCAAAAAGCTTGGACACAAGACAGG |
| CTTGCGAGATATGTTTGAGAATACCACTTTATCCCGCGTCAGGGAGAGGCAGTGCGTAAAAAGACGCGG |
| ACTCATGTGAAATACTGGTTTTTAGTGCGCCAGATCTCTATAATCTCGCGCAACCTATTTTCCCCTCGA |
| ACACTTTTTAAGCCGTAGATAAACAGGCTGGGACACTTCACATGAGCGAAAAATACATCGTCACCTGGG |
| ACATGTTGCAGATCCATGCACGTAAACTCGCAAGCCGACTGATGCCTTCTGAACAATGGAAAGGCATTA |
| TTGCCGTAAGCCGTGGCGGTCTGTACCGGGTGCGTTACTGGCGCGTGAACTGGGTATTCGTCATGTCGA |
| TACCGTTTGTATTTCCAGCTACGATCACGACAACCAGCGCGAGCTTAAAGTGCTGAAACGCGCAGAAGG |
| CGATGGCGAAGGCTTCATCGTTATTGATGACCTGGTGGATACCGGTGGTACTGCGGTTGCGATTCGTGA |
| AATGTATCCAAAAGCGCACTTTGTCACCATCTTCGCAAAACCGGCTGGTCGTCCGCTGGTTGATGACTA |
| TGTTGTTGATATCCCGCAAGATACCTGGATTGAACAGCCGTGGGATATGGGCGTCGTATTCGTCCCGCC |
| AATCTCCGGTCGCTAATCTTTTCAACGCCTGGCACTGCCGGGCGTTGTTCTTTTTAACTTCAGGCGGGT |
| TACAATAGTTTCCAGTAAGTATTCTGGAGGCTGCATCCATGACACAGGCAAACCTGAGCGAAACCCTGT |
| TCAAACCCCGCTTTAAACATCCTGAAACCTCGACGCTAGTCCGCCGCTTTAATCACGGCGCACAACCGC |
| CTGTGCAGTCGGCCCTTGATGGTAAAACCATCCCTCACTGGTGCATGATTAACCGTCTGATGTGGA |
| TCTGGCGCGGCATTGACCCACGCGAAATCCTCGACGTCCAGGCACGTATTGTGATGAGCGATGCCGAAC |
| GTACCGACGATGATTTATACGATACGGTGATTGGCTACCGTGGCGGCAACTGGATTTATGAGTGGGCCC |
| CGGATCTTTGTGAAGGAACCTTACTTCTGTGGTGTGACATAATTGGACAAACTACCTACAGAGATTTAA |
| AGCTCTAAGGTAAATATAAAATTTTTAAGTGTATAATGTGTTAAACTACTGATTCTAATTGTTTGTGTA |
| TTTTAGATTCCAACCTATGGAACTGATGAATGGGAGCAGTGGTGGAATGCCTTTAATGAGGAAAACCTG |
| TTTTGCTCAGAAGAAATGCCATCTAGTGATGATGAGGCTACTGCTGACTCTCAACATTCTACTCCTCCA |
| AAAAAGAAGAGAAAGGTAGAAGACCCCAAGGACTTTCCTTCAGAATTGCTAAGTTTTTTGAGTCATGCT |
| GTGTTTAGTAATAGAACTCTTGCTTGCTTTGCTATTTACACCACAAAGGAAAAGCTGCACTGCTATAC |
| AAGAAAATTATGGAAAAATATTCTGTAACCTTTATAAGTAGGCATAACAGTTATAATCATAACATACTG |
| TTTTTTCTTACTCCACACAGGCATAGAGTGTCTGCTATTAATAACTATGCTCAAAAATTGTGTACCTTT |
| AGCTTTTTAATTTGTAAAGGGGTTAATAAGGAATATTTGATGTATAGTGCCTTGACTAGAGATCATAAT |

| Sequences |
|---|
| CAGCCATACCACATTTGTAGAGGTTTTACTTGCTTTAAAAAACCTCCCACACCTCCCCCTGAACCTGAA
ACATAAAATGAATGCAATTGTTGTTGTTAACTTGTTTATTGCAGCTTATAATGGTTACAAATAAAGCAA
TAGCATCACAAATTTCACAAATAAAGCATTTTTTTCACTGCATTCTAGTTGTGGTTTGTCCAAACTCAT
CAATGTATCTTATCATGTCTGGATCAACTGGATAACTCAAGCTAACCAAAATCATCCCAAACTTCCCAC
CCCATACCCTATTACCACTGCC | pHR Backbone

| |
|---|
| AATTACCTGTGGTTTCATTTACTCTAAACCTGTGATTCCTCTGAATTATTTTCATTTTAAAGAAATTGT
ATTTGTTAAATATGTACTACAAACTTAGTAGTTGGAAGGGCTAATTCACTCCCAAAGAAGACAAGATAT
CCTTGATCTGTGGATCTACCACACACAAGGCTACTTCCCTGATTAGCAGAACTACACACCAGGGCCAGG
GGTCAGATATCCACTGACCTTTGGATGGTGCTACAAGCTAGTACCAGTTGAGCCAGATAAGGTAGAAGA
GGCCAATAAAGGAGAGAACACCAGCTTGTTACACCCTGTGAGCCTGCATGGGATGGATGACCCGGAGAG
AGAAGTGTTAGAGTGGAGGTTTGACAGCCGCCTAGCATTTCATCACGTGGCCCGAGAGCTGCATCCGGA
GTACTTCAAGAACTGCTGATATCGAGCTTGCTACAAGGGACTTTCCGCTGGGGACTTTCCAGGGAGGCG
TGGCCTGGGCGGGACTGGGGAGTGGCGAGCCCTCAGATCCTGCATATAAGCAGCTGCTTTTTGCCTGTA
CTGGGTCTCTCTGGTTAGACCAGATCTGAGCCTGGGAGCTCTCTGGCTAACTAGGGAACCCACTGCTTA
AGCCTCAATAAAGCTTGCCTTGAGTGCTTCAAGTAGTGTGTGCCCGTCTGTTGTGTGACTCTGGTAACT
AGAGATCCCTCAGACCCTTTTAGTCAGTGTGGAAAATCTCTAGCAGTGGCGCCCGAACAGGGACTTGAA
AGCGAAAGGGAAACCAGAGGAGCTCTCTCGACGCAGGACTCGGCTTGCTGAAGCGCGCACGGCAAGAGG
CGAGGGGCGGCGACTGGTGAGTACGCCAAAAATTTTGACTAGCGGAGGCTAGAAGGAGAGAGATGGGTG
CGAGAGCGTCAGTATTAAGCGGGGAGAATTAGATCGCGATGGGAAAAAATTCGGTTAAGGCCAGGGGGA
AAGAAAAAATATAAATTAAAACATATAGTATGGGCAAGCAGGGAGCTAGAACGATTCGCAGTTAATCC
TGGCCTGTTAGAAACATCAGAAGGCTGTAGACAAATACTGGGACAGCTACAACCATCCCTTCAGACAGG
ATCAGAAGAACTTAGATCATTATATAATACAGTAGCAACCCTCTATTGTGTGCATCAAAGGATAGAGAT
AAAAGACACCAAGGAAGCTTTAGACAAGATAGAGGAAGAGCAAAACAAAAGTAAGACCACCGCACAGCA
AGCGGCCGCTGATCTTCAGACCTGGAGGAGGAGATATGAGGGACAATTGGAGAAGTGAATTATATAAAT
ATAAAGTAGTAAAAATTGAACCATTAGGAGTAGCACCCACCAAGGCAAAGAGAAGAGTGGTGCAGAGAG
AAAAAAGAGCAGTGGGAATAGGAGCTTTGTTCCTTGGGTTCTTGGGAGCAGCAGGAAGCACTATGGGCG
CAGCGTCAATGACGCTGACGGTACAGGCCAGACAATTATTGTCTGGTATAGTGCAGCAGCAGAACAATT
TGCTGAGGGCTATTGAGGCGCAACAGCATCTGTTGCAACTCACAGTCTGGGGCATCAAGCAGCTCCAGG
CAAGAATCCTGGCTGTGGAAAGATACCTAAAGGATCAACAGCTCCTGGGGATTTGGGGTTGCTCTGGAA
AACTCATTTGCACCACTGCTGTGCCTTGGAATGCTAGTTGGAGTAATAAATCTCTGGAACAGATTTGGA
ATCACACGACCTGGATGGAGTGGGACAGAGAAATTAACAATTACACAAGCTTAATACACTCCTTAATTG
AAGAATCGCAAAACCAGCAAGAAAAGAATGAACAAGAATTATTGGAATTAGATAAATGGGCAAGTTTGT
GGAATTGGTTTAACATAACAAATTGGCTGTGGTATATAAAATTATTCATAATGATAGTAGGAGGCTTGG
TAGGTTTAAGAATAGTTTTTGCTGTACTTTCTATAGTGAATAGAGTTAGGCAGGGATATTCACCATTAT
CGTTTCAGACCCACCTCCCAACCCCGAGGGGACCCGACAGGCCCGAAGGAATAGAAGAAGAAGGTGGAG
AGAGAGACAGAGACAGATCCATTCGATTAGTGAACGGATCTCGACGGTATCGATTTTAAAAGAAAAGGG
GGGATTGGGGGGTACAGTGCAGGGGAAAGAATAGTAGACATAATAGCAACAGACATACAAACTAAAGAA
TTACAAAAACAAATTACAAAAATTCAAAATTTTATCGATAAGCTTTGCAAAGATGGATAAAGTTTTAAA
CAGAGAGGAATCTTTGCAGCTAATGGACCTTCTAGGTCTTGAAAGGAGTGGGAATTGGCTCCGGTGCCC
GTCAGTGGGCAGAGCGCACATCGCCCACAGTCCCCGAGAAGTTGGGGGGAGGGGTCGGCAATTGAACCG
GTGCCTAGAGAAGGTGGCGCGGGGTAAACTGGGAAAGTGATGTCGTGTACTGGCTCCGCCTTTTTCCCG
AGGGTGGGGGAGAACCGTATATAAGTGCAGTAGTCGCCGTGAACGTTCTTTTTCGCAACGGGTTTGCCG
CCAGAACACAGGTAAGTGCCGTGTGTGGTTCCCGCGGGCCTGGCCTCTTTACGGGTTATGGCCCTTGCG
TGCCTTGAATTACTTCCACCTGGCTGCAGTACGTGATTCTTGATCCCGAGCTTCGGGTTGGAAGTGGGT
GGGAGAGTTCGAGGCCTTGCGCTTAAGGAGCCCCTTCGCCTCGTGCTTGAGTTGAGGCCTGGCCTGGGC
GCTGGGGCCGCCGCGTGCGAATCTGGTGGCACCTTCGCGCCTGTCTCGCTGCTTTCGATAAGTCTCTAG
CCATTTAAAATTTTTGATGACCTGCTGCGACGCTTTTTTTCTGGCAAGATAGTCTTGTAAATGCGGGCC
AAGATCTGCACACTGGTATTTCGGTTTTTGGGGCCGCGGGCGGCGACGGGCCCGTGCGTCCCAGCGCA
CATGTTCGGCGAGGCGGGGCCTGCGAGCGCGGCCACCGAGAATCGGACGGGGGTAGTCTCAAGCTGGCC
GGCCTGCTCTGGTGCCTGGCCTCGCGCCGCCGTGTATCGCCCCGCCCTGGGCGGCAAGGCTGGCCCGGT
CGGCACCAGTTGCGTGAGCGGAAAGATGGCCGCTTCCCGGCCCTGCTGCAGGGAGCTCAAATGGAGGA
CGCGGCGCTCGGGAGAGCGGGCGGGTGAGTCACCCACACAAAGGAAAAGGGCCTTTCCGTCCTCAGCCG
TCGCTTCATGTGACTCCACGGAGTACCGGGCGCCGTCCAGGCACCTCGATTAGTTCTCGAGCTTTTGGA
GTACGTCGTCTTTAGGTTGGGGGGAGGGGTTTTATGCGATGGAGTTTCCCCACACTGAGTGGGTGGAGA
CTGAAGTTAGGCCAGCTTGGCACTTGATGTAATTCTCCTTGGAATTTGCCCTTTTTGAGTTTGGATCTT
GGTTCATTCTCAAGCCTCAGACAGTGGTTCAAAGTTTTTTTCTTCCATTTCAGGTGTCGTGAGAATTAC
CTGTGGTTTCATTTACTCTAAACCTGTGATTCCTCTGAATTATTTTCATTTTAAAGAAATTGTATTTGT
TAAATATGTACTACAAACTTAGTAGTTGGAAGGGCTAATTCACTCCCAAAGAAGACAAGATATCCTTGA
TCTGTGGATCTACCACACACAAGGCTACTTCCCTGATTAGCAGAACTACACACCAGGGCCAGGGGTCAG
ATATCCACTGACCTTTGGATGGTGCTACAAGCTAGTACCAGTTGAGCCAGATAAGGTAGAAGAGGCCAA
TAAAGGAGAGAACACCAGCTTGTTACACCCTGTGAGCCTGCATGGGATGGATGACCCGGAGAGAGAAGT
GTTAGAGTGGAGGTTTGACAGCCGCCTAGCATTTCATCACGTGGCCCGAGAGCTGCATCCGGAGTACTT
CAAGAACTGCTGATATCGAGCTTGCTACAAGGGACTTTCCGCTGGGGACTTTCCAGGGAGGCGTGGCCT
GGGCGGGACTGGGGAGTGGCGAGCCCTCAGATCCTGCATATAAGCAGCTGCTTTTTGCCTGTACTGGGT
CTCTCTGGTTAGACCAGATCTGAGCCTGGGAGCTCTCTGGCTAACTAGGGAACCCACTGCTTAAGCCTC
AATAAAGCTTGCCTTGAGTGCTTCAAGTAGTGTGTGCCCGTCTGTTGTGTGACTCTGGTAACTAGAGAT
CCCTCAGACCCTTTTAGTCAGTGTGGAAAATCTCTAGCAGTGGCGCCCGAACAGGGACTTGAAAGCGAA
AGGGAAACCAGAGGAGCTCTCTCGACGCAGGACTCGGCTTGCTGAAGCGCGCACGGCAAGAGGCGAGGG
GCGGCGACTGGTGAGTACGCCAAAAATTTTGACTAGCGGAGGCTAGAAGGAGAGAGATGGGTGCGAGAG
CGTCAGTATTAAGCGGGGAGAATTAGATCGCGATGGGAAAAAATTCGGTTAAGGCCAGGGGGAAAGAA
AAAATATAAATTAAAACATATAGTATGGGCAAGCAGGGAGCTAGAACGATTCGCAGTTAATCCTGGCCT
GTTAGAAACATCAGAAGGCTGTAGACAAATACTGGGACAGCTACAACCATCCCTTCAGACAGGATCAGA
AGAACTTAGATCATTATATAATACAGTAGCAACCCTCTATTGTGTGCATCAAAGGATAGAGATAAAAGA
CACCAAGGAAGCTTTAGACAAGATAGAGGAAGAGCAAAACAAAAGTAAGACCACCGCACAGCAAGCGGC
CGCTGATCTTCAGACCTGGAGGAGGAGATATGAGGGACAATTGGAGAAGTGAATTATATAAATATAAAG |

-continued

| Sequences |
|---|
| TAGTAAAAATTGAACCATTAGGAGTAGCACCCACCAAGGCAAAGAGAAGAGTGGTGCAGAGAGAAAAA |
| GAGCAGTGGGAATAGGAGCTTTGTTCCTTGGGTTCTTGGGAGCAGCAGGAAGCACTATGGGCGCAGCGT |
| CAATGACGCTGACGGTACAGGCCAGACAATTATTGTCTGGTATAGTGCAGCAGCAGAACAATTTGCTGA |
| GGGCTATTGAGGCGCAACAGCATCTGTTGCAACTCACAGTCTGGGGCATCAAGCAGCTCCAGGCAAGAA |
| TCCTGGCTGTGGAAAGATACCTAAAGGATCAACAGCTCCTGGGGATTTGGGGTTGCTCTGGAAAACTCA |
| TTTGCACCACTGCTGTGCCTTGGAATGCTAGTTGGAGTAATAAATCTCTGGAACAGATTTGGAATCACA |
| CGACCTGGATGGAGTGGGACAGAGAAATTAACAATTACACAAGCTTAATACACTCCTTAATTGAAGAAT |
| CGCAAAACCAGCAAGAAAAGAATGAACAAGAATTATTGGAATTAGATAAATGGGCAAGTTTGTGGAATT |
| GGTTTAACATAACAAATTGGCTGTGGTATATAAAATTATTCATAATGATAGTAGGAGGCTTGGTAGGTT |
| TAAGAATAGTTTTTGCTGTACTTTCTATAGTGAATAGAGTTAGGCAGGGATATTCACCATTATCGTTTC |
| AGACCCACCTCCCAACCCCGAGGGGACCCGACAGGCCCGAAGGAATAGAAGAAGAAGGTGGAGAGAGAG |
| ACAGAGACAGATCCATTCGATTAGTGAACGGATCTCGACGGTATCGATTTTAAAAGAAAAGGGGGGATT |
| GGGGGGTACAGTGCAGGGGAAAGAATAGTAGACATAATAGCAACAGACATACAAACTAAAGAATTACAA |
| AAACAAATTACAAAAATTCAAAATTTTTATCGATAAGCTTTGCAAAGATGGATAAAGTTTTAAACAGAGA |
| GGAATCTTTGCAGCTAATGGACCTTCTAGGTCTTGAAAGGAGTGGGAATTGGCTCCGGTGCCCGTCAGT |
| GGGCAGAGCGCACATCGCCCACAGTCCCCGAGAAGTTGGGGGGCAGGGGTCGGCAATTGAACCGGTGCCT |
| AGAGAAGGTGGCGCGGGGTAAACTGGGAAAGTGATGTCGTGTACTGGCTCCGCCTTTTTCCCGAGGGTG |
| GGGGAGAACCGTATATAAGTGCAGTAGTCGCCGTGAACGTTCTTTTTCGCAACGGGTTTGCCGCCAGAA |
| CACAGGTAAGTGCCGTGTGTGGTTCCCGCGGGCCTGGCCTCTTTACGGGTTATGGCCCTTGCGTGCCTT |
| GAATTACTTCCACCTGGCTGCAGTACGTGATTCTTGATCCCGAGCTTCGGGTTGGAAGTGGGTGGGAGA |
| GTTCGAGGCCTTGCGCTTAAGGAGCCCCTTCGCCTCGTGCTTGAGTTGAGGCCTGGCCTGGGCGCTGGG |
| GCCGCCGCGTGCGAATCTGGTGGCACCTTCGCGCCTGTCTCGCTGCTTTCGATAAGTCTCTAGCCATTT |
| AAAATTTTTGATGACCTGCTGCGACGCTTTTTTTCTGGCAAGATAGTCTTGTAAATGCGGGCCAAGATC |
| TGCACACTGGTATTTCGGTTTTTGGGGCCGCGGGCGGCGACGGGGCCCGTGCGTCCCAGCGCACATGTT |
| CGGCGAGGCGGGGCCTGCGAGCGCGGCCACCGAGAATCGGACGGGGGTAGTCTCAAGCTGGCCGGCCTG |
| CTCTGGTGCCTGGCCTCGCGCCGCCGTGTATCGCCCCGCCCTGGGCGGCAAGGCTGGCCCGGTCGGCAC |
| CAGTTGCGTGAGCGGAAAGATGGCCGCTTCCCGGCCCTGCTGCAGGGAGCTCAAAATGGAGGACGCGGC |
| GCTCGGGAGAGCGGGCGGGTGAGTCACCCACACAAAGGAAAAGGGCCTTTCCGTCCTCAGCCGTCGCTT |
| CATGTGACTCCACGGAGTACCGGGCGCCGTCCAGGCACCTCGATTAGTTCTCGAGCTTTTGGAGTACGT |
| CGTCTTTAGGTTGGGGGAGGGGTTTTATGCGATGGAGTTTCCCCACACTGAGTGGGTGGAGACTGAAG |
| TTAGGCCAGCTTGGCACTTGATGTAATTCTCCTTGGAATTTGCCCTTTTTGAGTTTGGATCTTGGTTCA |
| TTCTCAAGCCTCAGACAGTGGTTCAAAGTTTTTTTCTTCCATTTCAGGTGTCGTGAGGAATTCGGATCC |
| AAGCTTCAATTGTGGTCACTCGACAATCAACCTCTGGATTACAAAATTTGTGAAAGATTGACTGGTATT |
| CTTAACTATGTTGCTCCTTTTACGCTATGTGGATACGCTGCTTTAATGCCTTTGTATCATGCTATTGCT |
| TCCCGTATGGCTTTCATTTTCTCCTCCTTGTATAAATCCTGGTTGCTGTCTCTTTATGAGGAGTTGTGG |
| CCCGTTGTCAGGCAACGTGGCGTGGTGTGCACTGTGTTTGCTGACGCAACCCCCACTGGTTGGGGCATT |
| GCCACCACCTGTCAGCTCCTTTCCGGGACTTTCGCTTTCCCCCTCCCTATTGCCACGGCGGAACTCATC |
| GCCGCCTGCCTTGCCCGCTGCTGGACAGGGGCTCGGCTGTTGGGCACTGACAATTCCGTGGTGTTGTCG |
| GGGAAGCTGACGTCCTTTCCATGGCTGCTCGCCTGTGTTGCCACCTGGATTCTGCGCGGGACGTCCTTC |
| TGCTACGTCCCTTCGGCCCTCAATCCAGCGGACCTTCCTTCCCGCGGCCTGCTGCCGGCTCTGCGGCCT |
| CTTCCGCGTCTTCGCCTTCGCCCTCAGACGAGTCGGATCTCCCTTTGGGCCGCCTCCCCGCTGCTCGA |
| GACCTAGAAAAACATGGAGCAATCACAAGTAGCAATACAGCAGCTACCAATGCTGATTGTGCCTGGCTA |
| GAAGCACAAGAGGAGGAGGAGGTGGGTTTTCCAGTCACACCTCAGGTACCTTTAAGACCAATGACTTAC |
| AAGGCAGCTGTAGATCTTAGCCACTTTTTAAAAGAAAAGGGGGGACTGGAAGGGCTAATTCACTCCCAA |
| CGAAGACAAGATCTGCTTTTTGCTTGTACTGGGTCTCTCTGGTTAGACCAGATCTGAGCCTGGGAGCTC |
| TCTGGCTAACTAGGGAACCCACTGCTTAAGCCTCAATAAAGCTTGCCTTGAGTGCTTCAAGTAGTGTGT |
| GCCCGTCTGTTGTGTGACTCTGGTAACTAGAGATCCCTCAGACCCTTTTAGTCAGTGTGGAAAATCTCT |
| AGCAGTAGTAGTTCATGTCATCTTATTATTCAGTATTTATAACTTGCAAAGAAATGAATATCAGAGAGT |
| GAGAGGCCTTGACATTATAATAGATTTAGCAGGAATTGAACTAGGAGTGGAGCACACAGGCAAAGCTGC |
| AGAAGTACTTGGAAGAAGCCACCAGAGATACTCACGATTCTGCACATACCTGGCTAATCCCAGATCCTA |
| AGGATTACATTAAGTTTACTAACATTTATATAATGATTTATAGTTTAAAGTATAAACTTATCTAATTTA |
| CTATTCTGACAGATATTAATTAATCCTCAAATATCATAAGAGATGATTACTATTATCCCCATTTAACAC |
| AAGAGGAAACTGAGAGGGAAAGATGTTGAAGTAATTTTCCCACAATTACAGCATCCGTTAGTTACGACT |
| CTATGATCTTCTGACACAAATTCCATTTACTCCTCACCCTATGACTCAGTCGAATATATCAAAGTTATG |
| GACATTATGCTAAGTAACAAATTACCCTTTTATATAGTAAATACTGAGTAGATTGAGAGAAGAAATTGT |
| TTGCAAACCTGAATAGCTTCAAGAAGAAGAGAAGTGAGGATAAGAATAACAGTTGTCATTTAACAAGTT |
| TTAACAAGTAACTTGGTTAGAAAGGGATTCAAATGCATAAAGCAAGGGATAAATTTTTCTGGCAACAAG |
| ACTATACAATATAACCTTAAATATGACTTCAAATAATTGTTGGAACTTGATAAAACTAATTAAATATTA |
| TTGAAGATTATCAATATTATAAATGTAATTTACTTTTAAAAGGGAACATAGAAATGTGTATCATTAGA |
| GTAGAAAACAATCCTTATTATCACAATTTGTCAAAACAAGTTGTTATTAACACAAGTAGAATACTGCA |
| TTCAATTAAGTTGACTGCAGATTTTGTGTTTTGTTAAAATTAGAAAGGATAACAACAATTTGAATTAT |
| TGAAAGTAACATGTAAATAGTTCTACATACGTTCTTTTGACATCTTGTTCAATCATTGATCGAAGTTCT |
| TTATCTTGGAAGAATTTGTTCCAAAGACTCTGAAATAAGGAAAACAATCTATTATATAGTCTCACACCT |
| TTGTTTTACTTTTAGTGATTTCAATTTAATAATGTAAATGGTTAAAATTTATTCTTCTCTGAGATCATT |
| TCACATTGCAGATAGAAAACCTGAGACTGGGGTAATTTTTATTAAAATCTAATTTAATCTCAGAAACAC |
| ATCTTTATTCTAACATCAATTTTTCCAGTTTGATATTATCATATAAAGTTCAGCCTTCCTCATCTGCAGG |
| TTCCACAACAAAAATCCAACCAACTGTGGATCAAAAATATTGGGAAAAAATTAAAAATAGCAATACAAC |
| AATAAAAAAATACAAATCAGAAAAACAGCACAGTATAACAACTTTATTTAGCATTTACAATCTATTAGG |
| TATTATAAGTAATCTAGAATTAATTCCGTGTATTCTATAGTGTCACCTAAATCGTATGTGTATGATACA |
| TAAGGTTATGTATTAATTGTAGCCGCGTTCTAACGACAATATGTACAAGCCTAATTGTGTAGCATCTGG |
| CTTACTGAAGCAGACCCTATCATCTCTCGTAAACTGCCGTCAGAGTCGGTTTGGTTGGACGAACCTT |
| CTGAGTTTCTGGTAACGCCGTCCCGCACCCGAAATGGTCAGCGAACCAATCAGCAGGGTCATCGCTAG |
| CCAGATCCTCTACGCCGGACGCATCGTGGCCGGCATCACCGGCGCCACAGGTGCGGTTGCTGGCGCCTA |
| TATCGCCGACATCACCGATGGGGAAGATCGGGCTCGCCACTTCGGGCTCATGAGCGCTTGTTTCGGCGT |
| GGGTATGGTGGCAGGCCCCGTGGCCGGGGGACTGTTGGGCGCCATCTCCTTGCATGCACCATTCCTTGC |
| GGCGGCGGTGCTCAACGGCCTCAACCTACTACTGGGCTGCTTCCTAATGCAGGAGTCGCATAAGGGAGA |
| GCGTCGAATGGTGCACTCTCAGTACAATCTGCTCTGATGCCGCATAGTTAAGCCAGCCCCGACACCCGC |

| Sequences |
|---|
| CAACACCCGCTGACGCGCCCTGACGGGCTTGTCTGCTCCCGGCATCCGCTTACAGACAAGCTGTGACCG |
| TCTCCGGGAGCTGCATGTGTCAGAGGTTTTCACCGTCATCACCGAAACGCGCGAGACGAAAGGGCCTCG |
| TGATACGCCTATTTTTATAGGTTAATGTCATGATAATAATGGTTTCTTAGACGTCAGGTGGCACTTTTC |
| GGGGAAATGTGCGCGGAACCCCTATTTGTTTATTTTTCTAAATACATTCAAATATGTATCCGCTCATGA |
| GACAATAACCCTGATAAATGCTTCAATAATATTGAAAAAGGAAGAGTATGAGTATTCAACATTTCCGTG |
| TCGCCCTTATTCCCTTTTTTGCGGCATTTTGCCTTCCTGTTTTTGCTCACCCAGAAACGCTGGTGAAAG |
| TAAAAGATGCTGAAGATCAGTTGGGTGCACGAGTGGGTTACATCGAACTGGATCTCAACAGCGGTAAGA |
| TCCTTGAGAGTTTTCGCCCCGAAGAACGTTTTCCAATGATGAGCACTTTTAAAGTTCTGCTATGTGGCG |
| CGGTATTATCCCGTATTGACGCCGGGCAAGAGCAACTCGGTCGCCGCATACACTATTCTCAGAATGACT |
| TGGTTGAGTACTCACCAGTCACAGAAAAGCATCTTACGGATGGCATGACAGTAAGAGAATTATGCAGTG |
| CTGCCATAACCATGAGTGATAACACTGCGGCCAACTTACTTCTGACAACGATCGGAGGACCGAAGGAGC |
| TAACCGCTTTTTTGCACAACATGGGGGATCATGTAACTCGCCTTGATCGTTGGGAACCGGAGCTGAATG |
| AAGCCATACCAAACGACGAGCGTGACACCACGATGCCTGTAGCAATGGCAACAACGTTGCGCAAACTAT |
| TAACTGGCGAACTACTTACTCTAGCTTCCCGGCAACAATTAATAGACTGGATGGAGGCGGATAAAGTTG |
| CAGGACCACTTCTGCGCTCGGCCCTTCCGGCTGGCTGGTTTATTGCTGATAAATCTGGAGCCGGTGAGC |
| GTGGGTCTCGCGGTATCATTGCAGCACTGGGGCCAGATGGTAAGCCCTCCCGTATCGTAGTTATCTACA |
| CGACGGGGAGTCAGGCAACTATGGATGAACGAAATAGACAGATCGCTGAGATAGGTGCCTCACTGATTA |
| AGCATTGGTAACTGTCAGACCAAGTTTACTCATATATACTTTAGATTGATTTAAAACTTCATTTTTAAT |
| TTAAAAGGATCTAGGTGAAGATCCTTTTTGATAATCTCATGACCAAAATCCCTTAACGTGAGTTTTCGT |
| TCCACTGAGCGTCAGACCCCGTAGAAAAGATCAAAGGATCTTCTTGAGATCCTTTTTTTCTGCGCGTAA |
| TCTGCTGCTTGCAAACAAAAAAACCACCGCTACCAGCGGTGGTTTGTTTGCCGGATCAAGAGCTACCAA |
| CTCTTTTTCCGAAGGTAACTGGCTTCAGCAGAGCGCAGATACCAAATACTGTTCTTCTAGTGTAGCCGT |
| AGTTAGGCCACCACTTCAAGAACTCTGTAGCACCGCCTACATACCTCGCTCTGCTAATCCTGTTACCAG |
| TGGCTGCTGCCAGTGGCGATAAGTCGTGTCTTACCGGGTTGGACTCAAGACGATAGTTACCGGATAAGG |
| CGCAGCGGTCGGGCTGAACGGGGGGTTCGTGCACACAGCCCAGCTTGGAGCGAACGACCTACACCGAAC |
| TGAGATACCTACAGCGTGAGCTATGAGAAAGCGCCACGCTTCCCGAAGGGAGAAAGGCGGACAGGTATC |
| CGGTAAGCGGCAGGGTCGGAACAGGAGAGCGCACGAGGGAGCTTCCAGGGGGAAACGCCTGGTATCTTT |
| ATAGTCCTGTCGGGTTTCGCCACCTCTGACTTGAGCGTCGATTTTTGTGATGCTCGTCAGGGGGGCGGA |
| GCCTATGGAAAAACGCCAGCAACGCGGCCTTTTTACGGTTCCTGGCCTTTTGCTGGCCTTTTGCTCACA |
| TGTTCTTTCCTGCGTTATCCCCTGATTCTGTGGATAACCGTATTACCGCCTTTGAGTGAGCTGATACCG |
| CTCGCCGCAGCCGAACGACCGAGCGCAGCGAGTCAGTGAGCGAGGAAGCGGAAGAGCGCCCAATACGCA |
| AACCGCCTCTCCCCGCGCGTTGGCCGATTCATTAATGCAGCTGTGGAATGTGTGTCAGTTAGGGTGTGG |
| AAAGTCCCCAGGCTCCCCAGCAGGCAGAAGTATGCAAAGCATGCATCTCAATTAGTCAGCAACCAGGTG |
| TGGAAAGTCCCCAGGCTCCCCAGCAGGCAGAAGTATGCAAAGCATGCATCTCAATTAGTCAGCAACCAT |
| AGTCCCGCCCCTAACTCCGCCCATCCCGCCCCTAACTCCGCCCAGTTCCGCCCATTCTCCGCCCCATGG |
| CTGACTAATTTTTTTTATTTATGCAGAGGCCGAGGCCGCCTCGGCCTCTGAGCTATTCCAGAAGTAGTG |
| AGGAGGCTTTTTTGGAGGCCTAGGCTTTTGCAAAAAGCTTGGACACAAGACAGGCTTGCGAGATATGTT |
| TGAGAATACCACTTTATCCCGCGTCAGGGAGAGGCAGTGCGTAAAAAGACGCGGACTCATGTGAAATAC |
| TGGTTTTTAGTGCGCCAGATCTCTATAATCTCGCGCAACCTATTTTCCCCTCGAACACTTTTTAAGCCG |
| TAGATAAACAGGCTGGGACACTTCACATGAGCGAAAAATACATCGTCACCTGGGACATGTTGCAGATCC |
| ATGCACGTAAACTCGCAAGCCGACTGATGCCTTCTGAACAATGGAAAGGCATTATTGCCGTAAGCCGTG |
| GCGGTCTGTACCGGGTGCGTTACTGGCGCGTGAACTGGGTATTCGTCATGTCGATACCGTTTGTATTTC |
| CAGCTACGATCACGACAACCAGCGCGAGCTTAAAGTGCTGAAACGCGCAGAAGGCGATGGCGAAGGCTT |
| CATCGTTATTGATGACCTGGTGGATACCGGTGGTACTGCGGTTGCGATTCGTGAAATGTATCCAAAAGC |
| GCACTTTGTCACCATCTTCGCAAAACCGGCTGGTCGTCCGGTGATCGATCTGTTGTGATATCCC |
| GCAAGATACCTGGATTGAACAGCCGTGGGATATGGGCGTCGTATTCGTCCCGCCAATCTCCGGTCGCTA |
| ATCTTTTCAACGCCTGGCACTGCCGGGCGTTGTTCTTTTTAACTTCAGGCGGGTTACAATAGTTTCCAG |
| TAAGTATTCTGGAGGCTGCATCCATGACACAGGCAAACCTGAGCGAAACCCTGTTCAAACCCGCTTTA |
| AACATCCTGAAACCTCGACGCTAGTCCGCCGCTTTAATCACGGCGCACAACCGCCTGTGCAGTCGGCCC |
| TTGATGGTAAAACCATCCCTCACTGGTATCGCATGATTAACCGTCTGATGTGGATCTGGCGCGGCATTG |
| ACCCACGCGAAATCCTCGACGTCCAGGCACGTATTGTGATGAGCGATGCCGAACGTACCGACGATGATT |
| TATACGATACGGTGATTGGCTACCGTGGCGGCAACTGGATTTATGAGTGGGCCCGGATCTTTGTGAAG |
| GAACCTTACTTCTGTGGTGTGACATAATTGGACAAACTACCTACAGAGATTTAAAGCTCTAAGGTAAAT |
| ATAAAATTTTTAAGTGTATAATGTGTTAAACTACTGATTCTAATTGTTTGTGTATTTTAGATTCCAACC |
| TATGGAACTGATGAATGGGAGCAGTGGTGGAATGCCTTTAATGAGGAAAACCTGTTTTGCTCAGAAGAA |
| ATGCCATCTAGTGATGATGAGGCTACTGCTGACTCTCAACATTCTACTCCTCCAAAAAAGAAGAGAAAG |
| GTAGAAGACCCCAAGGACTTTCCTTCAGAATTGCTAAGTTTTTTGAGTCATGCTGTGTTTAGTAATAGA |
| ACTCTTGCTTGCTTTGCTATTTACACCACAAAGGAAAAAGCTGCACTGCTATACAAGAAAATTATGGAA |
| AAATATTCTGTAACCTTTATAAGTAGGCATAACAGTTATAATCATAACATACTGTTTTTTCTTACTCCA |
| CACAGGCATAGAGTGTCTGCTATTAATAACTATGCTCAAAAATTGTGTACCTTTAGCTTTTTAATTTGT |
| AAAGGGGTTAATAAGGAATATTTGATGTATAGTGCCTTGACTAGAGATCATAATCAGCCATACCACATT |
| TGTAGAGGTTTTACTTGCTTTAAAAAACCTCCCACACCTCCCCCTGAACCTGAAACATAAAATGAATGC |
| AATTGTTGTTGTTAACTTGTTTATTGCAGCTTATAATGGTTACAAATAAAGCAATAGCATCACAAATTT |
| CACAAATAAAGCATTTTTTTCACTGCATTCTAGTTGTGGTTTGTCCAAACTCATCAATGTATCTTATCA |
| TGTCTGGATCAACTGGATAACTCAAGCTAACCAAAATCATCCCAAACTTCCCACCCCATACCCTATTAC |
| CACTGCC |

SEQ ID NO: 2 cPPT seq
ttttaaaaga aaggggggga ttggggggta cagtgcaggg gaaagaatag tagacataat 60
agcaacagac atacaaacta aagaattaca aaaacaaatt acaaaaattc aaaattttt 118

SEQ ID NO: 3
Woodchuck Hepatitus Virus wpre
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240

| Sequences |
|---|
| ggttggggca ttgccaccac ctgtcagctc ctttccggga ctttcgcttt cccctcctt 300
attgccacgg cggaactcat cgccgcctgc cttgcccgct gctggacagg ggctcggctg 360
ttgggcactg acaattccgt ggtgttgtcg gggaagctga cgtccttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tg 592 |

SEQ ID NO: 4
pORF-hIL-12 sequence (5048 bp).
hIL-12 open reading frame in bold.
Elastin linker is <u>underlined</u>.
GGATCTGCGATCGCTCCGGTGCCCGTCAGTGGGCAGAGCGCACATCGCCCACAGTCCCCGAGAAGTTGG
GGGGAGGGGTCGGCAATTGAACCGGTGCCTAGAGAAGGTGGCGCGGGGTAAACTGGGAAAGTGATGTCG
TGTACTGGCTCCGCCTTTTTCCCGAGGGTGGGGGAGAACCGTATATAAGTGCAGTAGTCGCCGTGAACG
TTCTTTTTCGCAACGGGTTTGCCGCCAGAACACAGCTGAAGCTTCGAGGGGCTCGCATCTCTCCTTCAC
GCGCCCGCCGCCCTACCTGAGGCCGCCATCCACGCCGGTTGAGTCGCGTTCTGCCGCCTCCCGCCTGTG
GTGCCTCCTGAACTGCGTCCGCCGTCTAGGTAAGTTTAAAGCTCAGGTCGAGACCGGGCCTTTGTCCGG
CGCTCCCTTGGAGCCTACCTAGACTCAGCCGGCTCTCCACGCTTTGCCTGACCCTGCTTGCTCAACTCT
ACGTCTTTGTTTTCGTTTTCTGTTCTGCGCCGTTACAGATCCAAGCTGTGACCGGCGCCTACgtaagtga
tatctactagatttatcaaaaagagtgttgacttgtgagcgctcacaattgatacttagattcatcgag
agggacacgtcgactactaaccttcttctctttcctacagCTGAGATCACCGGCGAAGGAGGGCCACC**A
TGGGTCACCAGCAGTTGGTCATCTCTTGGTTTTCCCTGGTTTTTCTGGCATCTCCCCTCGTGGCCATAT
GGGAACTGAAGAAAGATGTTTATGTCGTAGAATTGGATTGGTATCCGGATGCCCCTGGAGAAATGGTGG
TCCTCACCTGTGACACCCCTGAAGAAGATGGTATCACCTGGACCTTGGACCAGAGCAGTGAAGGTCTTAG
GCTCTGGCAAAACCCTGACCATCCAAGTCAAAGAGTTTGGAGATGCTGGCCAGTACACCTGTCACAAAG
GAGGCGAGGTTCTAAGCCATTCGCTCCTGCTGCTTCACAAAAGGAAGATGGAATTTGGTCCACTGATA
TTTTAAAGGACCAGAAAGAACCCAAAAATAAGACCTTTCTAAGATGCGAGGCCAAGAATTATTCTGGAC
GTTTCACCTGCTGGTGGCTGACGACAATCAGTACTGATTTGACATTCAGTGTCAAAAGCAGCAGAGGCT
CTTCTGACCCCCAAGGGGTGACGTGCGGAGCTGCTACACTCTCTGCAGAGAGAGTCAGAGGGGACAACA
AGGAGTATGAGTACTCAGTGGAGTGCCAGGAGGACAGTGCCTGCCCAGCTGCTGAGGAGAGTCTGCCCA
TTGAGGTCATGGTGGATGCCGTTCACAAGCTCAAGTATGAAAACTACACCAGCAGCTTCTTCATCAGGG
ACATCATCAAACCTGACCCACCCAAGAACTTGCAGCTGAAGCCCATTAAAGAATTCTCGGCAGGTGGAGG
TCAGCTGGGAGTACCCTGACACCTGGAGTACTCCACATTCCTACTTCTCCCTGACATTCTGCGTTCAGG
TCCAGGGCAAGAGCAAGAGAGAAAAGAAAGATAGAGTCTTCACGGACAAGACCTCAGCCACGGTCATCT
GCCGCAAAAATGCCAGCATTAGCGTGCGGGCCCAGGACCGCTACTATAGCTCATCTTGGAGCGAATGGG
CATCTGTGCCCTGCAGTGTTCCTGGAGTAGGGGTACCTGGGGTGGGCGCCAGAAACCTCCCCGTGGCCA
CTCCAGACCCAGGAATGTTCCCATGCCTTCACCACTCCCAAAACCTGCTGAGGGCCGTCAGCAACATGC
TCCAGAAGGCCAGACAAACTCTAGAATTTTACCCTTGCACTTCTGAAGAGATTGATCATGAAGATATCA
CAAAAGATAAAACCAGCACAGTGGAGGCCTGTTTACCATTGGAATTAACCAAGAATGAGAGTTGCCTAA
ATTCCAGAGAGACCTCTTTCATAACTAATGGGAGTTGCCTGGCCTCCAGAAAGACCTCTTTTATGATGG
CCCTGTGCCTTAGTAGTATTTATGAAGACTCGAAGATGTACCAGGTGGAGTTCAAGACCATGAATGCAA
AGCTTCTGATGGATCCTAAGAGGCAGATCTTTCTAGATCAAAACATGCTGGCAGTTATTGATGAGCTGA
TGCAGGCCCTGAATTTCAACAGTGAGACTGTGCCACAAAAATCCTCCCTTGAAGAACCGGATTTTTATA
AAACTAAAATCAAGCTCTGCATACTTCTTCATGCTTTCAGAATTCGGGCAGTGACTATTGATAGAGTGA
TGAGCTATCTGAATGCTTCCTAAAAAGCGAGGTCCCTCCAAACCTGTTCATTTTTATAAAACTTTGAA**
ATGAGGAAACTTTGATAGGATGTGGATTAAGAACTAGGGAGGGGAAAGAAGGATGGGACTATTACATC
CACATGATACCTCTGATCAAGTATTTTTGACATTTACTGTGGATAAATTGTTTTTAAGTTTTCATGAAT
GAATTGCTAAGAAGGGGGGAATTCTTTTGCTTTTTACCCTCGACTAGCTCGACATGATAAGACATTG
ATGAGTTTGGACAAACCACAACTAGAATGCAGTGAAAAAAATGCTTTATTTGTGAAATTTGTGATGCTA
TTGCTTTATTTGTGAAATTTGTGATGCTATTGCTTTATTTGTAACCATTATAAGCTGCAATAAACAAGT
TAACAACAACAATTGCATTCATTTTATGTTTCAGGTTCAGGGGGAGGTGTGGGAGGTTTTTTAAAGCAA
GTAAAACCTCTACAAATGTGGTAGATCATTTAAATGTTAATTAAGAACATGTGAGCAAAAGGCCAGCAA
AAGGCCAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGAAGTTTTAA
TCAATCTAAAGTATATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGATAACTACGATACGG
GAGGGCTTACCATCTGGCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCTCCGGTTCCCAA
CGATCAAGGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAATAGTGT
ATGCGGCGACCGAGTTGCTCTTGCCCGGCGTCAATACGGGATAATACCGCGCCACATAGCAGAACTTTA
AAAGTGCTCATCATTGGAAAACGTTCTTCGGGGCGAAAACTCTCAAGGATCTTACCGCTGTTGAGATCC
AGTTCGATGTAACCCACTCGTGCACCCAACTGATCTTCAGCATCTTTTACTTTCACCAGCGTTTCTGGG
TGAGCAAAAACAGGAAGGCAAAATGCCGCAAAAAAGGGAATAAGGGCGACACGGAAATGTTGAATACTC
ATACTCTTCCTTTTTCAATATTATTGAAGCATTTATCAGGGTTATTGTCTCATGAGCGGATACATATTT

| Sequences |
|---|
| GAATGTATTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCGTCTCGCG
CGTTTCGGTGATGACGGTGAAAACCTCTGACACATGCAGCTCCCGGAGACGGTCACAGCTTGTCTGTAA
GCGGATGCCGGGAGCAGACAAGCCCGTCAGGGCGCGTCAGCGGGTGTTGGCGGGTGTCGGGGCTGGCTT
AACTATGCGGCATCAGAGCAGATTGTACTGAGAGTGCACCATATGGATCTCGAGCGGCCGCAATAAAAT
ATCTTTATTTTCATTACATCTGTGTGTTGGTTTTTTGTGTGAATCGTAACTAACATACGCTCTCCATCA
AAACAAAACGAAACAAAACAAACTAGCAAAATAGGCTGTCCCCAGTGCAAGTGCAGGTGCCAGAACATT
TCTCTATCGAA SEQ ID NO: 5
pORF-mIL-12 (p35p40) sequence (4846 bp).
mIL-12 open reading frame in bold.
Elastin linker sequence is <u>undelined</u>.
GGATCTGCGATCGCTCCGGTGCCCGTCAGTGGGCAGAGCGCACATCGCCCACAGTCCCCGAGAAGTTGG
GGGGAGGGGTCGGCAATTGAACCGGTGCCTAGAGAAGGTGGCGCGGGGTAAACTGGGAAAGTGATGTCG
TGTACTGGCTCCGCCTTTTCCCGAGGGTGGGGGAGAACCGTATATAAGTGCAGTAGTCGCCGTGAACG
TTCTTTTTCGCAACGGGTTTGCCGCCAGAACACAGCTGAAGCTTCGAGGGGCTCGCATCTCTCCTTCAC
GCGCCCGCCGCCCTACCTGAGGCCGCCATCCACGCCGGTTGAGTCGCGTTCTGCCGCCTCCCGCCTGTG
GTGCCTCCTGAACTGCGTCCGCCGTCTAGGTAAGTTTAAAGCTCAGGTCGAGACCGGGCCTTTGTCCGG
CGCTCCCTTGGAGCCTACCTAGACTCAGCCGGCTCTCCACGCTTTGCCTGACCTGCTTGCTCAACTCT
ACGTCTTTGTTTCGTTTTCTGTTCTGCGCCGTTACAGATCCAAGCTGTGACCGGCGCCTACgtaagtga
tatctactagatttatcaaaaagagtgttgacttgtgagcgctcacaattgatacttagattcatcgag
agggacacgtcgactactaaccttcttctctCTGAGATCACCGGCGAAGGAGGGCCACC**ATGGGTCAAT
CACGCTACCTCCTCTTTTTGGCCACCCTTGCCCTCCTAAACCACCTCAGTTTGGCCAGGGTCATTCCAG
TCTCTGGACCTGCCAGGTGTCTTAGCCAGTCCCGAAACCTGCTGAAGACCACAGATGACATGGTGAAGA
CGGCCAGAGAAAAGCTGAAACATTATTCCTGCACTGCTGAAGACATCGATCATGAAGACATCACACGGG
ACCAAACCAGCACATTGAAGACCTGTTTACCACTGGAACTACACAAGAACGAGAGTTGCCTGGCTACTA
GAGAGACTTCTTCCACAACAAGAGGGAGCTGCCTGCCCCACAGAAGACGTCTTTGATGATGACCCTGT
GCCTTGGTAGCATCTATGAGGACTTGAAGATGTACCAGACAGAGTTCCAGGCCATCAACGCAGCACTTC
AGAATCACAACCATCAGCAGATCATTCTAGACAAGGGCATGCTGGTGGCCATCGATGAGCTGATGCAGT
CTCTGAATCATAATGGCGAGACTCTGCGCCAGAAACCTCCTGTGGGAGAAGCAGACCCTTACAGAGTGA
AAATGAAGCTCTGCATCCTGCTTCACGCCTTCAGCACCCGCGTCGTGACCATCAACAGGGTGATGGGCT
ATCTGAGCTCCGCC<u>GTTCCTGGAGTAGGGGT</u>ACCTGGAGTGGGCGGATCTATGTGGGAGCTGGAGAAAG
ACGTTTATGTTGTAGAGGTGGACTGGACTCCCGATGCCCTGGAGAAACAGTGAACCTCACCTGTGACA
CGCCTGAAGAAGATGACATCACCTGGACCTCAGACCAGAGACATGGAGTCATAGGCTCTGGAAAGACCC
TGACCATCACTGTCAAAGAGTTTCTAGATGCTGGCCAGTACACCTGCCACAAAGGAGGCGAGACTCTGA
GCCACTCACATCTGCTGCTCCACAAGAAGGAAAATGGAATTTGGTCCACTGAAATTTTAAAAAATTTCA
AAAACAAGACTTTCCTGAAGTGTGAAGCACCCAAATTACTCCGGACGGTTCACGTGCTCATGGCTGGTGC
AAAGAAACATGGACTTGAAGTTCAACATCAAGAGCAGTAGCAGTCCCCCGACTCTCGGGCAGTGACAT
GTGGAATGGCGTCTCTGTCTGCAGAGAAGGTCACACTGGACCAAAGGGACTATGAGAAGTATTCAGTGT
CCTGCCAGGAGGATGTCACCTGCCCAACTGCCGAGGAGACCCTGCCCATTGAACTGGCGTTGGAAGCAC
GGCAGCAGAATAAATATGAGAACTACAGCACCAGCTTCTTCATCAGGGACATCATCAAACCAGACCCGC
CCAAGAACTTGCAGATGAAGCCTTTGAAGAACTCACAGGTGGAGGTCAGCTGGGAGTACCCTGACTCCT
GGAGCACTCCCCATTCCTACTTCTCCCTCAAGTTCTTTGTTCGAATCCAGCGCAAGAAAGAAAAGATGA
AGGAGACAGAGGAGGGGTGTAACCAGAAAGGTGCGTTCCTCGTAGAGAAGACATCTACCGAAGTCCAAT
GCAAAGGCGGGAATGTCTGCGTGCAAGCTCAGGATCGCTATTACAATTCCTCATGCAGCAAGTGGGCAT
GTGTTCCTGCAGGGTCCGATCCTAGG**ATGCAACGGATGCTAGCTCGACATGATAAGATACATTGATGA
GTTTGGACAAACCACAACTAGAATGCAGTGAAAAAAATGCTTTATTTGTGAAATTTGTGATGCTATTGC
TTTATTTGTGAAATTTGTGATGCTATTGCTTTATTTGTAACCATTATAAGCTGCAATAAACAAGTTAAC
AACAACAATTGCATTCATTTTATGTTTCAGGTTCAGGGGGAGGTGTGGGAGGTTTTTTAAAGCAAGTAA
AACCTCTACAAATGTGGTAGATCATTTAAATGTTAATTAAGAACATGTGAGCAAAAGGCCAGCAAAAGG
CCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCTCCCTT
CGGGAAGCGTGGCGCTTTCTCAATGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGAACAGTAT
TTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAGGCACCTATCTCAG
CGATCTGTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAACTTTAAAAG
TGCTCATCATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATATTTGAAT
GTATTTAGAAAAATAAACAAATAGGGGTTCCGCGCACATTTCCCCGAAAAGTGCCACCTGACGTCTAAG |

| Sequences |
|---|
| AAACCATTATTATCATGACATTAACCTATAAAAATAGGCGTATCACGAGGCCCTTTCGTCTCGCGCGTT<br>TCGGTGATGACGGTGAAAACCTCTGACACATGCAGCTCCCGGAGACGGTCACAGCTTGTCTGTAAGCGG<br>ATGCCGGGAGCAGACAAGCCCGTCAGGGCGCGTCAGCGGGTGTTGGCGGGTGTCGGGGCTGGCTTAACT<br>ATGCGGCATCAGAGCAGATTGTACTGAGAGTGCACCCATATGGATCTCGAGCGGCCGCAATAAAATATCT<br>TTATTTTCATTACATCTGTGTGTTGGTTTTTTGTGTGAATCGTAACTAACATACGCTCTCCATCAAAAC<br>AAAACGAAACAAAACAAACTAGCAAAATAGGCTGTCCCCAGTGCAAGTGCAGGTGCCAGAACATTTCTC<br>TATCGAA<br>tmpk sequences |

```
<211> 639
<212> DNA
<213> Homo sapiens
atggcggccc ggcgcggggc tctcatagtg ctggagggcg tggaccgcgc cgggaagagc  60
acgcagagcc gcaagctggt ggaagcgctg tgcgccgcgg gccaccgcgc cgaactgctc 120
cggttcccgg aaagatcaac tgaaatcggc aaacttctga gttcctactt gcaaaagaaa 180
agtgacgtgg aggatcactc ggtgcacctg cttttttctg caaatcgctg ggaacaagtg 240
ccgttaatta aggaaaagtt gagccagggc gtgaccctcg tcgtggacag atacgcattt 300
tctggtgtgg ccttcaccgg tgccaaggag aattttttcc tagattggtg taaacagcca 360
gacgtgggcc ttcccaaacc cgacctggtc ctgttcctcc agttacagct ggcggatgct 420
gccaagcggg gagcgtttgg ccatgagcgc tatgagaacg gggcttttcca ggagcgggcg 480
ctccggtgtt tccaccagct catgaaagac acgactttga actggaagat ggtggatgct 540
tccaaaagca tcgaagctgt ccatgaggac atccgcgtgc tctctgagga cgccatccgc 600
actgccacag agaagccgct gggggagcta tggaagtga            639

<212> PRT
<213> Homo sapiens
Met Ala Ala Arg Arg Gly Ala Leu Ile Val Leu Glu Gly Val Asp Arg
1               5                   10                  15
Ala Gly Lys Ser Thr Gln Ser Arg Lys Leu Val Glu Ala Leu Cys Ala
            20                  25                  30
Ala Gly His Arg Ala Glu Leu Leu Arg Phe Pro Glu Arg Ser Thr Glu
        35                  40                  45
Ile Gly Lys Leu Leu Ser Ser Tyr Leu Gln Lys Lys Ser Asp Val Glu
    50                  55                  60
Asp His Ser Val His Leu Leu Phe Ser Ala Asn Arg Trp Glu Gln Val
65                  70                  75                  80
Pro Leu Ile Lys Glu Lys Leu Ser Gln Gly Val Thr Leu Val Val Asp
                85                  90                  95
Arg Tyr Ala Phe Ser Gly Val Ala Phe Thr Gly Ala Lys Glu Asn Phe
            100                 105                 110
Ser Leu Asp Trp Cys Lys Gln Pro Asp Val Gly Leu Pro Lys Pro Asp
        115                 120                 125
Leu Val Leu Phe Leu Gln Leu Gln Leu Ala Asp Ala Ala Lys Arg Gly
    130                 135                 140
Ala Phe Gly His Glu Arg Tyr Glu Asn Gly Ala Phe Gln Glu Arg Ala
145                 150                 155                 160
Leu Arg Cys Phe His Gln Leu Met Lys Asp Thr Thr Leu Asn Trp Lys
                165                 170                 175
Met Val Asp Ala Ser Lys Ser Ile Glu Ala Val His Glu Asp Ile Arg
            180                 185                 190
Val Leu Ser Glu Asp Ala Ile Arg Thr Ala Thr Glu Lys Pro Leu Gly
        195                 200                 205
Glu Leu Trp Lys
    210

<211> 639
<212> DNA
<213> Homo sapiens
atggcggccc ggcgcggggc tctcatagtg ctggagggcg tggaccgcgc cgggaagagc  60
acgcagagcc gcaagctggt ggaagcgctg tgcgccgcgg gccaccgcgc cgaactgctc 120
cggttcccgg aaagatcaac tgaaatcggc aaacttctga gttcctactt gcaaaagaaa 180
agtgacgtgg aggatcactc ggtgcacctg cttttttctg caaatcgctg ggaacaagtg 240
ccgttaatta aggaaaagtt gagccagggc gtgaccctcg tcgtggacag atacgcattt 300
tctggtgtgg ccttcaccgg tgccaaggag aattttttcc tagattggtg taaacagcca 360
gacgtgggcc ttcccaaacc cgacctggtc ctgttcctcc agttacagct ggcggatgct 420
gccaagcggg gagcgtttgg ccatgagcgc tatgagaacg gggcttttcca ggagcgggcg 480
ctccggtgtt tccaccagct catgaaagac acgactttga actggaagat ggtggatgct 540
tccaaaagca tcgaagctgt ccatgaggac atccgcgtgc tctctgagga cgccatccgc 600
actgccacag agaagccgct gggggagcta tggaagtga            639

<211> 212
<212> PRT
<213> Homo sapiens
Met Ala Ala Arg Arg Gly Ala Leu Ile Val Leu Glu Gly Val Asp Arg
1               5                   10                  15
Ala Gly Lys Ser Thr Gln Ser Arg Lys Leu Val Glu Ala Leu Cys Ala
            20                  25                  30
```

| Sequences |
|---|
| Ala Gly His Arg Ala Glu Leu Leu Arg Phe Pro Glu Arg Ser Thr Glu
           35                     40                      45
Ile Gly Lys Leu Leu Ser Ser Tyr Leu Gln Lys Lys Ser Asp Val Glu
  50                      55                      60
Asp His Ser Val His Leu Leu Phe Ser Ala Asn Arg Trp Glu Gln Val
65                      70                    75                  80
Pro Leu Ile Lys Glu Lys Leu Ser Gln Gly Val Thr Leu Val Val Asp
                  85                    90                    95
Arg Tyr Ala Phe Ser Gly Val Ala Phe Thr Gly Ala Lys Glu Asn Phe
                100                 105              110
Ser Leu Asp Trp Cys Lys Gln Pro Asp Val Gly Leu Pro Lys Pro Asp
        115                    120                125
Leu Val Leu Phe Leu Gln Leu Gln Leu Ala Asp Ala Ala Lys Arg Gly
    130                    135                140
Ala Phe Gly His Glu Arg Tyr Glu Asn Gly Ala Phe Gln Glu Arg Ala
145                      150                    155                160
Leu Arg Cys Phe His Gln Leu Met Lys Asp Thr Thr Leu Asn Trp Lys
                165                 170              175
Met Val Asp Ala Ser Lys Ser Ile Glu Ala Val His Glu Asp Ile Arg
        180                    185                190
Val Leu Ser Glu Asp Ala Ile Arg Thr Ala Thr Glu Lys Pro Leu Gly
    195                    200                205
Glu Leu Trp Lys
    210

<211> 636
<212> DNA
<213> *Homo sapiens*
atggcggccc ggcgcggggc tctcatagtg ctggagggcg tggaccgcgc cgggaagagc  60
acgcagagcc gcaagctggt ggaagcgctg tcgcgcgggc caccgcccga actgctccga 120
ttcccggaaa gatcaactga aatcggcaaa cttctgagtt cctacttgca aaagaaaagt 180
gacgtggagg atcactcggt gcacctgctt ttttctgcaa atcgctggga acaagtgccg 240
ttaattaagg aaaagttgag ccagggcgtg accctcgtcg tggacagata cgcattttct 300
ggtgtggcct tcaccggtgc caaggagaat ttttccctag actggtgtaa acagccagac 360
gtgggccttc ccaaacccga cctggtcctg ttcctccagt tacagctggc ggatgctgcc 420
aagcggggag cgtttggcca tgagcgctat gagaacgggg cttttccagga gcgggcgctc 480
cggtgtttcc accagctcat gaaagacacg actttgaact ggaagatggt ggatgcttcc 540
aaaagactcg aagctgtcca tgaggaactc cgcgtgctct ctgaggacgc catccgcact 600
gccacagaga agccgctggg ggagctatgg aagtga                            636

<211> 211
<212> PRT
<213> *Homo sapiens*
Met Ala Ala Arg Arg Gly Ala Leu Ile Val Leu Glu Gly Val Asp Arg
1                   5                    10                    15
Ala Gly Lys Ser Thr Gln Ser Arg Lys Leu Val Glu Ala Leu Ser Arg
          20                    25                    30
Gly Pro Pro Pro Glu Leu Leu Arg Phe Pro Glu Arg Ser Thr Glu Ile
                35                    40                    45
Gly Lys Leu Leu Ser Ser Tyr Leu Gln Lys Lys Ser Asp Val Glu Asp
  50                      55                      60
His Ser Val His Leu Leu Phe Ser Ala Asn Arg Trp Glu Gln Val Pro
65                      70                    75                  80
Leu Ile Lys Glu Lys Leu Ser Gln Gly Val Thr Leu Val Val Asp Arg
                85                    90                    95
Tyr Ala Phe Ser Gly Val Ala Phe Thr Gly Ala Lys Glu Asn Phe Ser
                100                 105              110
Leu Asp Trp Cys Lys Gln Pro Asp Val Gly Leu Pro Lys Pro Asp Leu
        115                    120                125
Val Leu Phe Leu Gln Leu Gln Leu Ala Asp Ala Ala Lys Arg Gly Ala
    130                    135                140
Phe Gly His Glu Arg Tyr Glu Asn Gly Ala Phe Gln Glu Arg Ala Leu
145                    150                    155                160
Arg Cys Phe His Gln Leu Met Lys Asp Thr Thr Leu Asn Trp Lys Met
                165                 170              175
Val Asp Ala Ser Lys Arg Leu Glu Ala Val His Glu Glu Leu Arg Val
        180                    185                190
Leu Ser Glu Asp Ala Ile Arg Thr Ala Thr Glu Lys Pro Leu Gly Glu
    195                    200                205
Leu Trp Lys
    210

<211> 639
<212> DNA
<213> *Homo sapiens*
atggcggccc ggcgcggggc tctcatagtg ctggagggcg tggaccgcgc cgggaagagc  60
acgcagagcc gcaagctggt ggaagcgctg tcgccgcggg ccaccgcgc cgaactgctc 120

| Sequences |
|---|
| cggttcccgg aaagatcaac tgaaatcggc aaacttctga gttcctactt gcaaaagaaa 180
agtgacgtgg aggatcactc ggtgcacctg cttttttctg caaatcgctg ggaacaagtg 240
ccgttaatta aggaaaagtt gagccagggc gtgaccctcg tcgtggacag atacgcattt 300
tctggtgtgg ccttcaccgg tgccaaggag aattttttcc tagattggtg taaacagcca 360
gacgtgggcc ttcccaaacc cgacctggtc ctgttcctcc agttacagct ggcggatgct 420
gccaagcggg gagcgtttgg ccatgagcgc tatgagaacg gggctttcca ggagcgggcg 480
ctccggtgtt tccaccagct catgaaagac acgactttga actggaagat ggtggatgct 540
tccaaaagca tcgaagctgt ccatgaggac atccgcgtgc tctctgagga cgccatccgc 600
actgccacag agaagccgct gggggagcta tggaaggac 639 |

```
<211> 213
<212> PRT
<213> Homo sapiens
Met Ala Ala Arg Arg Gly Ala Leu Ile Val Leu Glu Gly Val Asp Arg
1               5                   10                  15
Ala Gly Lys Ser Thr Gln Ser Arg Lys Leu Val Glu Ala Leu Cys Ala
                20                  25                  30
Ala Gly His Arg Ala Glu Leu Leu Arg Phe Pro Glu Arg Ser Thr Glu
            35                  40                  45
Ile Gly Lys Leu Leu Ser Ser Tyr Leu Gln Lys Lys Ser Asp Val Glu
        50                  55                  60
Asp His Ser Val His Leu Leu Phe Ser Ala Asn Arg Trp Glu Gln Val
65                  70                  75                  80
Pro Leu Ile Lys Glu Lys Leu Ser Gln Gly Val Thr Leu Val Val Asp
                85                  90                  95
Arg Tyr Ala Phe Ser Gly Val Ala Phe Thr Gly Ala Lys Glu Asn Phe
                100                 105                 110
Ser Leu Asp Trp Cys Lys Gln Pro Asp Val Gly Leu Pro Lys Pro Asp
            115                 120                 125
Leu Val Leu Phe Leu Gln Leu Gln Leu Ala Asp Ala Ala Lys Arg Gly
        130                 135                 140
Ala Phe Gly His Glu Arg Tyr Glu Asn Gly Ala Phe Gln Glu Arg Ala
145                 150                 155                 160
Leu Arg Cys Phe His Gln Leu Met Lys Asp Thr Thr Leu Asn Trp Lys
                165                 170                 175
Met Val Asp Ala Ser Lys Ser Ile Glu Ala Val His Glu Asp Ile Arg
                180                 185                 190
Val Leu Ser Glu Asp Ala Ile Arg Thr Ala Thr Glu Lys Pro Leu Gly
            195                 200                 205
Glu Leu Trp Lys Asp
        210
```

```
<211> 639
<212> DNA
<213> Mus musculus
atggcgtcgc gtcggggagc gctcatcgtg ctggagggtg tggaccgtgc tggcaagacc 60
acgcagggcc tcaagctggt gaccgcgctg tgcgcctcgg gccacagagc ggagctgctg 120
cgtttccccg aaagatcaac ggaaatcggc aagcttctga attcctactt ggaaaagaaa 180
acggaactag aggatcactc cgtgcacctg ctcttctctg caaaccgctg ggaacaagta 240
ccattaatta aggcgaagtt gaaccagggt gtgaccctg ttttggacag atacgccttt 300
tctggggttg ccttcactgg tgccaaagag aattttttcc tggattggtg taaacaaccg 360
gacgtgggcc ttcccaaacc tgacctgatc ctgttccttc agttacaatt gctggacgct 420
gctgcacggg gagagtttgg ccttgagcga tatgagaccg ggacttttca aaagcaggtt 480
ctgttgtgtt tccagcagct catggaagag aaaaaacctca actggaaggt ggttgatgct 540
tccaaaagca ttgaggaagt ccataaagaa atccgtgcac actctgagga cgccatccga 600
aacgctgcac agaggccact gggggagcta tggaaataa 639
```

```
<211> 212
<212> PRT
<213> Mus musculus
Met Ala Ser Arg Arg Gly Ala Leu Ile Val Leu Glu Gly Val Asp Arg
1               5                   10                  15
Ala Gly Lys Thr Thr Gln Gly Leu Lys Leu Val Thr Ala Leu Cys Ala
                20                  25                  30
Ser Gly His Arg Ala Glu Leu Leu Arg Phe Pro Glu Arg Ser Thr Glu
            35                  40                  45
Ile Gly Lys Leu Leu Asn Ser Tyr Leu Glu Lys Lys Thr Glu Leu Glu
        50                  55                  60
Asp His Ser Val His Leu Leu Phe Ser Ala Asn Arg Trp Glu Gln Val
65                  70                  75                  80
Pro Leu Ile Lys Ala Lys Leu Asn Gln Gly Val Thr Leu Val Leu Asp
                85                  90                  95
Arg Tyr Ala Phe Ser Gly Val Ala Phe Thr Gly Ala Lys Glu Asn Phe
                100                 105                 110
Ser Leu Asp Trp Cys Lys Gln Pro Asp Val Gly Leu Pro Lys Pro Asp
            115                 120                 125
Leu Ile Leu Phe Leu Gln Leu Gln Leu Leu Asp Ala Ala Ala Arg Gly
```

| Sequences |
|---|
| 130 135 140
Glu Phe Gly Leu Glu Arg Tyr Glu Thr Gly Thr Phe Gln Lys Gln Val
145                 150                 155                 160
Leu Leu Cys Phe Gln Gln Leu Met Glu Glu Lys Asn Leu Asn Trp Lys
                165                 170                 175
Val Val Asp Ala Ser Lys Ser Ile Glu Glu Val His Lys Glu Ile Arg
            180                 185                 190
Ala His Ser Glu Asp Ala Ile Arg Asn Ala Ala Gln Arg Pro Leu Gly
        195                 200                 205
Glu Leu Trp Lys
    210

<211> 212
<212> PRT
<213> *Homo sapiens*
Met Ala Ala Arg Arg Gly Ala Leu Ile Val Leu Glu Gly Val Asp Arg
1               5                   10                  15
Ala Gly Lys Ser Thr Gln Ser Arg Lys Leu Val Glu Ala Leu Cys Ala
                20                  25                  30
Ala Gly His Arg Ala Glu Leu Leu Arg Phe Pro Glu Arg Ser Thr Glu
            35                  40                  45
Ile Gly Lys Leu Leu Ser Ser Tyr Leu Gln Lys Lys Ser Asp Val Glu
        50                  55                  60
Asp His Ser Val His Leu Leu Phe Ser Ala Asn Arg Trp Glu Gln Val
65                  70                  75                  80
Pro Leu Ile Lys Glu Lys Leu Ser Gln Gly Val Thr Leu Val Val Asp
                85                  90                  95
Arg Tyr Ala Phe Ser Gly Val Ala Tyr Thr Gly Ala Lys Glu Asn Phe
            100                 105                 110
Ser Leu Asp Trp Cys Lys Gln Pro Asp Val Gly Leu Pro Lys Pro Asp
        115                 120                 125
Leu Val Leu Phe Leu Gln Leu Gln Leu Ala Asp Ala Ala Lys Arg Gly
    130                 135                 140
Ala Phe Gly His Glu Arg Tyr Glu Asn Gly Ala Phe Gln Glu Arg Ala
145                 150                 155                 160
Leu Arg Cys Phe His Gln Leu Met Lys Asp Thr Thr Leu Asn Trp Lys
                165                 170                 175
Met Val Asp Ala Ser Lys Ser Ile Glu Ala Val His Glu Asp Ile Arg
            180                 185                 190
Val Leu Ser Glu Asp Ala Ile Arg Thr Ala Thr Glu Lys Pro Leu Gly
        195                 200                 205
Glu Leu Trp Lys
    210

<211> 214
<212> PRT
<213> *Homo sapiens*
Met Ala Ala Arg Arg Gly Ala Leu Ile Val Leu Glu Gly Val Asp Gly
1               5                   10                  15
Ala Gly Lys Ser Thr Gln Ser Arg Lys Leu Val Glu Ala Leu Cys Ala
                20                  25                  30
Ala Gly His Arg Ala Glu Leu Leu Arg Phe Pro Glu Arg Ser Thr Glu
            35                  40                  45
Ile Gly Lys Leu Leu Ser Ser Tyr Leu Gln Lys Lys Ser Asp Val Glu
        50                  55                  60
Asp His Ser Val His Leu Leu Phe Ser Ala Asn Arg Trp Glu Gln Val
65                  70                  75                  80
Pro Leu Ile Lys Glu Lys Leu Ser Gln Gly Val Thr Leu Val Val Asp
                85                  90                  95
Arg Tyr Ala Phe Ser Gly Val Ala Phe Thr Gly Ala Lys Glu Asn Phe
            100                 105                 110
Ser Leu Asp Trp Cys Lys Gln Pro Asp Val Gly Leu Pro Lys Pro Asp
        115                 120                 125
Leu Val Leu Phe Leu Gln Leu Thr Pro Glu Val Gly Leu Lys Arg Ala
    130                 135                 140
Arg Ala Arg Gly Gln Leu Asp Arg Tyr Glu Asn Gly Ala Phe Gln Glu
145                 150                 155                 160
Arg Ala Leu Arg Cys Phe His Gln Leu Met Lys Asp Thr Thr Leu Asn
                165                 170                 175
Trp Lys Met Val Asp Ala Ser Lys Ser Ile Glu Ala Val His Glu Asp
            180                 185                 190
Ile Arg Val Leu Ser Glu Asp Ala Ile Ala Thr Ala Thr Glu Lys Pro
        195                 200                 205
Leu Gly Glu Leu Trp Lys
    210

The invention claimed is:

1. A method of treating cancer in a human patient in need thereof, the method comprising administering to the patient a composition comprising a population of human cells transduced with a retroviral vector comprising a polynucleotide encoding human interleukin-12 (IL-12), wherein the population of cells secretes IL-12 at a concentration of at least about 1,500 pg/ml when the cells are cultured at a density of about $10^6$ cells/ml for 2 hours.

2. The method of claim 1, wherein the cells are cancer cells.

3. The method of claim 2, wherein the cancer cells are leukemia cells.

4. The method of claim 3, wherein the leukemia cells are acute myeloid leukemia (AML) cells, acute lymphoid leukemia (ALL) cells, chronic myeloid leukemia (CML) cells, or chronic lymphoid leukemia (CLL) cells.

5. The method of claim 1, wherein the cells are T-cells.

6. The method of claim 1, wherein the cells are stem cells.

7. The method of claim 6, wherein the stem cells are embryonic stem cells.

8. The method of claim 1, wherein the cells comprise at least about 0.5% of the total quantity of cells in the composition.

9. The method of claim 8, wherein the cells comprise at least about 2% of the total quantity of cells in the composition.

10. The method of claim 9, wherein the cells comprise at least about 10% of the total quantity of cells in the composition.

11. The method of claim 10, wherein the cells comprise at least about 50% of the total quantity of cells in the composition.

12. The method of claim 11, wherein the cells comprise at least about 95% of the total quantity of cells in the composition.

13. The method of claim 1, wherein the retroviral vector further comprises a polynucleotide encoding an immunomodulatory protein selected from the group consisting of CD40L, IL-7, or IL-15.

14. The method of claim 1, wherein the cancer is leukemia.

15. The method of claim 14, wherein the leukemia is AML, ALL, CML, or CLL.

16. The method of claim 1, wherein the cancer is a solid tumor.

17. The method of claim 16, wherein the cancer is lung cancer, ovarian cancer, prostate cancer, breast cancer, melanoma, colon cancer, bladder cancer, liver cancer, pancreatic cancer, thyroid cancer, head and neck cancer, or renal cancer.

18. The method of claim 1, wherein the cells are autologous with respect to the human patient.

19. The method of claim 1, wherein the cells are allogeneic with respect to the human patient.

20. The method of claim 1, wherein the composition is administered intravenously, intraperitoneally, intratumorally, intramuscularly, intradermally, or subcutaneously.

* * * * *

SEQUENCE LISTING

<160> NUMBER OF SEQ ID NOS: 21

<210> SEQ ID NO 1
<211> LENGTH: 12718
<212> TYPE: DNA
<213> ORGANISM: Artificial Sequence
<220> FEATURE:
<223> OTHER INFORMATION: Synthetic Construct (pHR'.cPPT.EF.CD19delta
      TmpkF105YR200A.WPRE.SIN)

<400> SEQUENCE: 1

| | | | | | |
|---|---|---|---|---|---|
| aattacctgt | ggtttcattt | actctaaacc | tgtgattcct | ctgaattatt | ttcattttaa | 60 |
| agaaattgta | tttgttaaat | atgtactaca | aacttagtag | ttggaagggc | taattcactc | 120 |
| ccaaagaaga | caagatatcc | ttgatctgtg | gatctaccac | acacaaggct | acttccctga | 180 |
| ttagcagaac | tacacaccag | ggccagggt | cagatatcca | ctgacctttg | gatggtgcta | 240 |
| caagctagta | ccagttgagc | cagataaggt | agaagaggcc | aataaaggag | agaacaccag | 300 |
| cttgttacac | cctgtgagcc | tgcatgggat | ggatgacccg | gagagagaag | tgttagagtg | 360 |
| gaggtttgac | agccgcctag | catttcatca | cgtggcccga | gagctgcatc | cggagtactt | 420 |
| caagaactgc | tgatatcgag | cttgctacaa | gggactttcc | gctggggact | ttccagggag | 480 |
| gcgtggcctg | ggcgggactg | gggagtggcg | agccctcaga | tcctgcatat | aagcagctgc | 540 |
| tttttgcctg | tactgggtct | ctctggttag | accagatctg | agcctgggag | ctctctggct | 600 |
| aactagggaa | cccactgctt | aagcctcaat | aaagcttgcc | ttgagtgctt | caagtagtgt | 660 |
| gtgcccgtct | gttgtgtgac | tctggtaact | agagatccct | cagacccttt | tagtcagtgt | 720 |
| ggaaaatctc | tagcagtggc | gcccgaacag | ggacttgaaa | gcgaaaggga | aaccagagga | 780 |
| gctctctcga | cgcaggactc | ggcttgctga | agcgcgcacg | gcaagaggcg | aggggcggcg | 840 |
| actggtgagt | acgccaaaaa | ttttgactag | cggaggctag | aaggagagag | atgggtgcga | 900 |
| gagcgtcagt | attaagcggg | ggagaattag | atcgcgatgg | gaaaaaattc | ggttaaggcc | 960 |
| aggggggaaag | aaaaaatata | aattaaaaca | tatagtatgg | gcaagcaggg | agctagaacg | 1020 |
| attcgcagtt | aatcctggcc | tgttagaaac | atcagaaggc | tgtagacaaa | tactgggaca | 1080 |
| gctacaacca | tcccttcaga | caggatcaga | agaacttaga | tcattatata | atacagtagc | 1140 |
| aaccctctat | tgtgtgcatc | aaaggataga | gataaaagac | accaaggaag | ctttagacaa | 1200 |
| gatagaggaa | gagcaaaaca | aaagtaagac | caccgcacag | caagcggccg | ctgatcttca | 1260 |
| gacctggagg | aggagatatg | agggacaatt | ggagaagtga | attatataaa | tataaagtag | 1320 |
| taaaaattga | accattagga | gtagcaccca | ccaaggcaaa | gagaagagtg | gtgcagagag | 1380 |
| aaaaaagagc | agtgggaata | ggagctttgt | tccttgggtt | cttgggagca | gcaggaagca | 1440 |
| ctatgggcgc | agcgtcaatg | acgctgacgg | tacaggccag | acaattattg | tctggtatag | 1500 |
| tgcagcagca | gaacaatttg | ctgagggcta | ttgaggcgca | acagcatctg | ttgcaactca | 1560 |
| cagtctgggg | catcaagcag | ctccaggcaa | gaatcctggc | tgtggaaaga | tacctaaagg | 1620 |
| atcaacagct | cctggggatt | tggggttgct | ctggaaaact | catttgcacc | actgctgtgc | 1680 |
| cttggaatgc | tagttggagt | aataaatctc | tggaacagat | ttggaatcac | acgacctgga | 1740 |
| tggagtggga | cagagaaatt | aacaattaca | caagcttaat | acactcctta | attgaagaat | 1800 |
| cgcaaaacca | gcaagaaaag | aatgaacaag | aattattgga | attagataaa | tgggcaagtt | 1860 |
| tgtggaattg | gtttaacata | acaaattggc | tgtggtatat | aaaattattc | ataatgatag | 1920 |
| taggaggctt | ggtaggttta | agaatagttt | ttgctgtact | ttctatagtg | aatagagtta | 1980 |

```
ggcagggata ttcaccatta tcgtttcaga cccacctccc aaccccgagg ggacccgaca   2040
ggcccgaagg aatagaagaa gaaggtggag agagagacag agacagatcc attcgattag   2100
tgaacggatc tcgacggtat cgattttaaa agaaaggggg ggattgggg gtacagtgca    2160 ggggaaagaa tagtagacat aatagcaaca gacatacaaa ctaaagaatt acaaaaacaa   2220
attacaaaaa ttcaaaattt tatcgataag ctttgcaaag atggataaag ttttaaacag   2280
agaggaatct ttgcagctaa tggaccttct aggtcttgaa aggagtggga attggctccg   2340
gtgcccgtca gtgggcagag cgcacatcgc ccacagtccc cgagaagttg gggggagggg   2400
tcggcaattg aaccggtgcc tagagaaggt ggcgcgggt aaactgggaa agtgatgtcg    2460
tgtactggct ccgcctttt cccgagggtg ggggagaacc gtatataagt gcagtagtcg    2520
ccgtgaacgt tcttttttcgc aacgggtttg ccgccagaac acaggtaagt gccgtgtgtg  2580
gttcccgcgg gcctggcctc tttacgggtt atggcccttg cgtgccttga attacttcca   2640
cctggctgca gtacgtgatt cttgatcccg agcttcgggt tggaagtggg tgggagagtt   2700
cgaggccttg cgcttaagga gcccttcgc ctcgtgcttg agttgaggcc tggcctgggc    2760
gctggggccg ccgcgtgcga atctggtggc accttcgcgc ctgtctcgct gctttcgata   2820
agtctctagc catttaaaat ttttgatgac ctgctgcgac ctttttttc tggcaagata    2880 gtcttgtaaa tgcgggccaa gatctgcaca ctggtatttc ggttttggg gccgcgggcg    2940 gcgacggggc ccgtgcgtcc cagcgcacat gttcggcgag gcggggcctg cgagcgcggc   3000
caccgagaat cggacggggg tagtctcaag ctggccggcc tgctctggtg cctggcctcg   3060
cgccgccgtg tatcgccccg ccctgggcgg caaggctggc ccgtcggca ccagttgcgt    3120 gagcggaaag atggccgctt cccggccctg ctgcaggag ctcaaaatgg aggacgcggc    3180
gctcgggaga gcgggcgggt gagtcaccca cacaaggaa aagggccttt ccgtcctcag    3240
ccgtcgcttc atgtgactcc acggagtacc gggcgccgtc caggcacctc gattagttct   3300
cgagcttttg gagtacgtcg tctttaggtt ggggggaggg gttttatgcg atggagtttc   3360
cccacactga gtgggtggag actgaagtta ggccagcttg cacttgatg taattctcct    3420 tggaatttgc cctttttgag tttggatctt ggttcattct caagcctcag acagtggttc   3480 aaagttttt tcttccattt caggtgtcgt gaggaattca tgccacctcc tcgcctcctc    3540
ttcttcctcc tcttcctcac ccccatggaa gtcaggcccg aggaacctct agtggtgaag   3600
gtggaagagg gagataacgc tgtgctgcag tgcctcaagg ggacctcaga tggccccact   3660
cagcagctga cctggtctcg ggagtccccg cttaaaccct tcttaaaact cagcctgggg   3720
ctgccaggcc tgggaatcca catgaggccc ctggcatcct ggcttttcat cttcaacgtc   3780
tctcaacaga tggggggctt ctacctgtgc cagccggggc ccccctctga aaggcctgg    3840 cagcctggct ggacagtcaa tgtggagggc agcggggagc tgttccggtg gaatgtttcg   3900
gacctaggtg gcctgggctg tggcctgaag aacaggtcct cagagggccc cagctcccct   3960
tccgggaagc tcatgagccc caagctgtat gtgtgggcca agaccgccc tgagatctgg   4020 gagggagagc ctccgtgtgt cccaccgagg gacagcctga accagagcct cagccaggac   4080
ctcaccatgg cccctggctc cacactctgg ctgtcctgtg ggtaccccc tgactctgtg   4140 tccaggggcc cctctcctg gacccatgtg caccccaagg ggcctaagtc attgctgagc    4200
ctagagctga aggacgatcg cccggccaga gatatgtggg taatggagac gggtctgttg   4260
ttgccccggg ccacagctca agacgctgga aagtattatt gtcaccgtgg caacctgacc   4320
atgtcattcc acctggagat cactgctcgg ccagtactat ggcactggct gctgaggact   4380
```

```
ggtggctgga aggtctcagc tgtgactttg gcttatctga tcttctgcct gtgttccctt    4440
gtgggcattc ttcatcttgc cggcggggct gcagggatgg cggcccggcg cggggctctc    4500
atagtgctgg agggcgtgga ccgcgccggg aagagcacgc agagccgcaa gctggtggaa    4560
gcgctgtgcg ccgcgggcca ccgcgccgaa ctgctccggt tcccggaaag atcaactgaa    4620
atcggcaaac ttctgagttc ctacttgcaa aagaaaagtg acgtggagga tcactcggtg    4680
cacctgcttt tttctgcaaa tcgctgggaa caagtgccgt taattaagga aaagttgagc    4740
cagggcgtga ccctcgtcgt ggacagatac gcattttctg gtgtggccta cacaggtgcc    4800
aaggagaatt tttccctaga ctggtgtaaa cagccagacg tgggccttcc caaacccgac    4860
ctggtcctgt tcctccagtt acagctggcg gatgctgcca agcggggagc gtttggccat    4920
gagcgctatg agaacggggc tttccaggag cgggcgctcc ggtgtttcca ccagctcatg    4980
aaagacacga ctttgaactg gaagatggtg gatgcttcca aaagcatcga agctgtccat    5040
gaggacatcc gcgtgctctc tgaggacgcc atcgccactg ccacagagaa gccgctgggg    5100
gagctatgga agtgaggatc caagcttcaa ttgtggtcac tcgacaatca acctctggat    5160
tacaaaattt gtgaaagatt gactggtatt cttaactatg ttgctccttt tacgctatgt    5220
ggatacgctg ctttaatgcc tttgtatcat gctattgctt cccgtatggc tttcattttc    5280
tcctccttgt ataatcctg gttgctgtct ctttatgagg agttgtggcc cgttgtcagg    5340
caacgtggcg tggtgtgcac tgtgtttgct gacgcaaccc ccactggttg gggcattgcc    5400
accacctgtc agctcctttc cgggactttc gctttccccc tcctattgc cacggcggaa    5460 ctcatcgccg cctgccttgc ccgctgctgg acaggggctc ggctgttggg cactgacaat    5520
tccgtggtgt tgtcggggaa gctgacgtcc tttccatggc tgctcgcctg tgttgccacc    5580
tggattctgc gcgggacgtc cttctgctac gtcccttcgg ccctcaatcc agcggacctt    5640
ccttcccgcg gcctgctgcc ggctctgcgg cctcttccgc gtcttcgcct tcgccctcag    5700
acgagtcgga tctccctttg gccgcctcc ccgcctgctc gagacctaga aaacatgga    5760 gcaatcacaa gtagcaatac agcagctacc aatgctgatt gtgcctggct agaagcacaa    5820
gaggaggagg aggtgggttt tccagtcaca cctcaggtac ctttaagacc aatgacttac    5880
aaggcagctg tagatcttag ccactttta aagaaaaagg ggggactgga agggctaatt    5940
cactcccaac gaagacaaga tctgcttttt gcttgtactg ggtctctctg gttagaccag    6000
atctgagcct gggagctctc tggctaacta gggaacccac tgcttaagcc tcaataaagc    6060
ttgccttgag tgcttcaagt agtgtgtgcc cgtctgttgt gtgactctgg taactagaga    6120
tccctcagac ccttttagtc agtgtggaaa atctctagca gtagtagttc atgtcatctt    6180
attattcagt atttataact tgcaaagaaa tgaatatcag agagtgagag gccttgacat    6240
tataatagat ttagcaggaa ttgaactagg agtggagcac acaggcaaag ctgcagaagt    6300
acttggaaga agccaccaga gatactcacg attctgcaca tacctggcta atcccagatc    6360
ctaaggatta cattaagttt actaacattt atataatgat ttatagttta agtataaac     6420 ttatctaatt tactattctg acagatatta attaatcctc aaatatcata agagatgatt    6480
actattatcc ccatttaaca caagaggaaa ctgagggga aagatgttga agtaattttc     6540
ccacaattac agcatccgtt agttacgact ctatgatctt ctgacacaaa ttccatttac    6600
tcctcaccct atgactcagt cgaatatatc aaagttatgg acattatgct aagtaacaaa    6660
ttaccctttt atatagtaaa tactgagtag attgagagaa gaaattgttt gcaaacctga    6720
```

```
atagcttcaa gaagaagaga agtgaggata agaataacag ttgtcattta acaagtttta    6780
acaagtaact tggttagaaa gggattcaaa tgcataaagc aagggataaa tttttctggc    6840
aacaagacta tacaatataa ccttaaatat gacttcaaat aattgttgga acttgataaa    6900
actaattaaa tattattgaa gattatcaat attataaatg taatttactt ttaaaaaggg    6960
aacatagaaa tgtgtatcat tagagtagaa aacaatcctt attatcacaa tttgtcaaaa    7020
caagtttgtt attaacacaa gtagaatact gcattcaatt aagttgactg cagattttgt    7080
gttttgttaa aattagaaag agataacaac aatttgaatt attgaaagta acatgtaaat    7140
agttctacat acgttctttt gacatcttgt tcaatcattg atcgaagttc tttatcttgg    7200
aagaatttgt tccaaagact ctgaaataag gaaaacaatc tattatatag tctcacacct    7260
ttgttttact tttagtgatt tcaatttaat aatgtaaatg gttaaaattt attcttctct    7320
gagatcattt cacattgcag atagaaaacc tgagactggg gtaattttta ttaaaatcta    7380
atttaatctc agaaacacat ctttattcta acatcaattt ttccagtttg atattatcat    7440
ataaagtcag ccttcctcat ctgcaggttc cacaacaaaa atccaaccaa ctgtggatca    7500
aaaatattgg gaaaaaatta aaatagcaa tacaacaata aaaaaataca aatcagaaaa     7560
acagcacagt ataacaactt tatttagcat ttacaatcta ttaggtatta taagtaatct    7620
agaattaatt ccgtgtattc tatagtgtca cctaaatcgt atgtgtatga tacataaggt    7680
tatgtattaa ttgtagccgc gttctaacga caatatgtac aagcctaatt gtgtagcatc    7740
tggcttactg aagcagaccc tatcatctct ctcgtaaact gccgtcagag tcggtttggt    7800
tggacgaacc ttctgagttt ctggtaacgc cgtcccgcac ccggaaatgg tcagcgaacc    7860
aatcagcagg gtcatcgcta gccagatcct ctacgccgga cgcatcgtgg ccggcatcac    7920
cggcgccaca ggtgcggttg ctggcgccta tatcgccgac atcaccgatg ggaagatcg     7980 ggctcgccac ttcgggctca tgagcgcttg tttcggcgtg ggtatggtgg caggccccgt    8040
ggccggggga ctgttgggcg ccatctcctt gcatgcacca ttccttgcgg cggcggtgct    8100
caacggcctc aacctactac tgggctgctt cctaatgcag gagtcgcata agggagagcg    8160
tcgaatggtg cactctcagt acaatctgct ctgatgccgc atagttaagc cagccccgac    8220
acccgccaac acccgctgac gcgccctgac gggcttgtct gctcccggca tccgcttaca    8280
gacaagctgt gaccgtctcc gggagctgca tgtgtcagag gttttcaccg tcatcaccga    8340
aacgcgcgag acgaaagggc ctcgtgatac gcctattttt ataggttaat gtcatgataa    8400
taatggtttc ttagacgtca ggtggcactt ttcggggaaa tgtgcgcgga acccctattt    8460
gtttattttt ctaaatacat tcaaatatgt atccgctcat gagacaataa ccctgataaa    8520
tgcttcaata atattgaaaa aggaagagta tgagtattca catttccgt gtcgccctta     8580 ttcccttttt tgcggcattt tgccttcctg tttttgctca cccagaaacg ctggtgaaag    8640
taaaagatgc tgaagatcag ttgggtgcac gagtgggtta catcgaactg gatctcaaca    8700
gcggtaagat ccttgagagt tttcgccccg aagaacgttt tccaatgatg agcactttta    8760
aagttctgct atgtggcgcg gtattatccc gtattgacgc cgggcaagag caactcggtc    8820
gccgcataca ctattctcag aatgacttgg ttgagtactc accagtcaca gaaaagcatc    8880
ttacggatgg catgacagta agagaattat gcagtgctgc cataaccatg agtgataaca    8940
ctgcggccaa cttacttctg acaacgatcg gaggaccgaa ggagctaacc gcttttttgc    9000
acaacatggg ggatcatgta actcgccttg atcgttggga accggagctg aatgaagcca    9060
taccaaacga cgagcgtgac accacgatgc ctgtagcaat ggcaacaacg ttgcgcaaac    9120
```

-continued

```
tattaactgg cgaactactt actctagctt cccggcaaca attaatagac tggatggagg    9180
cggataaagt tgcaggacca cttctgcgct cggcccttcc ggctggctgg tttattgctg    9240
ataaatctgg agccggtgag cgtgggtctc gcggtatcat tgcagcactg gggccagatg    9300
gtaagccctc ccgtatcgta gttatctaca cgacggggag tcaggcaact atggatgaac    9360
gaaatagaca gatcgctgag ataggtgcct cactgattaa gcattggtaa ctgtcagacc    9420
aagtttactc atatatactt tagattgatt taaaacttca tttttaattt aaaaggatct    9480
aggtgaagat cctttttgat aatctcatga ccaaaatccc ttaacgtgag ttttcgttcc    9540
actgagcgtc agaccccgta gaaaagatca aaggatcttc ttgagatcct ttttttctgc    9600
gcgtaatctg ctgcttgcaa acaaaaaaac caccgctacc agcggtggtt tgtttgccgg    9660
atcaagagct accaactctt tttccgaagg taactggctt cagcagagcg cagataccaa    9720
atactgttct tctagtgtag ccgtagttag gccaccactt caagaactct gtagcaccgc    9780
ctacatacct cgctctgcta atcctgttac cagtggctgc tgccagtggc gataagtcgt    9840
gtcttaccgg gttggactca agacgatagt taccggataa ggcgcagcgg tcgggctgaa    9900
cggggggttc gtgcacacag cccagcttgg agcgaacgac ctacaccgaa ctgagatacc    9960
tacagcgtga gctatgagaa agcgccacgc ttcccgaagg gagaaaggcg gacaggtatc   10020
cggtaagcgg cagggtcgga acaggagagc gcacgaggga gcttccaggg ggaaacgcct   10080
ggtatcttta tagtcctgtc gggtttcgcc acctctgact tgagcgtcga ttttgtgat   10140
gctcgtcagg gggcggagc ctatggaaaa acgccagcaa cgcggccttt ttacggttcc   10200
tggccttttg ctggcctttt gctcacatgt tctttcctgc gttatcccct gattctgtgg   10260
ataaccgtat taccgccttt gagtgagctg ataccgctcg ccgcagccga acgaccgagc   10320
gcagcgagtc agtgagcgag gaagcggaag agcgcccaat acgcaaaccg cctctccccg   10380
cgcgttggcc gattcattaa tgcagctgtg aatgtgtgt cagttagggt gtggaaagtc   10440
cccaggctcc ccagcaggca gaagtatgca aagcatgcat ctcaattagt cagcaaccag   10500
gtgtggaaag tccccaggct ccccagcagg cagaagtatg caaagcatgc atctcaatta   10560
gtcagcaacc atagtcccgc ccctaactcc gcccatcccg cccctaactc cgcccagttc   10620
cgcccattct ccgccccatg ctgactaat tttttttatt tatgcagagg ccgaggccgc   10680
ctcggcctct gagctattcc agaagtagtg aggaggcttt tttggaggcc taggcttttg   10740
caaaaagctt ggacacaaga caggcttgcg agatatgttt gagaatacca ctttatcccg   10800
cgtcagggag aggcagtgcg taaaaagacg cggactcatg tgaaatactg gtttttagtg   10860
cgccagatct ctataatctc gcgcaaccta ttttcccctc gaacacttttt aagccgtag   10920
ataaacaggc tgggacactt cacatgagcg aaaaatacat cgtcacctgg gacatgttgc   10980
agatccatgc acgtaaactc gcaagccgac tgatgccttc tgaacaatgg aaaggcatta   11040
ttgccgtaag ccgtggcggt ctgtaccggg tgcgttactg gcgcgtgaac tgggtattcg   11100
tcatgtcgat accgtttgta tttccagcta cgatcacgac aaccagcgcg agcttaaagt   11160
gctgaaacgc gcagaaggcg atggcgaagg cttcatcgtt attgatgacc tggtggatac   11220
cggtggtact gcggttgcga ttcgtgaaat gtatccaaaa gcgcactttg tcaccatctt   11280
cgcaaaaccg gctggtcgtc cgctggttga tgactatgtt gttgatatcc gcaagatac   11340
ctggattgaa cagccgtggg atatgggcgt cgtattcgtc ccgccaatct ccggtcgcta   11400
atcttttcaa cgcctggcac tgccgggcgt tgttcttttt aacttcaggc gggttacaat   11460
```

```
agtttccagt aagtattctg gaggctgcat ccatgacaca ggcaaacctg agcgaaaccc    11520
tgttcaaacc ccgcttttaaa catcctgaaa cctcgacgct agtccgccgc tttaatcacg    11580
gcgcacaacc gcctgtgcag tcggcccttg atggtaaaac catccctcac tggtatcgca    11640
tgattaaccg tctgatgtgg atctggcgcg gcattgaccc acgcgaaatc ctcgacgtcc    11700
aggcacgtat tgtgatgagc gatgccgaac gtaccgacga tgatttatac gatacggtga    11760
ttggctaccg tggcggcaac tggatttatg agtgggcccc ggatcttgt gaaggaacct    11820 tacttctgtg gtgtgacata attggacaaa ctacctacag agatttaaag ctctaaggta    11880
aatataaaat ttttaagtgt ataatgtgtt aaactactga ttctaattgt ttgtgtattt    11940
tagattccaa cctatggaac tgatgaatgg gagcagtggt ggaatgcctt taatgaggaa    12000
aacctgtttt gctcagaaga aatgccatct agtgatgatg aggctactgc tgactctcaa    12060
cattctactc ctccaaaaaa gaagagaaag gtagaagacc ccaaggactt ccttcagaa    12120 ttgctaagtt ttttgagtca tgctgtgttt agtaatagaa ctcttgcttg ctttgctatt    12180
tacaccacaa aggaaaaagc tgcactgcta tacaagaaaa ttatgaaaaa atattctgta    12240
acctttataa gtaggcataa cagttataat cataacatac tgttttttct tactccacac    12300
aggcatagag tgtctgctat taataactat gctcaaaaat tgtgtacctt tagcttttta    12360
atttgtaaag gggttaataa ggaatatttg atgtatagtg ccttgactag agatcataat    12420
cagccatacc acatttgtag aggttttact tgctttaaaa aacctcccac acctcccct    12480 gaacctgaaa cataaaatga atgcaattgt tgttgttaac ttgtttattg cagcttataa    12540
tggttacaaa taaagcaata gcatcacaaa tttcacaaat aaagcatttt ttcactgca    12600 ttctagttgt ggtttgtcca aactcatcaa tgtatcttat catgtctgga tcaactggat    12660
aactcaagct aaccaaaatc atcccaaact tcccacccca taccctatta ccactgcc    12718

<210> SEQ ID NO 2
<211> LENGTH: 118
<212> TYPE: DNA
<213> ORGANISM: Artificial Sequence
<220> FEATURE:
<223> OTHER INFORMATION: Synthetic Construct (cPPT Seq)

<400> SEQUENCE: 2
ttttaaaaga aaagggggga ttgggggta cagtgcaggg gaaagaatag tagacataat     60
agcaacagac atacaaacta agaattaca aaaacaaatt acaaaaattc aaaattttt    118

<210> SEQ ID NO 3
<211> LENGTH: 592
<212> TYPE: DNA
<213> ORGANISM: Woodchuck hepatitis virus

<400> SEQUENCE: 3
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga ctttcgcttt ccccctccct    300
attgccacgg cggaactcat cgccgcctgc cttgcccgct gctggacagg gctcggctg    360 ttgggcactg acaattccgt ggtgttgtcg gggaagctga cgtcctttcc atggctgctc    420
gcctgtgttg ccacctggat tctgcgcggg acgtccttct gctacgtccc ttcggccctc    480
```

| | |
|---|---|
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 4
<211> LENGTH: 5048
<212> TYPE: DNA
<213> ORGANISM: Artificial Sequence
<220> FEATURE:
<223> OTHER INFORMATION: Synthetic Construct (pORF-hIL-12 Sequence)

<400> SEQUENCE: 4

| | |
|---|---|
| ggatctgcga tcgctccggt gcccgtcagt gggcagagcg cacatcgccc acagtccccg | 60 |
| agaagttggg gggaggggtc ggcaattgaa ccggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacgtaagt gatatctact agatttatca aaaagagtgt tgacttgtga gcgctcacaa | 600 |
| ttgatactta gattcatcga gagggacacg tcgactacta accttcttct ctttcctaca | 660 |
| gctgagatca ccggcgaagg agggccacca tgggtcacca gcagttggtc atctcttggt | 720 |
| tttccctggt ttttctggca tctccctcg tggccatatg ggaactgaag aaagatgttt | 780 |
| atgtcgtaga attggattgg tatccggatg cccctggaga aatggtggtc ctcacctgtg | 840 |
| acacccctga agaagatggt atcacctgga ccttggacca gagcagtgag gtcttaggct | 900 |
| ctggcaaaac cctgaccatc caagtcaaag agtttggaga tgctggccag tacacctgtc | 960 |
| acaaaggagg cgaggttcta agccattcgc tcctgctgct tcacaaaaag gaagatggaa | 1020 |
| tttggtccac tgatatttta aaggaccaga agaacccaa aaataagacc tttctaagat | 1080 |
| gcgaggccaa gaattattct ggacgtttca cctgctggtg gctgacgaca atcagtactg | 1140 |
| atttgacatt cagtgtcaaa agcagcagag gctcttctga ccccaaggg gtgacgtgcg | 1200 |
| gagctgctac actctctgca gagagagtca gagggacaa caaggagtat gagtactcag | 1260 |
| tggagtgcca ggaggacagt gcctgcccag ctgctgagga gagtctgccc attgaggtca | 1320 |
| tggtggatgc cgttcacaag ctcaagtatg aaaactacac cagcagcttc ttcatcaggg | 1380 |
| acatcatcaa acctgaccca cccaagaact gcagctgaa gccattaaag aattctcggc | 1440 |
| aggtggaggt cagctgggag taccctgaca cctggagtac tccacattcc tacttctccc | 1500 |
| tgacattctg cgttcaggtc cagggcaaga gcaagagaga aagaaagat agagtcttca | 1560 |
| cggacaagac ctcagccacg gtcatctgcc gcaaaaatgc cagcattagc gtgcgggccc | 1620 |
| aggaccgcta ctatagctca tcttggagcg aatgggcatc tgtgccctgc agtgttcctg | 1680 |
| gagtaggggt acctggggtg ggcgccagaa acctccccgt ggccactcca gacccaggaa | 1740 |
| tgttcccatg ccttcaccac tcccaaaacc tgctgagggc cgtcagcaac atgctccaga | 1800 |
| aggccagaca aactctagaa ttttacccct gcacttctga agagattgat catgaagata | 1860 |
| tcacaaaaga taaaaccagc acagtggagg cctgtttacc attggaatta accaagaatg | 1920 |

```
agagttgcct aaattccaga gagacctctt tcataactaa tgggagttgc ctggcctcca    1980
gaaagacctc ttttatgatg gccctgtgcc ttagtagtat ttatgaagac tcgaagatgt    2040
accaggtgga gttcaagacc atgaatgcaa agcttctgat ggatcctaag aggcagatct    2100
ttctagatca aaacatgctg gcagttattg atgagctgat gcaggccctg aatttcaaca    2160
gtgagactgt gccacaaaaa tcctcccttg aagaaccgga ttttttataaa actaaaatca    2220
agctctgcat acttcttcat gcttttcagaa ttcgggcagt gactattgat agagtgatga    2280
gctatctgaa tgcttcctaa aaagcgaggt ccctccaaac cgttgtcatt tttataaaac    2340
tttgaaatga ggaaactttg ataggatgtg gattaagaac tagggagggg gaaagaagga    2400
tgggactatt acatccacat gatacctctg atcaagtatt tttgacattt actgtggata    2460
aattgttttt aagttttcat gaatgaattg ctaagaaggg gggaattctt ttgctttttta   2520
ccctcgacta gctcgacatg ataagataca ttgatgagtt tggacaaacc acaactagaa    2580
tgcagtgaaa aaaatgcttt atttgtgaaa tttgtgatgc tattgcttta tttgtgaaat    2640
ttgtgatgct attgctttat ttgtaaccat tataagctgc aataaacaag ttaacaacaa    2700
caattgcatt catttatgt ttcaggttca ggggaggtg tgggaggttt tttaaagcaa       2760
gtaaaacctc tacaaatgtg gtagatcatt taaatgttaa ttaagaacat gtgagcaaaa    2820
ggccagcaaa aggccaggaa ccgtaaaaag gccgcgttgc tggcgttttt ccataggctc    2880
cgccccctg acgagcatca caaaaatcga cgctcaagtc agaggtggcg aaacccgaca      2940
ggactataaa gataccaggc gtttccccct ggaagctccc tcgtgcgctc tcctgttccg    3000
accctgccgc ttaccggata cctgtccgcc tttctccctt cgggaagcgt ggcgctttct    3060
caatgctcac gctgtaggta tctcagttcg gtgtaggtcg ttcgctccaa gctgggctgt    3120
gtgcacgaac cccccgttca gcccgaccgc tgcgccttat ccggtaacta tcgtcttgag    3180
tccaacccgg taagacacga cttatcgcca ctggcagcag ccactggtaa caggattagc    3240
agagcgaggt atgtaggcgg tgctacagag ttcttgaagt ggtggcctaa ctacggctac    3300
actagaagaa cagtatttgg tatctgcgct ctgctgaagc cagttacctt cggaaaaaga    3360
gttggtagct cttgatccgg caaacaaacc accgctggta gcggtggttt ttttgtttgc    3420
aagcagcaga ttacgcgcag aaaaaaagga tctcaagaag atcctttgat cttttctacg    3480
gggtctgacg ctcagtggaa cgaaaactca cgttaaggga ttttggtcat gagattatca    3540
aaaaggatct tcacctagat ccttttaaat taaaaatgaa gttttaaatc aatctaaagt    3600
atatatgagt aaacttggtc tgacagttac caatgcttaa tcagtgaggc acctatctca    3660
gcgatctgtc tatttcgttc atccatagtt gcctgactcc ccgtcgtgta gataactacg    3720
atacgggagg gcttaccatc tggccccagt gctgcaatga taccgcgaga cccacgctca    3780
ccggctccag atttatcagc aataaaccag ccagccggaa gggccgagcg cagaagtggt    3840
cctgcaactt tatccgcctc catccagtct attaattgtt gccgggaagc tagagtaagt    3900
agttcgccag ttaatagttt gcgcaacgtt gttgccattg ctacaggcat cgtggtgtca    3960
cgctcgtcgt ttggtatggc ttcattcagc tccggttccc aacgatcaag gcgagttaca    4020
tgatccccca tgttgtgcaa aaaagcggtt agctccttcg gtcctccgat cgttgtcaga    4080
agtaagttgg ccgcagtgtt atcactcatg gttatggcag cactgcataa ttctcttact    4140
gtcatgccat ccgtaagatg cttttctgtg actggtgagt actcaaccaa gtcattctga    4200
gaatagtgta tgcggcgacc gagttgctct tgcccggcgt caatacggga taataccgcg    4260
ccacatagca gaactttaaa agtgctcatc attggaaaac gttcttcggg gcgaaaactc    4320
```

```
tcaaggatct taccgctgtt gagatccagt tcgatgtaac ccactcgtgc acccaactga    4380
tcttcagcat cttttacttt caccagcgtt tctgggtgag caaaaacagg aaggcaaaat    4440
gccgcaaaaa agggaataag ggcgacacgg aaatgttgaa tactcatact cttcctttttt   4500 caatattatt gaagcattta tcagggttat tgtctcatga gcggatacat atttgaatgt    4560
atttagaaaa ataaacaaat aggggttccg cgcacatttc cccgaaaagt gccacctgac    4620
gtctaagaaa ccattattat catgacatta acctataaaa ataggcgtat cacgaggccc    4680
tttcgtctcg cgcgtttcgg tgatgacggt gaaaacctct gacacatgca gctcccggag    4740
acggtcacag cttgtctgta agcggatgcc gggagcagac aagcccgtca gggcgcgtca    4800
gcgggtgttg gcgggtgtcg ggctggctt  aactatgcgg catcagagca gattgtactg    4860
agagtgcacc atatggatct cgagcggccg caataaaata tctttatttt cattacatct    4920
gtgtgttggt ttttgtgtg  aatcgtaact aacatacgct ctccatcaaa acaaaacgaa    4980
acaaaacaaa ctagcaaaat aggctgtccc cagtgcaagt gcaggtgcca gaacatttct    5040
ctatcgaa                                                             5048

<210> SEQ ID NO 5
<211> LENGTH: 4846
<212> TYPE: DNA
<213> ORGANISM: Artificial Sequence
<220> FEATURE:
<223> OTHER INFORMATION: Synthetic Construct (pORF-mIL-12 (p35p40)
      Sequence)

<400> SEQUENCE: 5
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgagggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacgtaagt gatatctact agatttatca aaaagagtgt tgacttgtga gcgctcacaa    600
ttgatactta gattcatcga gagggacacg tcgactacta accttcttct ctttcctaca    660
gctgagatca ccggcgaagg agggccacca tgggtcaatc acgctacctc ctctttttgg    720
ccacccttgc cctcctaaac cacctcagtt tggccagggt cattccagtc tctggacctg    780
ccaggtgtct tagccagtcc cgaaacctgc tgaagaccac agatgacatg gtgaagacgg    840
ccagagaaaa gctgaaacat tattcctgca ctgctgaaga catcgatcat gaagacatca    900
cacgggacca aaccagcaca ttgaagacct gtttaccact ggaactacac aagaacgaga    960
gttgcctggc tactagagag acttcttcca acaagagg  gagctgcctg cccccacaga   1020
agacgtcttt gatgatgacc ctgtgccttg gtagcatcta tgaggacttg aagatgtacc   1080
agacagagtt ccaggccatc aacgcagcac ttcagaatca caaccatcag cagatcattc   1140
tagacaaggg catgctggtg gccatcgatg agctgatgca gtctctgaat cataatggcg   1200
agactctgcg ccagaaacct cctgtgggag aagcagaccc ttacagagtg aaaatgaagc   1260
```

```
tctgcatcct gcttcacgcc ttcagcaccc gcgtcgtgac catcaacagg gtgatgggct   1320
atctgagctc cgccgttcct ggagtagggg tacctggagt gggcggatct atgtgggagc   1380
tggagaaaga cgtttatgtt gtagaggtgg actggactcc cgatgcccct ggagaaacag   1440
tgaacctcac ctgtgacacg cctgaagaag atgacatcac ctggacctca gaccagagac   1500
atggagtcat aggctctgga aagaccctga ccatcactgt caaagagttt ctagatgctg   1560
gccagtacac ctgccacaaa ggaggcgaga ctctgagcca ctcacatctg ctgctccaca   1620
agaaggaaaa tggaatttgg tccactgaaa ttttaaaaaa tttcaaaaac aagactttcc   1680
tgaagtgtga agcaccaaat tactccggac ggttcacgtg ctcatggctg gtgcaaagaa   1740
acatggactt gaagttcaac atcaagagca gtagcagtcc ccccgactct cgggcagtga   1800
catgtggaat ggcgtctctg tctgcagaga aggtcacact ggaccaaagg gactatgaga   1860
agtattcagt gtcctgccag gaggatgtca cctgcccaac tgccgaggag accctgccca   1920
ttgaactggc gttggaagca cggcagcaga ataaatatga aactacagc accagcttct   1980
tcatcaggga catcatcaaa ccagacccgc caagaacctt gcagatgaag cctttgaaga   2040
actcacaggt ggaggtcagc tgggagtacc ctgactcctg gagcactccc cattcctact   2100
tctccctcaa gttctttgtt cgaatccagc gcaagaaaga aaagatgaag gagacagagg   2160
aggggtgtaa ccagaaaggt gcgttcctcg tagagaagac atctaccgaa gtccaatgca   2220
aaggcgggaa tgtctgcgtg caagctcagg atcgctatta caattcctca tgcagcaagt   2280
gggcatgtgt tccctgcagg gtccgatcct aggatgcaac ggatgctagc tcgacatgat   2340
aagatacatt gatgagtttg gacaaaccac aactagaatg cagtgaaaaa aatgctttat   2400
ttgtgaaatt tgtgatgcta ttgctttatt tgtgaaattt gtgatgctat tgctttattt   2460
gtaaccatta taagctgcaa taaacaagtt aacaacaaca attgcattca ttttatgttt   2520
caggttcagg gggaggtgtg ggaggttttt taaagcaagt aaaacctcta caaatgtggt   2580
agatcattta aatgttaatt aagaacatgt gagcaaaagg ccagcaaaag gccaggaacc   2640
gtaaaaaggc cgcgttgctg gcgttttttcc ataggctccg ccccctgac gagcatcaca   2700
aaaatcgacg ctcaagtcag aggtggcgaa acccgacagg actataaaga taccaggcgt   2760
ttccccctgg aagctccctc gtgcgctctc ctgttccgac cctgccgctt accggatacc   2820
tgtccgcctt tctcccttcg ggaagcgtgg cgctttctca atgctcacgc tgtaggtatc   2880
tcagttcggt gtaggtcgtt cgctccaagc tgggctgtgt gcacgaaccc cccgttcagc   2940
ccgaccgctg cgccttatcc ggtaactatc gtcttgagtc aacccggta agacacgact   3000
tatcgccact ggcagcagcc actggtaaca ggattagcag agcgaggtat gtaggcggtg   3060
ctacagagtt cttgaagtgg tggcctaact acggctacac tagaagaaca gtatttggta   3120
tctgcgctct gctgaagcca gttaccttcg gaaaaagagt tggtagctct tgatccggca   3180
aacaaaccac cgctggtagc ggtggttttt tgtttgcaa gcagcagatt acgcgcagaa   3240
aaaaaggatc tcaagaagat cctttgatct tttctacggg gtctgacgct cagtggaacg   3300
aaaactcacg ttaagggatt ttggtcatga gattatcaaa aaggatcttc acctagatcc   3360
ttttaaatta aaaatgaagt tttaaatcaa tctaaagtat atatgagtaa acttggtctg   3420
acagttacca atgcttaatc agtgaggcac ctatctcagc gatctgtcta tttcgttcat   3480
ccatagttgc ctgactcccc gtcgtgtaga taactacgat acgggagggc ttaccatctg   3540
gccccagtgc tgcaatgata ccgcgagacc cacgctcacc ggctccagat ttatcagcaa   3600
```

-continued

| | | | | |
|---|---|---|---|---|
| taaaccagcc | agccggaagg | gccgagcgca | gaagtggtcc | tgcaacttta tccgcctcca | 3660 |
| tccagtctat | taattgttgc | cgggaagcta | gagtaagtag | ttcgccagtt aatagtttgc | 3720 |
| gcaacgttgt | tgccattgct | acaggcatcg | tggtgtcacg | ctcgtcgttt ggtatggctt | 3780 |
| cattcagctc | cggttcccaa | cgatcaaggc | gagttacatg | atcccccatg ttgtgcaaaa | 3840 |
| aagcggttag | ctccttcggt | cctccgatcg | ttgtcagaag | taagttggcc gcagtgttat | 3900 |
| cactcatggt | tatggcagca | ctgcataatt | ctcttactgt | catgccatcc gtaagatgct | 3960 |
| tttctgtgac | tggtgagtac | tcaaccaagt | cattctgaga | atagtgtatg cggcgaccga | 4020 |
| gttgctcttg | cccggcgtca | atacgggata | ataccgcgcc | acatagcaga actttaaaag | 4080 |
| tgctcatcat | tggaaaacgt | tcttcgggc | gaaaactctc | aaggatctta ccgctgttga | 4140 |
| gatccagttc | gatgtaaccc | actcgtgcac | ccaactgatc | ttcagcatct tttactttca | 4200 |
| ccagcgtttc | tgggtgagca | aaaacaggaa | ggcaaaatgc | cgcaaaaaag gaataaggg | 4260 |
| cgacacggaa | atgttgaata | ctcatactct | tcctttttca | atattattga agcatttatc | 4320 |
| agggttattg | tctcatgagc | ggatacatat | ttgaatgtat | ttagaaaaat aaacaaatag | 4380 |
| gggttccgcg | cacatttccc | cgaaaagtgc | cacctgacgt | ctaagaaacc attattatca | 4440 |
| tgacattaac | ctataaaaat | aggcgtatca | cgaggccctt | tcgtctcgcg cgtttcggtg | 4500 |
| atgacggtga | aaacctctga | cacatgcagc | tcccggagac | ggtcacagct tgtctgtaag | 4560 |
| cggatgccgg | gagcagacaa | gcccgtcagg | gcgcgtcagc | gggtgttggc gggtgtcggg | 4620 |
| gctggcttaa | ctatgcggca | tcagagcaga | ttgtactgag | agtgcaccat atggatctcg | 4680 |
| agcggccgca | ataaaatatc | tttatttca | ttacatctgt | gtgttggttt tttgtgtgaa | 4740 |
| tcgtaactaa | catacgctct | ccatcaaaac | aaaacgaaac | aaaacaaact agcaaaatag | 4800 |
| gctgtcccca | gtgcaagtgc | aggtgccaga | acatttctct | atcgaa | 4846 |

<210> SEQ ID NO 6
<211> LENGTH: 639
<212> TYPE: DNA
<213> ORGANISM: Homo sapiens
<220> FEATURE:
<221> NAME/KEY: misc_feature
<223> OTHER INFORMATION: tmpk wt

<400> SEQUENCE: 6

| | | | | |
|---|---|---|---|---|
| atggcggccc | ggcgcggggc | tctcatagtg | ctggagggcg | tggaccgcgc cgggaagagc | 60 |
| acgcagagcc | gcaagctggt | ggaagcgctg | tgcgccgcgg | ccaccgcgc cgaactgctc | 120 |
| cggttcccgg | aaagatcaac | tgaaatcggc | aaacttctga | gttcctactt gcaaaagaaa | 180 |
| agtgacgtgg | aggatcactc | ggtgcacctg | ctttttttctg | caaatcgctg gaacaagtg | 240 |
| ccgttaatta | aggaaaagtt | gagccagggc | gtgaccctcg | tcgtggacag atacgcattt | 300 |
| tctggtgtgg | ccttcaccgg | tgccaaggag | aattttttccc | tagattggtg taaacagcca | 360 |
| gacgtgggc | ttcccaaacc | cgacctggtc | ctgttcctcc | agttacagct ggcggatgct | 420 |
| gccaagcggg | gagcgtttgg | ccatgagcgc | tatgagaacg | ggctttcca ggagcgggcg | 480 |
| ctccggtgtt | tccaccagct | catgaaagac | acgactttga | actggaagat ggtggatgct | 540 |
| tccaaaagca | tcgaagctgt | ccatgaggac | atccgcgtgc | tctctgagga cgccatccgc | 600 |
| actgccacag | agaagccgct | gggggagcta | tggaagtga | | 639 |

<210> SEQ ID NO 7
<211> LENGTH: 212
<212> TYPE: PRT

```
<213> ORGANISM: Homo sapiens
<220> FEATURE:
<221> NAME/KEY: MISC_FEATURE
<223> OTHER INFORMATION: tmpk wt

<400> SEQUENCE: 7

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
            165                 170                 175

Met Val Asp Ala Ser Lys Ser Ile Glu Ala Val His Glu Asp Ile Arg
        180                 185                 190

Val Leu Ser Glu Asp Ala Ile Arg Thr Ala Thr Glu Lys Pro Leu Gly
    195                 200                 205

Glu Leu Trp Lys
    210

<210> SEQ ID NO 8
<211> LENGTH: 639
<212> TYPE: DNA
<213> ORGANISM: Homo sapiens
<220> FEATURE:
<221> NAME/KEY: misc_feature
<223> OTHER INFORMATION: tmpk wt

<400> SEQUENCE: 8
atggcggccc ggcgcggggc tctcatagtg ctggagggcg tggaccgcgc cgggaagagc      60
acgcagagcc gcaagctggt ggaagcgctg tgcgccgcgg gccaccgcgc cgaactgctc     120
cggttcccgg aaagatcaac tgaaatcggc aaacttctga gttcctactt gcaaagaaa     180 agtgacgtgg aggatcactc ggtgcacctg ctttttttctg caaatcgctg gaacaagtg     240 ccgttaatta aggaaaagtt gagccagggc gtgaccctcg tcgtggacag atacgcattt     300
tctggtgtgg ccttcaccgg tgccaaggag aatttttccc tagattggtg taaacagcca     360
gacgtgggcc ttcccaaacc cgacctggtc ctgttcctcc agttacagct ggcggatgct     420
gccaagcggg gagcgtttgg ccatgagcgc tatgagaacg gggctttcca ggagcgggcg     480
ctccggtgtt tccaccagct catgaaagac acgactttga actggaagat ggtgatgct     540 tccaaaagca tcgaagctgt ccatgaggac atccgcgtgc tctctgagga cgccatccgc     600
```

```
actgccacag agaagccgct gggggagcta tggaagtga                              639
```

<210> SEQ ID NO 9
<211> LENGTH: 212
<212> TYPE: PRT
<213> ORGANISM: Homo sapiens
<220> FEATURE:
<221> NAME/KEY: MISC_FEATURE
<223> OTHER INFORMATION: tmpk wt

<400> SEQUENCE: 9

```
Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175

Met Val Asp Ala Ser Lys Ser Ile Glu Ala Val His Glu Asp Ile Arg
            180                 185                 190

Val Leu Ser Glu Asp Ala Ile Arg Thr Ala Thr Glu Lys Pro Leu Gly
        195                 200                 205

Glu Leu Trp Lys
    210
```

<210> SEQ ID NO 10
<211> LENGTH: 636
<212> TYPE: DNA
<213> ORGANISM: Homo sapiens
<220> FEATURE:
<221> NAME/KEY: misc_feature
<223> OTHER INFORMATION: tmpk wt

<400> SEQUENCE: 10

```
atggcggccc ggcgcggggc tctcatagtg ctgggggcg tggaccgcgc cgggaagagc       60
acgcagagcc gcaagctggt ggaagcgctg tcgcgcgggc caccgcccga actgctccgg     120
ttcccggaaa gatcaactga aatcggcaaa cttctgagtt cctacttgca aaagaaaagt     180
gacgtggagg atcactcggt gcacctgctt ttttctgcaa atcgctggga acaagtgccg     240
ttaattaagg aaaagttgag ccagggcgtg accctcgtcg tggacagata cgcatttcct    300
ggtgtggcct tcaccggtgc caaggagaat ttttcccctag actggtgtaa acagccagac    360
```

-continued

```
gtgggccttc ccaaacccga cctggtcctg ttcctccagt tacagctggc ggatgctgcc    420
aagcggggag cgtttggcca tgagcgctat gagaacgggg ctttccagga gcgggcgctc    480
cggtgtttcc accagctcat gaaagacacg actttgaact ggaagatggt ggatgcttcc    540
aaaagactcg aagctgtcca tgaggaactc cgcgtgctct ctgaggacgc catccgcact    600
gccacagaga agccgctggg ggagctatgg aagtga                              636
```

<210> SEQ ID NO 11
<211> LENGTH: 211
<212> TYPE: PRT
<213> ORGANISM: Homo sapiens
<220> FEATURE:
<221> NAME/KEY: MISC_FEATURE
<223> OTHER INFORMATION: tmpk wt

<400> SEQUENCE: 11

```
Met Ala Ala Arg Arg Gly Ala Leu Ile Val Leu Glu Gly Val Asp Arg
1               5                   10                  15
Ala Gly Lys Ser Thr Gln Ser Arg Lys Leu Val Glu Ala Leu Ser Arg
            20                  25                  30
Gly Pro Pro Glu Leu Leu Arg Phe Pro Glu Arg Ser Thr Glu Ile
        35                  40                  45
Gly Lys Leu Leu Ser Ser Tyr Leu Gln Lys Lys Ser Asp Val Glu Asp
    50                  55                  60
His Ser Val His Leu Leu Phe Ser Ala Asn Arg Trp Glu Gln Val Pro
65                  70                  75                  80
Leu Ile Lys Glu Lys Leu Ser Gln Gly Val Thr Leu Val Val Asp Arg
                85                  90                  95
Tyr Ala Phe Ser Gly Val Ala Phe Thr Gly Ala Lys Glu Asn Phe Ser
            100                 105                 110
Leu Asp Trp Cys Lys Gln Pro Asp Val Gly Leu Pro Lys Pro Asp Leu
        115                 120                 125
Val Leu Phe Leu Gln Leu Gln Leu Ala Asp Ala Ala Lys Arg Gly Ala
    130                 135                 140
Phe Gly His Glu Arg Tyr Glu Asn Gly Ala Phe Gln Glu Arg Ala Leu
145                 150                 155                 160
Arg Cys Phe His Gln Leu Met Lys Asp Thr Thr Leu Asn Trp Lys Met
                165                 170                 175
Val Asp Ala Ser Lys Arg Leu Glu Ala Val His Glu Glu Leu Arg Val
            180                 185                 190
Leu Ser Glu Asp Ala Ile Arg Thr Ala Thr Glu Lys Pro Leu Gly Glu
        195                 200                 205
Leu Trp Lys
    210
```

<210> SEQ ID NO 12
<211> LENGTH: 639
<212> TYPE: DNA
<213> ORGANISM: Homo sapiens
<220> FEATURE:
<221> NAME/KEY: misc_feature
<223> OTHER INFORMATION: tmpk wt (no stop codons)

<400> SEQUENCE: 12

```
atggcggccc ggcgcgggc tctcatagtg ctggagggcg tggaccgcgc cggaagagc      60 acgcagagcc gcaagctggt ggaagcgctg tgcgccgcgg ccaccgcgc cgaactgctc    120 cggttcccgg aaagatcaac tgaaatcggc aaacttctga gttcctactt gcaaaagaaa   180
```

```
agtgacgtgg aggatcactc ggtgcacctg ctttttttctg caaatcgctg ggaacaagtg    240
ccgttaatta aggaaaagtt gagccagggc gtgaccctcg tcgtggacag atacgcattt    300
tctggtgtgg ccttcaccgg tgccaaggag aatttttccc tagattggtg taaacagcca    360
gacgtgggcc ttcccaaacc cgacctggtc ctgttcctcc agttacagct ggcggatgct    420
gccaagcggg gagcgtttgg ccatgagcgc tatgagaacg gggcttttcca ggagcgggcg    480 ctccggtgtt tccaccagct catgaaagac acgactttga actggaagat ggtggatgct    540
tccaaaagca tcgaagctgt ccatgaggac atccgcgtgc tctctgagga cgccatccgc    600
actgccacag agaagccgct gggggagcta tggaaggac                          639
```

<210> SEQ ID NO 13
<211> LENGTH: 213
<212> TYPE: PRT
<213> ORGANISM: Homo sapiens
<220> FEATURE:
<221> NAME/KEY: MISC_FEATURE
<223> OTHER INFORMATION: tmpk wt putative sequence

<400> SEQUENCE: 13

```
Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175

Met Val Asp Ala Ser Lys Ser Ile Glu Ala Val His Gly Asp Ile Arg
            180                 185                 190

Val Leu Ser Glu Asp Ala Ile Arg Thr Ala Thr Glu Lys Pro Leu Gly
        195                 200                 205

Glu Leu Trp Lys Asp
    210
```

<210> SEQ ID NO 14
<211> LENGTH: 639
<212> TYPE: DNA
<213> ORGANISM: Mus musculus
<220> FEATURE:
<221> NAME/KEY: misc_feature
<223> OTHER INFORMATION: tmpk wt

<400> SEQUENCE: 14

```
atggcgtcgc gtcggggagc gctcatcgtg ctggagggtg tggaccgtgc tggcaagacc      60
acgcagggcc tcaagctggt gaccgcgctg tgcgcctcgg gccacagagc ggagctgctg     120
cgtttccccg aaagatcaac ggaaatcggc aagcttctga attcctactt ggaaaagaaa     180
acggaactag aggatcactc cgtgcacctg ctcttctctg caaaccgctg ggaacaagta     240
ccattaatta aggcgaagtt gaaccagggt gtgaccccttg ttttggacag atacgccttt    300
tctggggttg ccttcactgg tgccaaagag aattttttcc tggattggtg taaacaaccg     360
gacgtgggcc ttcccaaacc tgacctgatc ctgttccttc agttacaatt gctggacgct     420
gctgcacggg gagagtttgg ccttgagcga tatgagaccg gactttccca aaagcaggtt     480
ctgttgtgtt tccagcagct catggaagag aaaaacctca actggaaggt ggttgatgct     540
tccaaaagca ttgaggaagt ccataaagaa atccgtgcac actctgagga cgccatccga     600
aacgctgcac agaggccact gggggagcta tggaaataa                            639
```

<210> SEQ ID NO 15
<211> LENGTH: 212
<212> TYPE: PRT
<213> ORGANISM: Mus musculus
<220> FEATURE:
<221> NAME/KEY: MISC_FEATURE
<223> OTHER INFORMATION: tmpk wt

<400> SEQUENCE: 15

```
Met Ala Ser Arg Arg Gly Ala Leu Ile Val Leu Glu Gly Val Asp Arg
1               5                   10                  15
Ala Gly Lys Thr Thr Gln Gly Leu Lys Leu Val Thr Ala Leu Cys Ala
            20                  25                  30
Ser Gly His Arg Ala Glu Leu Leu Arg Phe Pro Glu Arg Ser Thr Glu
        35                  40                  45
Ile Gly Lys Leu Leu Asn Ser Tyr Leu Glu Lys Lys Thr Glu Leu Glu
    50                  55                  60
Asp His Ser Val His Leu Leu Phe Ser Ala Asn Arg Trp Glu Gln Val
65                  70                  75                  80
Pro Leu Ile Lys Ala Lys Leu Asn Gln Gly Val Thr Leu Val Leu Asp
                85                  90                  95
Arg Tyr Ala Phe Ser Gly Val Ala Phe Thr Gly Ala Lys Glu Asn Phe
            100                 105                 110
Ser Leu Asp Trp Cys Lys Gln Pro Asp Val Gly Leu Pro Lys Pro Asp
        115                 120                 125
Leu Ile Leu Phe Leu Gln Leu Gln Leu Leu Asp Ala Ala Ala Arg Gly
    130                 135                 140
Glu Phe Gly Leu Glu Arg Tyr Glu Thr Gly Thr Phe Gln Lys Gln Val
145                 150                 155                 160
Leu Leu Cys Phe Gln Gln Leu Met Glu Glu Lys Asn Leu Asn Trp Lys
                165                 170                 175
Val Val Asp Ala Ser Lys Ser Ile Glu Glu Val His Lys Glu Ile Arg
            180                 185                 190
Ala His Ser Glu Asp Ala Ile Arg Asn Ala Ala Gln Arg Pro Leu Gly
        195                 200                 205
Glu Leu Trp Lys
    210
```

<210> SEQ ID NO 16

-continued

```
<211> LENGTH: 212
<212> TYPE: PRT
<213> ORGANISM: Homo sapiens
<220> FEATURE:
<221> NAME/KEY: MISC_FEATURE
<223> OTHER INFORMATION: tmpk F105Y mutant

<400> SEQUENCE: 16
```

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
                20                  25                  30

Ala Gly His Arg Ala Glu Leu Leu Arg Phe Pro Glu Arg Ser Thr Glu
            35                  40                  45

Ile Gly Lys Leu Leu Ser Ser Tyr Leu Gln Lys Lys Ser Asp Val Glu
        50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Tyr Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175

Met Val Asp Ala Ser Lys Ser Ile Glu Ala Val His Glu Asp Ile Arg
            180                 185                 190

Val Leu Ser Glu Asp Ala Ile Arg Thr Ala Thr Glu Lys Pro Leu Gly
        195                 200                 205

Glu Leu Trp Lys
    210

```
<210> SEQ ID NO 17
<211> LENGTH: 214
<212> TYPE: PRT
<213> ORGANISM: Homo sapiens
<220> FEATURE:
<221> NAME/KEY: MISC_FEATURE
<223> OTHER INFORMATION: tmpk R16GLL mutant

<400> SEQUENCE: 17
```

Met Ala Ala Arg Arg Gly Ala Leu Ile Val Leu Glu Gly Val Asp Gly
1               5                   10                  15

Ala Gly Lys Ser Thr Gln Ser Arg Lys Leu Val Glu Ala Leu Cys Ala
                20                  25                  30

Ala Gly His Arg Ala Glu Leu Leu Arg Phe Pro Glu Arg Ser Thr Glu
            35                  40                  45

Ile Gly Lys Leu Leu Ser Ser Tyr Leu Gln Lys Lys Ser Asp Val Glu
        50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

```
Arg Tyr Ala Phe Ser Gly Val Ala Phe Thr Gly Ala Lys Glu Asn Phe
            100                 105                 110
Ser Leu Asp Trp Cys Lys Gln Pro Asp Val Gly Leu Pro Lys Pro Asp
            115                 120                 125
Leu Val Leu Phe Leu Gln Leu Thr Pro Glu Val Gly Leu Lys Arg Ala
130                 135                 140
Arg Ala Arg Gly Glu Leu Asp Arg Tyr Glu Asn Gly Ala Phe Gln Glu
145                 150                 155                 160
Arg Ala Leu Arg Cys Phe His Gln Leu Met Lys Asp Thr Thr Leu Asn
                165                 170                 175
Trp Lys Met Val Asp Ala Ser Lys Ser Ile Glu Ala Val His Glu Asp
            180                 185                 190
Ile Arg Val Leu Ser Glu Asp Ala Ile Ala Thr Ala Thr Glu Lys Pro
            195                 200                 205
Leu Gly Glu Leu Trp Lys
    210
```

<210> SEQ ID NO 18
<211> LENGTH: 3513
<212> TYPE: DNA
<213> ORGANISM: Artificial Sequence
<220> FEATURE:
<223> OTHER INFORMATION: Synthetic Construct (pHR Backbone)

<400> SEQUENCE: 18

```
aattacctgt ggtttcattt actctaaacc tgtgattcct ctgaattatt ttcattttaa    60
agaaattgta tttgttaaat atgtactaca aacttagtag ttggaagggc taattcactc   120
ccaaagaaga caagatatcc ttgatctgtg gatctaccac acacaaggct acttccctga   180
ttagcagaac tacacaccag ggccaggggt cagatatcca ctgacctttg gatggtgcta   240
caagctagta ccagttgagc cagataaggt agaagaggcc aataaaggag agaacaccag   300
cttgttacac cctgtgagcc tgcatgggat ggatgacccg gagagagaag tgttagagtg   360
gaggtttgac agccgcctag catttcatca cgtggcccga gagctgcatc cggagtactt   420
caagaactgc tgatatcgag cttgctacaa gggacttttcc gctggggact ttccaggag    480 gcgtggcctg ggcgggactg gggagtggcg agccctcaga tcctgcatat aagcagctgc   540
tttttgcctg tactgggtct ctctggttag accagatctg agcctgggag ctctctggct   600
aactagggaa cccactgctt aagcctcaat aaagcttgcc ttgagtgctt caagtagtgt   660
gtgcccgtct gttgtgtgac tctggtaact agagatccct cagacccttt tagtcagtgt   720
ggaaaatctc tagcagtggc gcccgaacag ggacttgaaa gcgaaaggga accagagga    780 gctctctcga cgcaggactc ggcttgctga agcgcgcacg gcaagaggcg aggggcggcg   840
actggtgagt acgccaaaaa ttttgactag cggaggctag aaggagagag atgggtgcga   900
gagcgtcagt attaagcggg ggagaattag atcgcgatgg gaaaaaattc ggttaaggcc   960
agggggaaag aaaaaatata aattaaaaca tatagtatgg gcaagcaggg agctagaacg  1020
attcgcagtt aatcctggcc tgttagaaac atcagaaggc tgtagacaaa tactgggaca  1080
gctacaacca tcccttcaga caggatcaga gaacttaga tcattatata atacagtagc   1140
aaccctctat tgtgtgcatc aaaggataga gataaaagac accaaggaag ctttagacaa  1200
gatagaggaa gagcaaaaca aaagtaagac caccgcacag caagcggccg ctgatcttca  1260
gacctggagg aggagatatg agggacaatt ggagaagtga attatataaa tataaagtag  1320
```

```
taaaaattga accattagga gtagcaccca ccaaggcaaa gagaagagtg gtgcagagag    1380
aaaaaagagc agtgggaata ggagctttgt tccttgggtt cttggagca gcaggaagca    1440 ctatgggcgc agcgtcaatg acgctgacgg tacaggccag acaattattg tctggtatag    1500
tgcagcagca gaacaatttg ctgagggcta ttgaggcgca acagcatctg ttgcaactca    1560
cagtctgggg catcaagcag ctccaggcaa gaatcctggc tgtggaaaga tacctaaagg    1620
atcaacagct cctggggatt tggggttgct ctggaaaact catttgcacc actgctgtgc    1680
cttggaatgc tagttggagt aataaatctc tggaacagat ttggaatcac acgacctgga    1740
tggagtggga cagagaaatt aacaattaca caagcttaat acactcctta attgaagaat    1800
cgcaaaacca gcaagaaaag aatgaacaag aattattgga attagataaa tgggcaagtt    1860
tgtggaattg gtttaacata acaaattggc tgtggtatat aaaattattc ataatgatag    1920
taggaggctt ggtaggttta agaatagttt ttgctgtact ttctatagtg aatagagtta    1980
ggcagggata ttcaccatta tcgtttcaga cccacctccc aaccccgagg ggacccgaca    2040
ggcccgaagg aatagaagaa gaaggtggag agagagacag agacagatcc attcgattag    2100
tgaacggatc tcgacggtat cgattttaaa agaaagggg ggattggggg gtacagtgca    2160
ggggaaagaa tagtagacat aatagcaaca gacatacaaa ctaaagaatt acaaaaacaa    2220
attacaaaaa ttcaaaattt tatcgataag ctttgcaaag atggataaag ttttaaacag    2280
agaggaatct ttgcagctaa tggaccttct aggtcttgaa aggagtggga attggctccg    2340
gtgcccgtca gtgggcagag cgcacatcgc ccacagtccc cgagaagttg ggggagggg    2400 tcggcaattg aaccggtgcc tagagaaggt ggcgcgggt aaactgggaa agtgatgtcg    2460
tgtactggct ccgcctttt cccgagggtg ggggagaacc gtatataagt gcagtagtcg    2520
ccgtgaacgt tctttttcgc aacgggtttg ccgccagaac acaggtaagt gccgtgtgtg    2580
gttcccgcgg gcctggcctc tttacgggtt atggcccttg cgtgccttga attacttcca    2640
cctggctgca gtacgtgatt cttgatcccg agcttcgggt tggaagtggg tgggagagtt    2700
cgaggccttg cgcttaagga gccccttcgc ctcgtgcttg agttgaggcc tggcctgggc    2760
gctggggccg ccgcgtgcga atctggtggc accttgcgc ctgtctcgct gctttcgata    2820
agtctctagc catttaaaat ttttgatgac ctgctgcgac gctttttttc tggcaagata    2880
gtcttgtaaa tgcgggccaa gatctgcaca ctggtatttc ggttttggg gccgcgggcg    2940 gcgacgggc ccgtgcgtcc cagcgcacat gttcggcgag gcggggcctg cgagcgcggc    3000
caccgagaat cggacggggg tagtctcaag ctggccggcc tgctctggtg cctgcctcg    3060 cgccgccgtg tatcgccccg ccctgggcgg caaggctggc ccggtcggca ccagttgcgt    3120
gagcggaaag atggccgctt cccggccctg ctgcagggga ctcaaaatgg aggacgcggc    3180
gctcgggaga gcggcgggt gagtcaccca cacaaaggaa aagggccttt ccgtcctcag    3240
ccgtcgcttc atgtgactcc acggagtacc gggcgccgtc caggcacctc gattagttct    3300
cgagcttttg gagtacgtcg tctttaggtt ggggggaggg gttttatgcg atggagtttc    3360
cccacactga gtgggtggag actgaagtta ggccagcttg gcacttgatg taattctcct    3420
tggaatttgc ccttttgag tttggatctt ggttcattct caagcctcag acagtggttc    3480
aaagtttttt tcttccattt caggtgtcgt gag                                 3513

<210> SEQ ID NO 19
<211> LENGTH: 11122
<212> TYPE: DNA
<213> ORGANISM: Artificial Sequence
```

<220> FEATURE:
<223> OTHER INFORMATION: Synthetic Construct (pHR Backbone)

<400> SEQUENCE: 19

```
aattacctgt ggtttcattt actctaaacc tgtgattcct ctgaattatt ttcattttaa      60
agaaattgta tttgttaaat atgtactaca aacttagtag ttggaagggc taattcactc     120
ccaaagaaga caagatatcc ttgatctgtg gatctaccac acacaaggct acttccctga     180
ttagcagaac tacacaccag gccaggggt cagatatcca ctgacctttg gatggtgcta      240
caagctagta ccagttgagc cagataaggt agaagaggcc aataaaggag agaacaccag     300
cttgttacac cctgtgagcc tgcatggat ggatgacccg agagagaag tgttagagtg       360
gaggtttgac agccgcctag catttcatca cgtggcccga gagctgcatc cggagtactt     420
caagaactgc tgatatcgag cttgctacaa gggactttcc gctggggact tccagggag     480
gcgtggcctg gcgggactg gggagtggcg agccctcaga tcctgcatat aagcagctgc     540
tttttgcctg tactgggtct ctctggttag accagatctg agcctgggag ctctctggct     600
aactagggaa cccactgctt aagcctcaat aaagcttgcc ttgagtgctt caagtagtgt     660
gtgcccgtct gttgtgtgac tctggtaact agagatccct cagacccttt tagtcagtgt     720
ggaaaatctc tagcagtggc gcccgaacag ggacttgaaa gcgaaaggga aaccagagga    780
gctctctcga cgcaggactc ggcttgctga agcgcgcacg gcaagaggcg aggggcggcg    840
actggtgagt acgccaaaaa ttttgactag cggaggctag aaggagagag atgggtgcga    900
gagcgtcagt attaagcggg ggagaattag atcgcgatgg gaaaaaattc ggttaaggcc    960
agggggaaag aaaaaatata aattaaaaca tatagtatgg gcaagcaggg agctagaacg   1020
attcgcagtt aatcctggcc tgttagaaac atcagaaggc tgtagacaaa tactgggaca   1080
gctacaacca tcccttcaga caggatcaga agaacttaga tcattatata atacagtagc   1140
aaccctctat tgtgtgcatc aaaggataga gataaaagac accaaggaag ctttagacaa   1200
gatagaggaa gagcaaaaca aaagtaagac caccgcacag caagcggccg ctgatcttca   1260
gacctggagg aggagatatg agggacaatt ggagaagtga attatataaa tataaagtag   1320
taaaaattga accattagga gtagcaccca ccaaggcaaa gagaagagtg gtgcagagag   1380
aaaaaagagc agtgggaata ggagctttgt tccttgggtt cttgggagca gcaggaagca   1440
ctatgggcgc agcgtcaatg acgctgacgg tacaggccag acaattattg tctggtatag   1500
tgcagcagca gaacaatttg ctgagggcta ttgaggcgca acagcatctg ttgcaactca   1560
cagtctgggg catcaagcag ctccaggcaa gaatcctggc tgtggaaaga tacctaaagg   1620
atcaacagct cctggggatt tggggttgct ctggaaaact catttgcacc actgctgtgc   1680
cttgaatgc tagttggagt aataaatctc tggaacagat ttggaatcac acgacctgga   1740
tggagtggga cagagaaatt aacaattaca caagcttaat acactcctta attgaagaat   1800
cgcaaaacca gcaagaaaag aatgaacaag aattattgga attagataaa tgggcaagtt   1860
tgtggaattg gtttaacata acaaattggc tgtggtatat aaaattattc ataatgatag   1920
taggaggctt ggtaggttta agaatagttt ttgctgtact ttctatagtg aatagagtta   1980
ggcagggata ttcaccatta tcgtttcaga cccacctccc aaccccgagg ggacccgaca   2040
ggcccgaagg aatagaagaa gaaggtggag agagagacag agacagatcc attcgattag   2100
tgaacggatc tcgacggtat cgattttaaa agaaaggggg gattgggggg gtacagtgca   2160
ggggaaagaa tagtagacat aatagcaaca gacatacaaa ctaaagaatt acaaaaacaa   2220
```

```
attacaaaaa ttcaaaattt tatcgataag ctttgcaaag atggataaag ttttaaacag    2280
agaggaatct ttgcagctaa tggaccttct aggtcttgaa aggagtggga attggctccg    2340
gtgcccgtca gtgggcagag cgcacatcgc ccacagtccc cgagaagttg ggggagggg     2400 tcggcaattg aaccggtgcc tagagaaggt ggcgcgggt aaactgggaa agtgatgtcg     2460
tgtactggct ccgccttttt cccgagggtg ggggagaacc gtatataagt gcagtagtcg    2520
ccgtgaacgt tcttttttcgc aacgggtttg ccgccagaac acaggtaagt gccgtgtgtg   2580
gttcccgcgg gcctggcctc tttacgggtt atggcccttg cgtgccttga attacttcca    2640
cctggctgca gtacgtgatt cttgatcccg agcttcgggt tggaagtggg tgggagagtt    2700
cgaggccttg cgcttaagga gccccttcgc ctcgtgcttg agttgaggcc tggcctgggc    2760
gctggggccg ccgcgtgcga atctggtggc accttcgcgc ctgtctcgct gctttcgata    2820
agtctctagc catttaaaat ttttgatgac ctgctgcgac gctttttttc tggcaagata    2880
gtcttgtaaa tgcgggccaa gatctgcaca ctggtatttc ggttttggg gccgcgggcg     2940 gcgacggggc ccgtgcgtcc cagcgcacat gttcggcgag gcgggcctg cgagcgcggc     3000 caccgagaat cggacggggg tagtctcaag ctggccggcc tgctctggtg cctggcctcg    3060
cgccgccgtg tatcgccccg ccctgggcgg caaggctggc ccggtcggca ccagttgcgt    3120
gagcggaaag atggccgctt cccggccctg ctgcaggag ctcaaaatgg aggacgcggc     3180
gctcgggaga gcgggcgggt gagtcaccca cacaaaggaa aagggccttt ccgtcctcag    3240
ccgtcgcttc atgtgactcc acggagtacc gggcgccgtc caggcacctc gattagttct    3300
cgagcttttg gagtacgtcg tctttaggtt gggggaggg gttttatgcg atggagtttc     3360
cccacactga gtgggtggag actgaagtta ggccagcttg cacttgatg taattctcct     3420 tggaatttgc ccttttttgag tttggatctt ggttcattct caagcctcag acagtggttc    3480 aaagttttt tcttccattt caggtgtcgt gaggaattcg gatccaagct tcaattgtgg     3540
tcactcgaca atcaacctct ggattacaaa atttgtgaaa gattgactgg tattcttaac    3600
tatgttgctc cttttacgct atgtggatac gctgctttaa tgcctttgta tcatgctatt    3660
gcttcccgta tggctttcat tttctcctcc ttgtataaat cctggttgct gtctcttat     3720 gaggagttgt ggcccgttgt caggcaacgt ggcgtggtgt gcactgtgtt tgctgacgca    3780
acccccactg gttggggcat tgccaccacc tgtcagctcc tttccgggac tttcgctttc    3840
cccctcccta ttgccacggc ggaactcatc gccgcctgcc ttgcccgctg ctggacaggg    3900
gctcggctgt tgggcactga caattccgtg gtgttgtcgg ggaagctgac gtccttcca    3960 tggctgctcg cctgtgttgc cacctggatt ctgcgcggga cgtccttctg ctacgtccct    4020
tcggccctca atccagcgga ccttccttcc cgcggcctgc tgccggctct gcggcctctt    4080
ccgcgtcttc gccttcgccc tcagacgagt cggatctccc tttgggccgc ctccccgcct    4140
gctcgagacc tagaaaaaca tggagcaatc acaagtagca atacagcagc taccaatgct    4200
gattgtgcct ggctagaagc acaagaggag gaggaggtgg ttttccagt cacacctcag     4260 gtaccttta gaccaatgac ttacaaggca gctgtagatc ttagccactt tttaaagaa     4320 aagggggac tggaagggct aattcactcc caacgaagac aagatctgct ttttgcttgt     4380
actgggtctc tctggttaga ccagatctga gcctgggagc tctctggcta actagggaac    4440
ccactgctta agcctcaata aagcttgcct tgagtgcttc aagtagtgtg tgcccgtctg    4500
ttgtgtgact ctggtaacta gagatccctc agacccttt agtcagtgtg aaaatctct      4560 agcagtagta gttcatgtca tcttattatt cagtatttat aacttgcaaa gaaatgaata    4620
```

```
tcagagagtg agaggccttg acattataat agatttagca ggaattgaac taggagtgga    4680
gcacacaggc aaagctgcag aagtacttgg aagaagccac cagagatact cacgattctg    4740
cacatacctg gctaatccca gatcctaagg attacattaa gtttactaac atttatataa    4800
tgatttatag tttaaagtat aaacttatct aatttactat tctgacagat attaattaat    4860
cctcaaatat cataagagat gattactatt atccccattt aacacaagag gaaactgaga    4920
gggaaagatg ttgaagtaat tttcccacaa ttacagcatc cgttagttac gactctatga    4980
tcttctgaca caaattccat ttactcctca ccctatgact cagtcgaata tatcaaagtt    5040
atggacatta tgctaagtaa caaattaccc ttttatatag taaatactga gtagattgag    5100
agaagaaatt gtttgcaaac ctgaatagct tcaagaagaa gagaagtgag gataagaata    5160
acagttgtca tttaacaagt tttaacaagt aacttggtta gaaagggatt caaatgcata    5220
aagcaaggga taaatttttc tggcaacaag actatacaat ataaccttaa atatgacttc    5280
aaataattgt tggaacttga taaaactaat taaatattat tgaagattat caatattata    5340
aatgtaattt acttttaaaa agggaacata gaaatgtgta tcattagagt agaaaacaat    5400
ccttattatc acaatttgtc aaaacaagtt tgttattaac acaagtagaa tactgcattc    5460
aattaagttg actgcagatt ttgtgttttg ttaaaattag aaagagataa caacaatttg    5520
aattattgaa agtaacatgt aaatagttct acatacgttc ttttgacatc ttgttcaatc    5580
attgatcgaa gttctttatc ttggaagaat ttgttccaaa gactctgaaa taaggaaaac    5640
aatctattat atagtctcac accttttgttt tacttttagt gatttcaatt taataatgta    5700
aatggttaaa atttattctt ctctgagatc atttcacatt gcagatagaa aacctgagac    5760
tggggtaatt tttattaaaa tctaatttaa tctcagaaac acatctttat tctaacatca    5820 attttttccag tttgatatta tcatataaag tcagccttcc tcatctgcag gttccacaac    5880
aaaaatccaa ccaactgtgg atcaaaaata ttgggaaaaa attaaaaata gcaatacaac    5940
aataaaaaaa tacaaatcag aaaaacagca cagtataaca actttattta gcatttacaa    6000
tctattaggt attataagta atctagaatt aattccgtgt attctatagt gtcacctaaa    6060
tcgtatgtgt atgatacata aggttatgta ttaattgtag ccgcgttcta acgacaatat    6120
gtacaagcct aattgtgtag catctggctt actgaagcag accctatcat ctctctcgta    6180
aactgccgtc agagtcggtt tggttggacg aaccttctga gttctggta acgccgtccc    6240 gcacccggaa atggtcagcg aaccaatcag cagggtcatc gctagccaga tcctctacgc    6300
cggacgcatc gtgccggca tcaccggcgc cacaggtgcg gttgctggcg cctatatcgc    6360
cgacatcacc gatggggaag atcgggctcg ccacttcggg ctcatgagcg cttgtttcgg    6420
cgtgggtatg gtggcaggcc ccgtggccgg gggactgttg ggcgccatct ccttgcatgc    6480
accattcctt gcggcggcgg tgctcaacgg cctcaaccta ctactgggct gcttcctaat    6540
gcaggagtcg cataagggag agcgtcgaat ggtgcactct cagtacaatc tgctctgatg    6600
ccgcatagtt aagccagccc cgacacccgc caacacccgc tgacgcgccc tgacgggctt    6660
gtctgctccc ggcatccgct tacagacaag ctgtgaccgt ctccgggagc tgcatgtgtc    6720
agaggttttc accgtcatca ccgaaacgcg cgagacgaaa gggcctcgtg atacgcctat    6780
ttttataggt taatgtcatg ataataatgg tttcttagac gtcaggtggc acttttcggg    6840
gaaatgtgcg cggaaccccct atttgtttat ttttctaaat acattcaaat atgtatccgc    6900
tcatgagaca ataaccctga taaatgcttc aataatattg aaaaggaag agtatgagta    6960
```

-continued

```
ttcaacatttt ccgtgtcgcc cttattccct tttttgcggc attttgcctt cctgttttg      7020
ctcacccaga aacgctggtg aaagtaaaag atgctgaaga tcagttgggt gcacgagtgg      7080
gttacatcga actggatctc aacagcggta agatccttga gagttttcgc cccgaagaac      7140
gttttccaat gatgagcact tttaaagttc tgctatgtgg cgcggtatta tcccgtattg      7200
acgccgggca agagcaactc ggtcgccgca tacactattc tcagaatgac ttggttgagt      7260
actcaccagt cacagaaaag catcttacgg atggcatgac agtaagagaa ttatgcagtg      7320
ctgccataac catgagtgat aacactgcgg ccaacttact tctgacaacg atcggaggac      7380
cgaaggagct aaccgctttt ttgcacaaca tgggggatca tgtaactcgc cttgatcgtt      7440
gggaaccgga gctgaatgaa gccataccaa acgacgagcg tgacaccacg atgcctgtag      7500
caatggcaac aacgttgcgc aaactattaa ctggcgaact acttactcta gcttcccggc      7560
aacaattaat agactggatg gaggcggata agttgcagg accacttctg cgctcggccc       7620
ttccggctgg ctggtttatt gctgataaat ctggagccgg tgagcgtggg tctcgcggta      7680
tcattgcagc actggggcca gatggtaagc cctcccgtat cgtagttatc tacacgacgg      7740
ggagtcaggc aactatggat gaacgaaata gacagatcgc tgagataggt gcctcactga      7800
ttaagcattg gtaactgtca gaccaagttt actcatatat actttagatt gatttaaaac      7860
ttcatttta atttaaaagg atctaggtga agatcctttt tgataatctc atgaccaaaa       7920
tcccttaacg tgagttttcg ttccactgag cgtcagaccc cgtagaaaag atcaaaggat      7980
cttcttgaga tccttttttt ctgcgcgtaa tctgctgctt gcaaacaaaa aaaccaccgc      8040
taccagcggt ggtttgtttg ccggatcaag agctaccaac tcttttttccg aaggtaactg     8100
gcttcagcag agcgcagata ccaaatactg ttcttctagt gtagccgtag ttaggccacc      8160
acttcaagaa ctctgtagca ccgcctacat acctcgctct gctaatcctg ttaccagtgg      8220
ctgctgccag tggcgataag tcgtgtctta ccgggttgga ctcaagacga tagttaccgg      8280
ataaggcgca gcggtcgggc tgaacggggg gttcgtgcac acagcccagc ttggagcgaa      8340
cgacctacac cgaactgaga tacctacagc gtgagctatg agaaagcgcc acgcttcccg      8400
aagggagaaa ggcggacagg tatccggtaa gcggcagggt cggaacagga gagcgcacga      8460
gggagcttcc agggggaaac gcctggtatc tttatagtcc tgtcgggttt cgccacctct      8520
gacttgagcg tcgatttttg tgatgctcgt caggggggcg gagcctatgg aaaaacgcca      8580
gcaacgcggc ctttttacgg ttcctggcct tttgctggcc ttttgctcac atgttctttc      8640
ctgcgttatc ccctgattct gtggataacc gtattaccgc ctttgagtga gctgataccg      8700
ctcgccgcag ccgaacgacc gagcgcagcg agtcagtgag cgaggaagcg gaagagcgcc      8760
caatacgcaa accgcctctc cccgcgcgtt ggccgattca ttaatgcagc tgtggaatgt      8820
gtgtcagtta gggtgtggaa agtccccagg ctccccagca ggcagaagta tgcaaagcat      8880
gcatctcaat tagtcagcaa ccaggtgtgg aaagtcccca ggctcccag caggcagaag       8940
tatgcaaagc atgcatctca attagtcagc aaccatagtc cgcccctaa ctccgcccat       9000
cccgccccta actccgccca gttccgccca ttctccgccc catggctgac taatttttttt    9060
tatttatgca gaggccgagg ccgcctcggc ctctgagcta ttccagaagt agtgaggagg      9120
cttttttgga ggcctaggct tttgcaaaaa gcttggacac aagacaggct tgcgagatat      9180
gtttgagaat accactttat cccgcgtcag gagaggcag tgcgtaaaaa gacgcggact       9240
catgtgaaat actggttttt agtgcgccag atctctataa tctcgcgcaa cctatttttcc     9300
cctcgaacac ttttttaagcc gtagataaac aggctgggac acttcacatg agcgaaaaat    9360
```

```
acatcgtcac ctgggacatg ttgcagatcc atgcacgtaa actcgcaagc cgactgatgc    9420
cttctgaaca atggaaaggc attattgccg taagccgtgg cggtctgtac cgggtgcgtt    9480
actggcgcgt gaactgggta ttcgtcatgt cgataccgtt tgtatttcca gctacgatca    9540
cgacaaccag cgcgagctta aagtgctgaa acgcgcagaa ggcgatggcg aaggcttcat    9600
cgttattgat gacctggtgg ataccggtgg tactgcggtt gcgattcgtg aaatgtatcc    9660
aaaagcgcac tttgtcacca tcttcgcaaa accggctggt cgtccgctgg ttgatgacta    9720
tgttgttgat atcccgcaag atacctggat tgaacagccg tgggatatgg gcgtcgtatt    9780
cgtcccgcca atctccggtc gctaatcttt tcaacgcctg gcactgccgg gcgttgttct    9840
ttttaacttc aggcgggtta caatagtttc cagtaagtat tctggaggct gcatccatga    9900
cacaggcaaa cctgagcgaa accctgttca accccgctt taaacatcct gaaacctcga    9960
cgctagtccg ccgctttaat cacggcgcac aaccgcctgt gcagtcggcc cttgatggta   10020
aaaccatccc tcactggtat cgcatgatta ccgtctgat gtggatctgg cgcggcattg   10080
acccacgcga atcctcgac gtccaggcac gtattgtgat gagcgatgcc gaacgtaccg   10140
acgatgattt atacgatacg gtgattggct accgtggcgg caactggatt tatgagtggg   10200
ccccggatct ttgtgaagga accttacttc tgtggtgtga cataattgga caaactacct   10260
acagagattt aaagctctaa ggtaaatata aattttaa gtgtataatg tgttaaacta   10320
ctgattctaa ttgtttgtgt attttagatt ccaacctatg gaactgatga atgggagcag   10380
tggtggaatg cctttaatga ggaaaacctg ttttgctcag aagaaatgcc atctagtgat   10440
gatgaggcta ctgctgactc tcaacattct actcctccaa aaagaagag aaaggtagaa   10500 gacccccaag gactttcctt cagaattgcta agtttttga gtcatgctgt gtttagtaat   10560
agaactcttg cttgctttgc tatttacacc acaaaggaaa aagctgcact gctatacaag   10620
aaaattatgg aaaatattc tgtaaccttt ataagtaggc ataacagtta taatcataac   10680
atactgtttt ttcttactcc acacaggcat agagtgtctg ctattaataa ctatgctcaa   10740
aaattgtgta cctttagctt tttaatttgt aagggggtta ataaggaata tttgatgtat   10800
agtgccttga ctagagatca taatcagcca taccacatt gtagaggttt tacttgcttt   10860
aaaaaacctc ccacacctcc ccctgaacct gaaacataaa atgaatgcaa ttgttgttgt   10920
taacttgttt attgcagctt ataatggtta caaataaagc aatagcatca caaatttcac   10980
aaataaagca tttttttcac tgcattctag ttgtggtttg tccaaactca tcaatgtatc   11040
ttatcatgtc tggatcaact ggataactca agctaaccaa atcatccca aacttccac   11100 cccataccct attaccactg cc                                             11122
```

<210> SEQ ID NO 20
<211> LENGTH: 1611
<212> TYPE: DNA
<213> ORGANISM: Artificial Sequence
<220> FEATURE:
<223> OTHER INFORMATION: Synthetic Construct (hIL-12 elasti (p40:p35)
      ORF)

<400> SEQUENCE: 20

```
atgggtcacc agcagttggt catctcttgg ttttccctgg ttttctggc atctcccctc     60 gtggccatat gggaactgaa gaaagatgtt tatgtcgtag aattggattg gtatccggat    120
gcccctggag aaatggtggt cctcacctgt gacacccctg aagaagatgg tatcacctgg    180
accttggacc agagcagtga ggtcttaggc tctggcaaaa ccctgaccat ccaagtcaaa    240
```

```
gagtttggag atgctggcca gtacacctgt cacaaaggag gcgaggttct aagccattcg    300
ctcctgctgc ttcacaaaaa ggaagatgga atttggtcca ctgatatttt aaaggaccag    360
aaagaaccca aaataagac ctttctaaga tgcgaggcca agaattattc tggacgtttc     420
acctgctggt ggctgacgac aatcagtact gatttgacat tcagtgtcaa aagcagcaga    480
ggctcttctg accccaaagg ggtgacgtgc ggagctgcta cactctctgc agagagagtc    540 agagggggaca caaggagta tgagtactca gtggagtgcc aggaggacag tgcctgccca    600
gctgctgagg agagtctgcc cattgaggtc atggtggatg ccgttcacaa gctcaagtat    660
gaaaactaca ccagcagctt cttcatcagg gacatcatca aacctgaccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagtgttcct ggagtagggg tacctggggt gggcgccaga    1020
aacctccccg tggccactcc agacccagga atgttcccat gccttcacca ctcccaaaac    1080
ctgctgaggg ccgtcagcaa catgctccag aaggccagac aaactctaga attttaccct    1140
tgcacttctg aagagattga tcatgaagat atcacaaaag ataaaaccag cacagtggag    1200
gcctgtttac cattggaatt aaccaagaat gagagttgcc taaattccag agagacctct    1260
ttcataacta atgggagttg cctggcctcc agaaagacct cttttatgat ggccctgtgc    1320
cttagtagta tttatgaaga ctcgaagatg taccaggtgg agttcaagac catgaatgca    1380
aagcttctga tggatcctaa gaggcagatc tttctagatc aaaacatgct ggcagttatt    1440
gatgagctga tgcaggccct gaatttcaac agtgagactg tgccacaaaa atcctccctt    1500
gaagaaccgg attttatataa aactaaaatc aagctctgca tacttcttca tgctttcaga    1560
attcgggcag tgactattga tagagtgatg agctatctga atgcttccta a             1611
```

<210> SEQ ID NO 21
<211> LENGTH: 1623
<212> TYPE: DNA
<213> ORGANISM: Artificial Sequence
<220> FEATURE:
<223> OTHER INFORMATION: Synthetic Construct (mIL-12 (p35p40) ORF)

<400> SEQUENCE: 21

```
atgggtcaat cacgctacct cctcttttg gccacccttg cctcctaaa ccacctcagt       60 ttggccaggg tcattccagt ctctggacct gccaggtgtc ttagccagtc ccgaaacctg     120
ctgaagacca cagatgacat ggtgaagacg gccagagaaa agctgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gccccccacag aagacgtctt tgatgatgac cctgtgcctt    360
ggtagcatct atgaggactt gaagatgtac cagacagagt ccaggccat caacgcagca     420 cttcagaatc acaaccatca gcagatcatt ctagacaagg catgctggt ggccatcgat     480 gagctgatgc agtctctgaa tcataatggc gagactctgc ccagaaacc tcctgtggga     540 gaagcagacc cttacagagt gaaaatgaag ctctgcatcc tgcttcacgc cttcagcacc    600
cgcgtcgtga ccatcaacag ggtgatgggc tatctgagct ccgccgttcc tggagtaggg    660
```

```
gtacctggag tgggcggatc tatgtgggag ctggagaaag acgtttatgt tgtagaggtg    720
gactggactc ccgatgcccc tggagaaaca gtgaacctca cctgtgacac gcctgaagaa    780
gatgacatca cctggacctc agaccagaga catggagtca taggctctgg aaagaccctg    840
accatcactg tcaaagagtt tctagatgct ggccagtaca cctgccacaa aggaggcgag    900
actctgagcc actcacatct gctgctccac aagaaggaaa atggaatttg gtccactgaa    960
attttaaaaa atttcaaaaa caagactttc ctgaagtgtg aagcaccaaa ttactccgga   1020
cggttcacgt gctcatggct ggtgcaaaga aacatggact tgaagttcaa catcaagagc   1080
agtagcagtc cccccgactc tcgggcagtg acatgtggaa tggcgtctct gtctgcagag   1140
aaggtcacac tggaccaaag ggactatgag aagtattcag tgtcctgcca ggaggatgtc   1200
acctgcccaa ctgccgagga gaccctgccc attgaactgg cgttggaagc acggcagcag   1260
aataaatatg agaactacag caccagcttc ttcatcaggg acatcatcaa accagacccg   1320
cccaagaact tgcagatgaa gcctttgaag aactcacagg tggaggtcag ctgggagtac   1380
cctgactcct ggagcactcc ccattcctac ttctccctca agttctttgt tcgaatccag   1440
cgcaagaaag aaaagatgaa ggagacagag gaggggtgta accagaaagg tgcgttcctc   1500
gtagagaaga catctaccga agtccaatgc aaaggcggga atgtctgcgt gcaagctcag   1560
gatcgctatt acaattcctc atgcagcaag tgggcatgtg ttccctgcag ggtccgatcc   1620
tag                                                                 1623
```